US010773214B2

(12) United States Patent
Nosrati

(10) Patent No.: US 10,773,214 B2
(45) Date of Patent: Sep. 15, 2020

(54) BIOMIMETICALLY DESIGNED MODULAR MICROFLUIDIC-BASED CAPILLARIES AND LYMPHATIC UNITS FOR KIDNEY AND LIVER DIALYSIS SYSTEMS, ORGAN BIO-REACTORS AND BIO-ARTIFICIAL ORGAN SUPPORT SYSTEMS

(71) Applicant: Micromedics Inc., Tarzana, CA (US)

(72) Inventor: Saeid Mordechai Nosrati, Tarzana, CA (US)

(*) Notice: Subject to any disclaimer, the term of this patent is extended or adjusted under 35 U.S.C. 154(b) by 457 days.

(21) Appl. No.: 15/060,251

(22) Filed: Mar. 3, 2016

(65) Prior Publication Data

US 2017/0252701 A1  Sep. 7, 2017

(51) Int. Cl.
*B01D 63/08*  (2006.01)
*B01D 61/50*  (2006.01)
(Continued)

(52) U.S. Cl.
CPC ............ *B01D 63/088* (2013.01); *A61F 2/022* (2013.01); *A61M 1/1601* (2014.02); *A61M 1/1621* (2014.02); *A61M 1/1696* (2013.01); *A61M 1/1698* (2013.01); *A61M 1/3413* (2013.01); *A61M 1/3417* (2014.02);
(Continued)

(58) Field of Classification Search
CPC .. A61F 2/02; A61F 2/04; A61F 2/022; A61M 1/1601; A61M 1/1621; A61M 1/1696; A61M 1/1698; A61M 1/3413; A61M 1/3496; A61M 1/3417; A61M 2205/0244; B01D 2313/18; B01D 2313/38; B01D 2313/40; B01D 61/243; B01D 63/088; B01D 63/085; B01D 61/025; B01D 61/48; B01D 61/50; B01D 61/422; B01D 61/425; B01D 2311/25; B01D 2311/2623; B01D 2311/2626; B01D 2311/2649; B01D 2311/2692; B01D 2313/54; B01D 2315/16

See application file for complete search history.

(56) References Cited

U.S. PATENT DOCUMENTS 7,094,345 B2 * 8/2006 Gilbert ................. B01D 63/087
  204/450
7,955,504 B1 * 6/2011 Jovanovic ............. B01D 61/18
  210/321.71

* cited by examiner

*Primary Examiner* — John Kim

(57) ABSTRACT

A technology that provides various modular biomimetic microfluidic modules emulating varieties of microvasculature in body. These microfluidic-base capillaries and lymphatic Technology modules are constructed as multilayered-microfluidic microchannels of various shapes, and aspect ratios using diverse biocompatible microfluidic polymers. Then, various semipermeable membranes are sandwiched in between these multilayered microfluidic microchannels. These membranes have different chemical, physical characteristics and MWCO values. Consequently, this design will produce much smaller dimension channels similar to human vasculature to achieve biomimetic properties like of human organs and tissues. By interchanging microfluidic-layers or the membranes various diverse modules are designed that act as building blocks for constructing various medical devices, various forms of dialysis devices including albumin and lipid dialysis, water purification, bioreactors, bio-artificial organ support systems. Connecting various modules in diverse combinations, permutations, in parallel and/or in series to ultimately design many unrelated medical devices such as dialysis, bioreactors and organ support devices.

36 Claims, 22 Drawing Sheets

(51) Int. Cl.
*A61F 2/02* (2006.01)
*A61F 2/04* (2013.01)
*A61M 1/16* (2006.01)
*A61M 1/34* (2006.01)
*B01D 61/24* (2006.01)
*B01D 61/42* (2006.01)
*B01D 61/02* (2006.01)
*B01D 61/48* (2006.01)

(52) U.S. Cl.
CPC ......... *A61M 1/3496* (2013.01); *B01D 61/243* (2013.01); *B01D 61/50* (2013.01); *B01D 63/085* (2013.01); *A61M 2205/0244* (2013.01); *B01D 61/025* (2013.01); *B01D 61/422* (2013.01); *B01D 61/425* (2013.01); *B01D 61/48* (2013.01); *B01D 2311/25* (2013.01); *B01D 2311/2623* (2013.01); *B01D 2311/2626* (2013.01); *B01D 2311/2649* (2013.01); *B01D 2311/2692* (2013.01); *B01D 2313/18* (2013.01); *B01D 2313/38* (2013.01); *B01D 2313/54* (2013.01); *B01D 2315/16* (2013.01)

| Hollow Fiber Technology | | Ratio (MFC / HFT) | MFC Technology |
|---|---|---|---|
| | F80A | | |
| Volume | 350 ml | 1x | 350 ml |
| SA | 1.8 m² | 2.5x | ~4.5 m² |
| Blood Volume | 110 ml | 0.4x | 45 ml |
| Dialysate | 155 ml | 0.58 | 90 ml |
| Blood/Dialysate | 110/155=0.71 | 0.5/0.71 = 0.7x | 45/90 =0.5 |
| Fiber inner Diameter/Radius | 200/100 um | | |
| Number of hollow fibers | 12300 | 18.02x | 25000 MFC Chips x 9 = 225000 |
| Length of fiber | 28 cm | 1/28x | length of the MFC Channel = 1cm |
| Radius of inner casing | 2 cm | | |
| Volume = (4 cm² X 28 cm X 3.14) = 352 cm³ | | 1x | Casing 3.5 cm x 10 cm x 10 cm = 350 cm³ |
| Volume of one fiber | 0.0088 ml | 0.023x | 0.0002 ml |
| Volume of all fibers | 108 ml | 0.4x | 25000x9x.0002 = 45 ml |
| Volume of dialysate | 155 | 0.58x | Twice channels for dialysate = 90 ml |
| Volume of dialysate/ Blood | 1.4 | 2/1.4 = 1.428x | 90/45= 2 |

FIG. 10

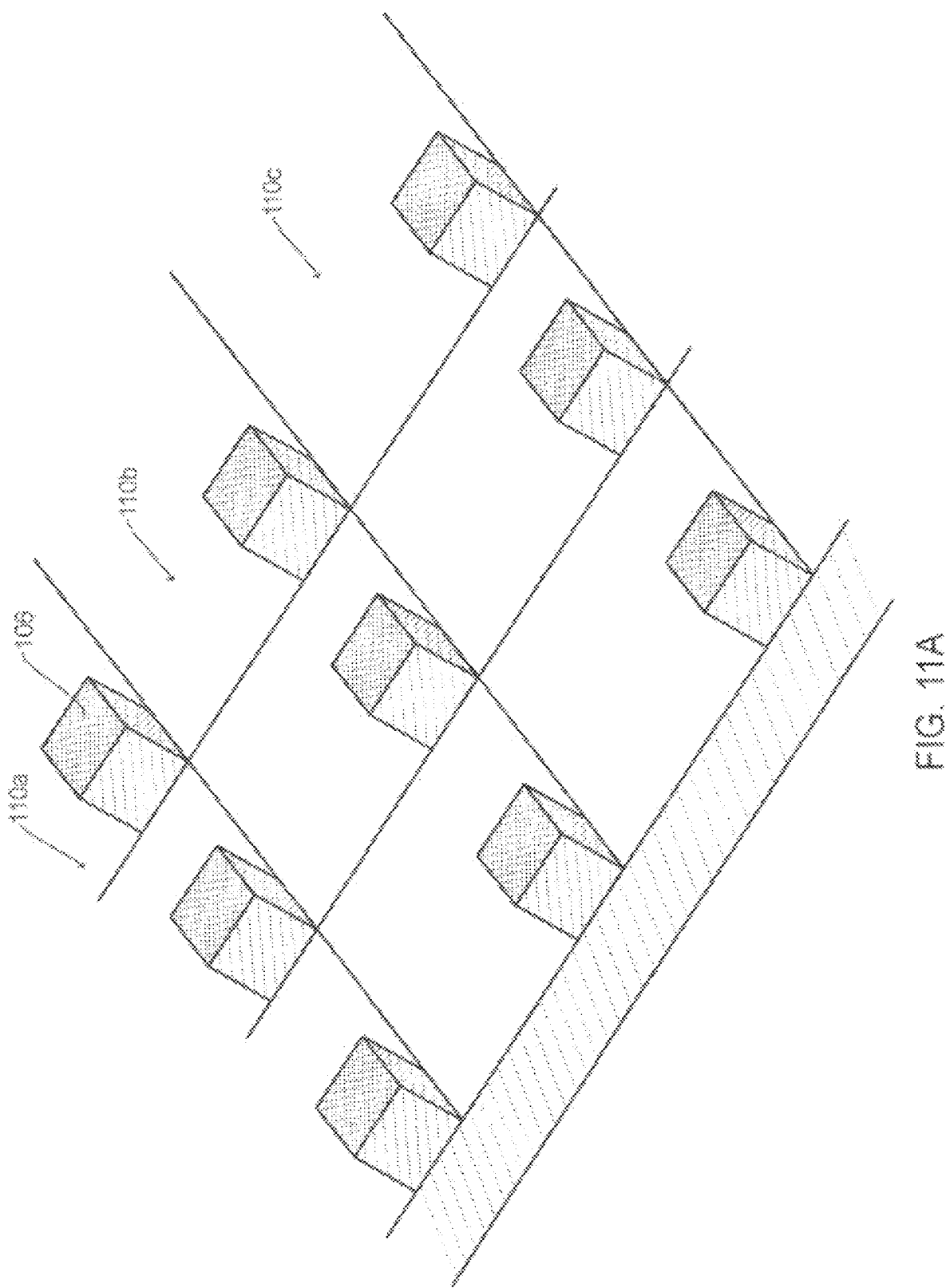

1. 1ˢᵗ layer...Dialysate with charcoal                            Flow → → →
2. 2ⁿᵈ layer...Dialysate with albumin                            Flow ⇐
3. 3ʳᵈ layer...Plasma Portion (P.P.) from plasmapheresis          Flow → → →
4. 4ᵗʰ layer...Dialysate with albumin                            Flow ⇐
5. 5ᵗʰ layer...Dialysate with charcoal                            Flow → → →

1. 1ˢᵗ layer...Dialysate with charcoal                            Depth of channels 20-200um
2. 2ⁿᵈ layer...Dialysate with albumin                            Depth of channels 20-200um
3. 3ʳᵈ layer...Plasma Portion (P.P.) from plasmapheresis          Depth of channels 20-100um
4. 4ᵗʰ (same as 2ⁿᵈ layer)...Dialysate with albumin              Depth of channels 20-200um
5. 5ᵗʰ (same as 1ˢᵗ layer)...Dialysate with charcoal              Depth of channels 20-200um

FIG. 18

Microfluidic Kidney/Liver Replacement Device
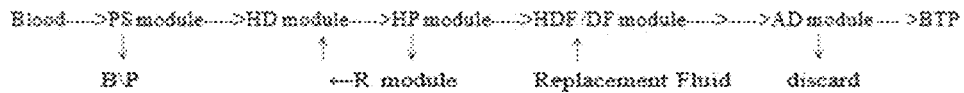
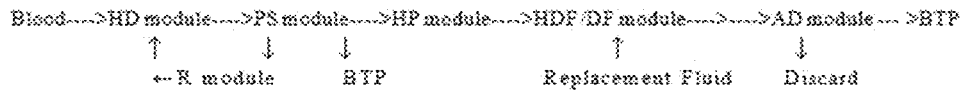
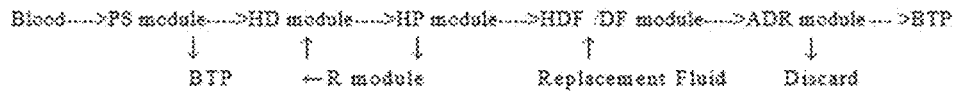
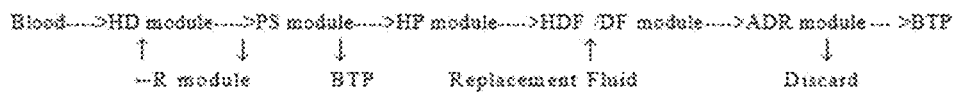
Bio-artificial Microfluidic Kidney/Liver Replacement Device
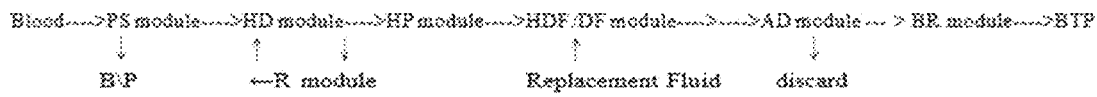
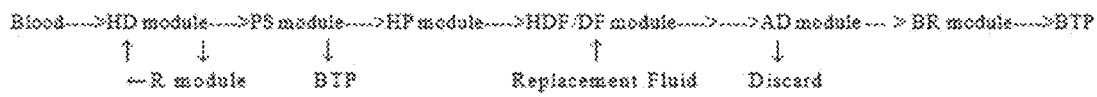
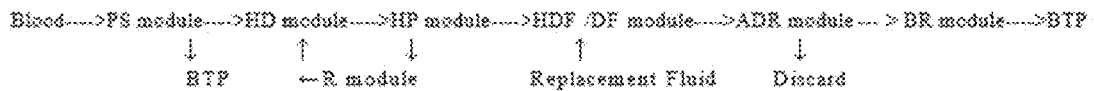
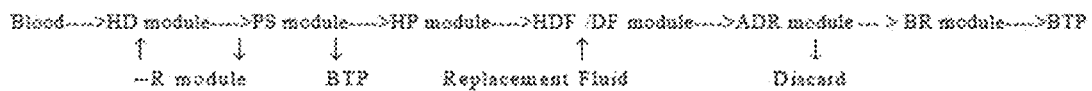
Portable microfluidic Kidney/Liver Replacement Device
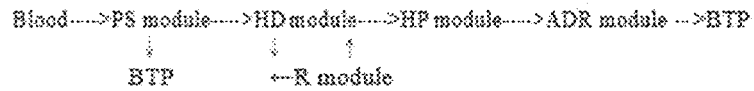
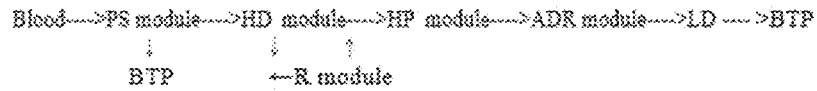
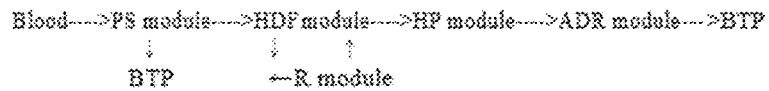
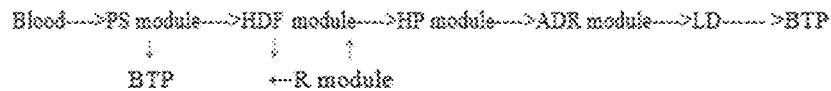
FIG. 19

1. 1st layer...Dialysate with charcoal  Flow → → →
2. 2nd layer...Dialysate with albumin  Flow ⬅
3. 3rd layer...Plasma Portion (P.P.) from plasmapheresis  Flow → → →
4. 4th layer...Dialysate with albumin  Flow ⬅
5. 5th layer...Dialysate with charcoal  Flow → → →

1. 1st layer...Dialysate with charcoal  Depth of channels 20-200um
2. 2nd layer...Dialysate with albumin  Depth of channels 20-200um
3. 3rd layer...Plasma Portion (P.P.) from plasmapheresis  Depth of channels 20-100um
4. 4th (same as 2nd layer)...Dialysate with albumin  Depth of channels 20-200um
5. 5th (same as 1st layer)...Dialysate with charcoal  Depth of channels 20-200um

FIG. 20

1. 1st layer...Dialysate with albumin  Flow ⬅
2. 2nd layer...Plasma Portion from plasmapheresis  Flow → → →
3. 3rd layer...Dialysate with albumin  Flow ⬅

FIG. 21

1. 1st layer...Dialysate with albumin  Flow ⬅
2. 2nd layer...Plasma Portion from plasmapheresis  Flow → → →
3. 3rd layer...Dialysate with albumin  Flow ⬅

FIG. 22

Blood→→PS module→Plasma Portion→→HD module→→HDF module→→back to patient
Back to patient ← Cellular Portion　　　DR module　　　U/F Blood→→PS module→Plasma Portion→→HDF module→→back to patient
Back to patient ←Cellular Portion　　　DR module

FIG. 23

BIOMIMETICALLY DESIGNED MODULAR MICROFLUIDIC-BASED CAPILLARIES AND LYMPHATIC UNITS FOR KIDNEY AND LIVER DIALYSIS SYSTEMS, ORGAN BIO-REACTORS AND BIO-ARTIFICIAL ORGAN SUPPORT SYSTEMS

FIELD OF THE INVENTION

The landmark HEMO study suggests that the current "urea-centric" approach to renal replacement therapy, delivered in the form of thrice weekly HD, does not reduce morbidity and mortality when clearance of urea and small molecular uremic toxins is increased beyond existing clinical guidelines, and the maximum survival benefit using this modality may have already been achieved. Dialysis adequacy should ideally be broadened to incorporate clearance of middle molecular weight uremic toxins along with small solutes, extracellular fluid volume and blood pressure control, electrolyte and acid base control, correction of anemia, and optimization of nutritional status and quality of life. Studies that have explored increased frequency, increased length, and influence of location (home vs. in-center dialysis), have largely focused on existing HD and PD modalities Since current dialysis modalities which are used to treat ESRD patients have such disappointing outcomes, there is an urgent need to improve the current dialysis technologies to achieve better QOL and outcomes for these patients. In addition, the hollow Fiber Technology that is currently in use in all forms of dialysis replacement is highly inefficient and needs to be replaced In the past decade, the quality of dialysis water has been improved with the advances in water preparation, and also with advances in monitoring and disinfection methods As a result, high standards are now readily achievable in clinical practice. Dialysate water can be contaminated by dangerous chemical and microbiological factors, all of which are theoretically hazardous to patients on any form of renal replacement therapies. The chlorine compounds are used to suppress bacterial growth in the water supply and then are removed when the water is treated and prepared for hemodialysis/renal replacement therapies. In standard and conventional dialysate preparation, it is almost impossible to completely prevent bacterial proliferation in the treated water and ultimately from the final dialysate fluid. Hence, conventional dialysate contains some low level of contamination such as microbiological and fragments of endotoxins meets the required quality standards, it usually contains some low level of microbiological contamination, including bacterial fragments, fragments of endotoxin and peptidoglycans—collectively referred to as "cytokine-inducing substances". This is due to the fact that the cytokine inducing substances cross both low-flux and high-flux hemodialysis membranes and stimulate cytokine production by inflammatory cells.

As a result, advances in dialysis membrane technology have refocused attention on water quality and its potential role in the bio-incompatibility of hemodialysis circuits and adverse patient outcomes. The role of ultrapure dialysate is increasingly being advocated, given its proposed clinical benefits and relative ease of production as a result of the widespread use of reverse osmosis and ultrafiltration. The use of dialysate of much higher microbiological purity improved this state of inflammation. General markers of inflammation such as serum C-reactive protein (CRP), ferritin, or fibrinogen are commonly used, but the oxidative stress referred to excessive production of reactive oxygen species (ROS) and inadequate antioxidant protection, is more sensitive, specific, and precocious of inflammation state. This condition leads to structural and/or functional deterioration in cell components including DNA, proteins, carbohydrates, and lipids. The presence of ROS can cause damage in many molecules, such as lipids, leading to the production of malondialdehyde (MDA), an indicator of lipid peroxidation. In chronic renal failure (CRF) patients under hemodialysis (HD) treatment, the formation of ROS is amplified, therefore beyond uremic toxins.

Anytime that a consumable article/element can be manufactured on demand and at a specific location such as in far forward locations; it will lessen the burden on military or the entity for the supply chain. It is evident that items like i.v. fluids are perfect requirements that technological solutions can fulfill. In addition other issues such as removal from the shipping container, or long term storage, could put some stress on the availability of the i.v. fluids where and when it is needed. It is preferable that the system should be operational within 45 minutes with a preferred goal of less than 20 minutes.

Hence, on demand intravenous (i.v.) fluid resuscitation is not only critical but also a vital therapeutic treatment capability that any medical personnel must have in order to perform the life-saving procedures. The requirement for easy as well as expedited access to different types of i.v. fluid solutions as well as capability to administer these i.v. fluid solutions to the patients is of paramount importance and throughout military battle operations.

Currently, the military services meet this requirement by transporting prepackaged i.v. solutions to forward-deployed medical elements and locations, using valuable airlift capacity to haul what are largely water. The climactic conditions in forward-deployed locations often expose i.v. fluids to temperatures outside recommended limits for extended periods of time. Extreme weather conditions combined with limited environmentally controlled storage increases shelf-life and transport risks, frequently resulting in i.v. fluid disposal and logistical re-supply operations.

Those skilled in the art will recognize that Hollow Fiber Membranes were developed in the 1960's. They are constructed of a microporous structure having a dense selective layer on the outside surface. Many fibers must be packed into bundles and potted into tubes to form a membrane module. Modules with a surface area of even a few square feet may require many miles of fibers. Because a module must contain no defective or broken fibers, production requires strict quality control. Hollow fiber membranes can withstand very high pressures from the outside, but are limited on pressure exerted from the inside of the fiber, therefore backwash rates are limited to around twice the normal permeate rate. The feed fluid is applied on the outside of the fibers and the permeate I filtrate is removed down the fiber. Hollow Fiber membranes are also applied in clean water applications and are used in membrane bioreactor (MBR), but are limited to lower concentrations of solids than other membrane types.

This invention is based on a core technology that provides modular, adjustable and scalable microfluidic chipsets units/modules/modules (these terms are used interchangeably throughout the document) that make numerous basic units that emulate different varieties of capillaries and lymphatic in human body. This biomimetically designed, modular and scalable microfluidic-based capillaries and lymphatic Technology (MCAL Technology) is constructed by manufacturing microfluidic-based multitude of micro-channels of various shapes (straight, parallel, crisscross, fractal, loop, and branched), forms and configuration with various aspect ratios using diverse types of inert and biocompatible microfluidic polymer substrates used to manufacture microfluidic systems. Then using diverse types of semipermeable membranes which have different chemical and physical characteristics and molecular weight cut off values to construct two or more layer constructs in which various semipermeable membranes are sandwiched in between a couple or multiple layers of these microfluidic layers containing varieties of micro-channels with different aspect ratios and configurations. As a result this design and construct, the core technology will produce smaller dimension channels that can approach human capillaries and lymphatic to achieve biomimetic properties. By changing the microfluidic layers and/or the semipermeable membranes this core technology will provide an array of different types of microfluidic-based chipset units/modules/modules which are the basic building blocks for constructing different medical devices with much higher efficiency such as many different forms of dialysis, water purification, bioreactors, bio-artificial organ support systems Since each basic unit/module/module is emulating different types of capillaries or lymphatic, the final construct of the desired medical device would be biomimetic. This invention is called Microfluidic-Based Capillaries and Lymphatic Technology (MCAL Technology) which will allow design and development of various biomimetic devices and ultimately replace the 50 year-old inefficient hollow fiber technology currently in use.

Furthermore, these basic units/modules/modules can be used in modular and adjustable fashion and hence it is scalable and can be adjusted to many different and wide-ranging body sizes, various organ support requirements and great deal of related and unrelated medical conditions and illnesses. These basic modules can be connected in parallel and/or in series to design different types of simple and complex medical devices with totally different functions. For example, using Microfluidic-Based Capillaries and Lymphatic Technology (MCAL Technology) and its various microfluidic-chipset basic units/modules/modules in different combinations and permutations several complex medical devices and support systems have been designed which are as follow:

1. Combined microfluidic-based kidney and Liver dialysis device for Multi-organ Dysfunction Syndrome (MODS) and/or Sepsis
2. Mobile, modular and scalable microfluidic-based kidney or liver dialysis systems
3. Microfluidic-based Organ Bio-Reactors for various organ/tissue support systems
4. Bio-Artificial organ support systems (combinations of #3 with either #1 or #2)
5. Microfluidic based on demand Intravenous Fluid and dialysate Generator: For generating ultrapure water from tap water for intravenous use or dialysate use . . . . This will allow to generate different types of i.v. fluids for medical use.

More so, the modular microfluidic basic building block units will be used to construct several different types of highly efficient dialysis systems which can range from portable to small footprint, wearable, adjustable and lightweight hemodialysis device with capability of liver dialysis and kidney dialysis. This devices utilize a plurality of microfluidic units arranged in modular configuration for efficient dialysis of blood or plasma and for dialysate generation or regeneration of spent dialysate; whereby the microfluidic units comprise a blood microfluidic chip and a dialysate microfluidic chip having integrated micro-pumps for continuous pumping of blood and dialysate, microvalves for determining flow direction of the blood and dialysate, and a plurality of micro-channels that emulate the natural microvasculature of the body for optimal flow of blood and dialysate; whereby the blood microfluidic chip and the dialysate microfluidic chip are separated by a semipermeable membrane; whereby a microfluidic dialysis regenerating unit independently regenerates spent dialysate for use by the microfluidic units (Optional).

Furthermore, the present invention relates generally to using combinations and permutations of biomimetically designed microfluidic-based MCAL Technology chipset units to design artificial kidney and/or liver dialysis devices, bio-artificial kidney and/or liver dialysis devices, and on demand i.v. fluids and dialysate generation devices. The present invention relates generally to utilizing various combinations and permutations of these biomimetically designed microfluidic-based MCAL Technology chipset units to design and manufacture a.) a modular microfluidic systems that are designed to do combined kidney and/or liver dialysis system b) microfluidic Bioreactor for organ support systems, and c) combination of a.& b for constructing various Bio-Artificial Dialysis/organ support systems and d) on demand microfluidic i.v. fluid and dialysate generation systems.

The micro-channels designed in the various chipset units (also called modules or modules) that are designed and manufactured based on the MCAL Technology. The biomimetically designed microfluidic-based capillaries and lymphatics chipset units/modules of the MCAL Technology) are configured to emulate the capillaries and/or lymphatics, which are the smallest and most fragile of the body's blood vessels. Those skilled in the art will recognize that the capillaries are responsible for what is known as microcirculation, meaning that they create a circulatory network within the organs of the body. The role of the capillary is to connect the arterioles and the venules. Arterioles are small blood vessels that branch out from arteries, while the venules branch out from veins. Arteries are the vessels that carry clean, nutrient- and oxygen-rich blood from the heart to the remainder of the body. Veins carry the blood back to the heart once the nutrients have been absorbed by the various cells and tissues of the body. Each individual capillary does not work alone, as these vessels form a network in order to carry out their role in the circulatory system.

BACKGROUND OF THE INVENTION

Capillaries are the smallest and most fragile of the body's blood vessels ranging from normally round 3-4 μm, but some capillaries can be 30-40 μmin diameter. They are responsible for what is known as microcirculation—they create a circulatory network within the organs of the body. Each individual capillary does not work alone, as these vessels form a network in order to carry out their role in the circulatory system. They allow the exchange of nutrients and wastes between the blood and the tissue cells, together with the interstitial fluid. This exchange occurs by passive diffusion and by pinocytosis which means 'cell drinking'. Pinocytosis is used for proteins, and some lipids. There are three different types found in the human body: 1) continuous, 2) fenestrated, and 3) sinusoidal. The differences in the various types are due to their location in the body as well as their particular function.

I. Continuous

The endothelial cells provide an uninterrupted lining, and they only allow smaller molecules, such as water and ions to pass through their intercellular clefts.

II. Fenestrated

Fenestrated capillaries allow extensive molecular exchange with the blood such as the small intestine, endocrine glands and the kidney. The 'fenestrations' are pores that will allow larger molecules though. These types of blood vessels are primarily located in the endocrine glands, intestines, pancreas, and glomeruli of kidney.

III. Sinusoidal

Sinusoidal capillaries are special types of open-pore capillary have larger pores (30-40 μmin diameter) in the endothelium. These types of blood vessels allow red and white blood cells (7.5 μm-25 μm diameter) and various serum proteins to pass aided by a discontinuous basal lamina.

Lymphatics:

Similarly, the lymphatic system is a network of tissues and organs that help rid the body of toxins, waste and other unwanted materials. The primary function of the lymphatic system is to transport lymph, a fluid containing infection-fighting white blood cells, throughout the body. Overall, the lymphatic system is part of the circulatory system comprising a network of lymphatic vessels that carry a clear fluid called lymph directionally towards the heart Lymphatic vessels, located throughout the body, are larger than capillaries.

Biomimetic:

Biomimetic is the study of the structure and function of biological systems as models for the design and engineering of materials and machines. Designs formulated using biologically inspired principles will be used to design and develop a biomimetic tissues (i.e. capillaries, lymphatics), and ultimately human organ structures such as (nephron, glomeruli, alveolus) to simulate the biological functions such as filtering and detoxifying clearing of toxins from blood using non-biological or biological (bioengineered) devices.

Recent technological advances have brought a greater understanding of fundamental properties and processes and it has become possible to attempt to 'mimic' or synthesize what nature does naturally. This field, now known as biomimetics, covers many new and emerging topics and offers significant potential in the further development of MEMS, microfluidic devices, and lab-on-a-chip systems. Biomimetic designs can encompass surface treatments that mimic physiological processes or use biological principles to enhance performance through geometric optimization.

One example that could play a significant role in improved flow control through microfluidic devices is mimicking the structure of vascular trees and lymphatics. Biological systems of blood vessels are usually arranged in hierarchical structures and a distinctive feature of this arrangement is their multi-stage division or bifurcation. At each generation, the characteristic dimension of the vascular modules will generally become smaller, both in length and diameter Similar configurations occur in a microfluidic manifold 156 with the inlet channel 158 branching into smaller channels 160 as illustrated schematically in FIG. 8B. It should be noted that this is just one configuration, and these branching can take different forms, topologies and various configurations such as crisscrossing, fractal, curvilinear etc. In addition, the inlet and outlet will have several design including a ledged design to control the distribution hydraulic resistance to be three orders of magnitude lower than the forward flow resistance in the permeation region This means that there will be almost no non-uniformity in the pressure laterally across the permeation region.

Generally, microfluidics is the science of designing, manufacturing, and formulating devices and processes that deal with volumes of fluid on the order of microliters or nanoliters. The microfluidic devices often have dimensions ranging from millimeters down to micrometers. Microfluidic systems have diverse and widespread potential applications. Some examples of systems and processes that might employ this technology include inkjet printers, blood-cell—separation equipment, biochemical assays, chemical synthesis, genetic analysis, drug screening, and mechanical micro-milling. In many instances, the medical industry has shown keen interest in microfluidics technology.

It is known that microfluidics technology is especially useful for heat and mass transfer applications. For the dialysis of blood, or hemodialysis, the purification of blood external to the body, is a process used to treat renal failure. The chemical composition of blood must be controlled to perform its essential functions of bringing nutrients and oxygen to the cells of the body, and carrying waste materials away from those cells. Dialysis replaces some of the kidney's important functions. However, currently there is no efficient liver dialysis available for clinical use toe able to replace many of the important functions of the liver. Generally, dialysis works on the principles of the diffusion and convection of solutes and ultrafiltration of fluid across a semi-permeable membrane.

Generally, blood contains particles of many different sizes and types, including cells, proteins, dissolved ions, and organic waste products. Some of these particles, including proteins such as hemoglobin and albumin, are essential for the body to function properly. Often in dialysis, blood flows by one side of a semi-permeable membrane, and a dialysate, or special dialysis fluid, flows by the opposite side. Smaller solutes and fluid pass through the membrane, but the membrane blocks the passage of larger substances, such as red blood cells, large proteins This replicates the filtering process that takes place in the kidneys, when the blood enters the kidneys and the larger substances are separated from the smaller ones in the glomerulus.

Schematic diagram of a bifurcating vascular network is illustrated in FIG. 4A.

Those skilled in the art will recognize that branching structures found in mammalian circulatory and respiratory systems, minimizes the amount of biological work required to operate and maintain the system. A relationship between the diameter of the parent branching vessel and the optimum diameters of the daughter vessels was first derived by Murray using the principle of minimum work. This relationship is now known as Murray's law and states that the cube of the diameter of a parent vessel (do) equals the sum of the cubes of the diameters of the daughter vessels i.e. $d^3_0 = d^3_1 + d^3_2$ $$d^3_0 = 2d^3_1$$

Biomimetic design principles could play a significant role is mimicking the structure of vascular trees (i.e. glomerular tuft) to improve the flow through microfluidic channels and manifolds. The vessels found in mammalian systems are usually arranged in hierarchical structures and a distinctive feature of this arrangement is their multi-stage division or bifurcation. At each generation, the characteristic dimension of the vascular modules will generally become smaller, both in length and diameter. Similar configurations often occur in microfluidic manifolds with the inlet channel branching into smaller channels.

A generalized form of Murray's law has been developed that can be applied to the design of microfluidic channels and manifolds found in lab-on-a-chip systems. Murray's law was originally developed for cardiovascular systems composed of multi-diameter circular pipes and the present theory has used this biological principle to design constant-depth artificial vascular systems composed of rectangular or trapezoidal cross-sections. Biomimetic principles can now be applied to microfluidic devices fabricated using conventional batch processing techniques. This novel design approach removes the need to fabricate complex, multi-depth microstructures which would otherwise require difficult multi-exposure and alignment steps.

Murray's law was originally derived from biological considerations and its applicability to microfluidic structures is only just being recognized. It has been shown that by carefully selecting the branching parameter governing each bifurcation; it is possible to introduce a prescribed element of control into the flow behavior. For example, hydrodynamic forces may damage shear-sensitive cells and the ability to predict and control a low-shear environment within the network could benefit cell response studies involving free-flowing or anchored cells.

Now this microfluidic technology to generate microvasculature is not a perfect system. After all, different types of microvasculature act more than just delivering the blood to the tissues and organs. The extensive microvasculature is highly involved in many forms of mass transfer which occurs across many forms of capillaries. However, these special properties will be emulated and achieved using various semipermeable membranes with different chemical, physical characteristics and porosities. Hence, when microfluidic technology is used in combination to generate various forms of tissue and organ microvasculatures, they will emulate many types of microvasculature for various medical devices such as specialized dialysis systems, organ/tissue bio-reactors, bio-artificial organ supports and etc.

Microfluidic Capillaries and Lymphatics Technology (MCAL Technology) and its various biomimetically designed microfluidic-based chipset units/modules/segments.

In one embodiment, the special design of a group of microvascular conduits (capillaries & lymphatics) is as follows: The channels of desired shapes with different aspect ratios (width (W), height (H) and length (L)) and various designs and topologies are fabricated on the microfluidic chip utilizing different inert and biocompatible polymers for microfluidic substrates (PDMS, Photo resin, etc.). In addition, double or multilayered microfluidic chips having either different designs or mirror image of each other will be used to sandwich one or multiple types of interchangeable semipermeable membranes separating different layers. It should be noted and emphasized that a permutation of different microfluidic chips with different microchannel structures, shapes and aspect ratios could be used in combination of one or multiple different semipermeable membranes (synthetic, semisynthetic, biocompatible, porous, flux and diverse molecular weight cut-off permeability). This MCAL Technology—core technology—in fact will allow construction of various biomimetically designed microfluidic-based chipset units that act or emulate functions of different capillaries needed for different applications for improvement of human health.

Ultimately, the double or multilayered combination of the microfluidic chips with different channel designs, aspect ratios and semipermeable membranes with different chemical, physical characteristics and porosity will produce many varieties of biomimetic structures that are modular and scalable that could be connected in parallel and/or in series! The permutation of these chipset units will be used to generate so many different types of artificial organ/tissue microvasculature which ultimately be used for production and manufacturing of various medical devices such as specialized dialysis systems, organ bio-reactors, bio-artificial organ supports and etc. that will be used in fields of medical therapeutics, diagnostics and bio-engineering.

Microfluidics enables small dimensions of individual micro-channels 110a-d, which significantly decreases the lateral distance to diffuse through to the exchange semipermeable membrane. As diffusion time scales with the square of the distance, shrinking the lateral dimension just 10 times speeds up the diffusion by a factor of 100. Faster diffusion means more efficient filtration and higher removal percentage even if all other parameters remain the same.

Microfluidics uses photolithography to build very large and dense networks of micro-channels 110a-d with essentially the same ease as making a single channel. This feature allows for a highly efficient network of parallel small channels to be fabricated at low cost. The network combines the fast diffusion with a large increase of surface-to-volume ratio, as the thin sheet device containing the network has the same contact surface area as the traditional device, while having many times smaller volume. This results in a far more efficient device. Furthermore, the use of a large number of small channels allows for individual channel width to remain small enough to avoid mechanical collapse while the channel height is kept very small to allow for fast lateral diffusion. The result is the binary-tree architecture of micro-channels 110a-d as seen in FIG. 8B It is also necessary to emphasize that multiple types of microfluidic chip units 102a-d may be used in parallel and/or in series in the present invention. The followings are the list of the various microfluidic chipset units that are based on MCAL technology. It should be emphasized that each layer of the MCAL Technology Chipset unit/segment/module may contain 1. Blood and its components 2. Plasma/Serum and their components 3. Fluids with different compositions including nutrients or other necessary cell/tissue support elements, growth hormone etc. 4. Different components of tissue/organ, combination of cells, stem cells and other components of organs and tissues 5. Oxygen/air 6. Dialysate and replacement fluids 7. Albumin 8. Activated Charcoal 9. Lipids 10. Resin, ion exchange resin.

In designing the various microfluidic chipset modules, the microchannels may take any shape, topology and configurations. Hence, any form of microchannel design could be used including but not limited to straight, crisscrossing, fractal, curvilinear channels or interrupted channels using pillar design and etc. However, pillar design as opposed to having complete channels is more optimal. The pillar design will allow 1000 micro width for each "channel" and provide a larger fill volume for each chipset. The dimensions of these pillars could range between 10-50 microns however smaller than 20 micron may not release well.

For the purpose of the inflow and outflow design of these various microfluidic chipset modules, a ledged design to control the distribution hydraulic resistance to be three orders of magnitude lower than the forward flow resistance in the permeation region. This means that there will be almost no non-uniformity in the pressure laterally across the permeation region.

In addition, each and every microfluidic chipset unit/segment/module that is manufactured based on the MCAL Technology will have the options of integrated heating and cooling elements and the heatsink if needed and are optional.

The most outer layers on each side of the module are heatsinks. The TEC only pumps heat and for cooling the module down, a heatsink is placed to dissipate energy. To heat up the module, the heatsinks capture the energy.

One microfluidic MCAL Technology module may have any or all the 7 layers:

For the purpose of the inflow and outflow design of these various microfluidic chipset modules, a ledged design to control the distribution hydraulic resistance to be three orders of magnitude lower than the forward flow resistance in the permeation region. This means that there will be almost no non-uniformity in the pressure laterally across the permeation region.

In addition, each and every microfluidic chipset unit/segment/module that is manufactured based on the MCAL Technology will have the options of integrated heating and cooling elements and the heatsink if needed and are optional.

The heating element is a TEC (Peltier device). The copper plates are utilized to transfer the heat and cold uniformly to the MCAL Module. Utilizing the TEC, the various modules have the capacity to perform at one, elevated temperature, or even generate a temperature gradient across the chipset/membrane to motivate faster permeation, diffusion and convection and etc.

The most outer layers on each side of the module are heatsinks. The TEC only pumps heat and for cooling the module down, a heatsink is placed to dissipate energy. To heat up the module, the heatsinks capture the energy.

One microfluidic MCAL Technology module may have any or all the 7 layers:
1. Heatsink
2. The Cooper layer
3. The TEC (Peltier device)
4. The Microfluidic Chipset Unit
5. The TEC (Peltier device)
6. The Copper Layer
7. Heatsink Furthermore, in another design, the heating and cooling could be built external to the chipset modules as well. Also a couple or more adjacent modules may share some of the components of heating cooling system.

Another optional feature of these MCAL Modules is the capacity to have micro-vibration assembled on each modules and/or a group of modules to have their own dedicated micro vibration unit.

This innovative and proprietary MCAL Technology has the following benefits which sets it apart from other. These are the followings:

Emulating different vasculatures (capillaries, lymphatics)
Faster Diffusion & Convection
Higher Efficiency
Higher Surface Area (SA) to Volume (V) Ratio (SAN)
Higher Clearances for Important Uremic Toxins
Scalable/From a Smaller Units/modules to a Larger Ones
Can be connected in Series or Parallel or in Combination
Multilayer with each layer acting either as a lymphatic or different type of capillary
Modular & Adjustable
Variable Angled cross flow/Countercurrent Flow
Variable aspect ratios ranging from 10 um to 2 mm
Can be used in many different applications This list includes 18 basic units/modules/segments but is not limited to only these configurations. It should be noted that the microfluidic modules beyond a 2-layered design may have a combination of many of these various semipermeable membranes with wide-ranging chemical, physical characteristics as well as porosities. The Bio-Reactor Module—the BR Module—is just an example of this combination of different membranes in a multilayer module design.

1. The HD Chipset (Hemodialysis Function) in formation of this module, any type of high flux or low flux hemodialysis membranes will be used.
2. The UF Chipset (Ultrafiltration Function) in formation of this any type of ultrafiltration membranes will be used.
3. The PS Chipset (Plasma Separation/plasmapheresis) in formation of this any type of plasmapheresis/plasma separation membranes will be used.
4. The HP Chipset (Hemoperfusion) in formation of this any type of hemoperfusion will be used.
5. The AD Chipset (Albumin Dialysis) in formation of this any type of HMWCO membranes will be used.
6. The D Chipset (Diafiltration) in formation of this any type of CRRT membranes will be used.
7. The HDF Chipset (Hemodiafiltration) in formation of this any types of CRRT membranes will be used.
8. The DR Chipset (Dialysis Regeneration) in formation of this a combination of resin, activated charcoal, zirconium etc. will be used.
9. The O Chipset (Oxygenation) in formation of this any type of ECMO membrane will be used.
10. The HD Chipset (Hemodialysis/High Efficiency) in formation of this any type of high efficiency hemodialysis membranes will be used.
11. The ADR Chipset (Albumin Dialysis and Regeneration) in formation of this combination of any type of HMWCO membranes with a combination of resin, activated charcoal, zirconium etc. will be used.
12. The BR (Bio-Reactor Chipset—Tissue Support using HMWCO Membrane) in formation of this combinations of any type of ECMO membrane with all other semipermeable membranes including HMWCO membranes in a multilayered modules.
13. The RO (the reverse Osmosis) in formation of this any type of reverse osmosis membranes will be used.
14. The FO (Forward Osmosis) in formation of this any type of forward osmosis membrane will be used.
15. The EDI (Electrodeionization) in formation of this any type of ion exchange membranes and resins will be used.
16. The ED (Electrodialysis) in formation of this type of ion-exchange membranes in combination with an applied electric potential difference. Electrodialysis (ED) is used to transport salt ions from one solution through ion-exchange membranes to another solution under the influence of an applied electric potential difference. This is done in a configuration called an electro-dialysis cell.
17. The EF (Electrofiltration) in formation of this any type of membrane filtration and electrophoresis process will be used. Electrofiltration is a method that combines membrane filtration and electrophoresis in a dead-end process.
18. The LD (Lipid Dialysis) in formation of this any type of membranes to dialyze against any inert and biocompatible lipid solutions will be used.

Each Chipset module is designed to emulate some of the function of human capillaries or lymphatic (though not exactly and precisely). Each basic chipset module which utilizes a specific or various semipermeable membranes to allow manipulation of blood, blood components, plasma, water, electrolytes, nitrogenous waste, amino acids, albumin, globulins, hormones and enzymes, nitrogenous waste, nutrients, and gases.

Different Types of Applications for the Microfluidic-based Capillaries and Lymphatic Technology (MCAL Technology) and its various biomimetically designed microfluidic-based chipset units mentioned above.

1. Combined microfluidic based kidney and Liver dialysis device for MODS and/or Sepsis
2. Mobile, modular and scalable kidney and/or liver dialysis systems
3. Microfluidic based Bio-Reactors for various organ/tissue support systems
4. Bio-Artificial organ support systems (combinations of #3 with #1 or #2)
5. Microfluidic based on demand Intravenous Fluid and dialysate Generator: For generating ultrapure water from tap water for intravenous use or dialysate use . . . . This will allow to generate different types of i.v. fluids for medical use.

Combined Microfluidic Based Kidney and Liver Dialysis Device for Liver Failure and Multi-Organ Dysfunction Syndrome (MODS) and/or Sepsis This is the design for a modular and scalable combined kidney and liver dialysis device that is based on the MCAL Technology. This highly efficient dialysis device will replace the inefficient hollow Fiber Technology currently in clinical use. This device is termed combined microfluidic based kidney and Liver dialysis device using combination of the MCAL Technology core technology building-block units a modular microfluidic dialysis system can be designed which provides a hemodialysis device to perform both kidney and liver dialysis needed in liver failure and also multiorgan failure in MODS and sepsis.

The currently available dialysis devices essentially only eliminate water-soluble substances of low or intermediate molecular weight, hence they are very inefficient.

These standard dialysis based processes do not achieve sufficient removal of uremic toxins (the middle molecules) as well as the notorious protein-bound substances.

In addition, currently, there is no liver dialysis system to provide clearance of tightly bound hepatic toxins accumulated during liver failure.

Therefore, for acute liver failure or an acute exacerbation of chronic liver failure (acute on chronic liver failure) regular dialysis modalities are not sufficient.

However, in this unique combined microfluidic based kidney and Liver dialysis device a combination of the known dialysis processes (diffusive, convective as well as adsorptive, CRRT, Hemodialysis, hemodiafiltration, hemoperfusion, albumin dialysis and novel and unique lipid dialysis)) with "special" maneuvers that manipulate the blood, plasma (utilizing plasma separation/plasmapheresis membranes technology), which will increase the efficiency of standard dialysis plus ultimately increasing the free serum concentration of "protein-bound toxins" could effectively improve the inefficiency of dialysis for kidney or liver as well as Kidney and Liver. Simply put, this is the basis for the combined microfluidic based kidney and Liver dialysis device.

It is important to note that the fashion that these membranes and filters are placed together and their permutation are part of this patent.

The Combined microfluidic-based kidney and Liver dialysis device can be made in a compact form to be used for many different types of Multi-System/Multi-Organ Dysfunctions associated with liver and kidney failure such as:

Acute on Chronic Liver Failure (ACLF)
ALF (Acute Liver Failure)+AKI or CKD
CLF (Chronic Liver Failure)+AKI+CKD
AKI
Sepsis
MODS Combined microfluidic based kidney and Liver dialysis device utilizes the following mechanisms to increase efficiency of kidney dialysis as well a liver toxin removal:

Reducing Recirculation (use of two accesses, each in a different limb, to decrease recirculation entirely)
Reducing the blood flow and blood volume required for optimal dialysis
Reducing dead-space (After plasmapheresis mostly the plasma is occupying the precious membrane surface area that is so crucial for the more efficient dialysis processes.)
Increasing the convective dialysis by increasing
  a. Ultrafiltration
  b. Internal filtration
Increasing the free serum concentration of the protein-bound toxins via dilution with Specialized Replacement Fluids to favor the equilibrium towards higher serum concentration of the non-bound toxins
  c. Example. 1:4 dilution and subsequently a 1:4 dilution via replacement fluids will yield a 1:16 dilution of the free toxins which will force the change in equilibrium
Certain chemicals can change the equilibrium as well as the temperature
Use of albumin for albumin dialysis
Use of novel lipid dialysis (optional)
Using combination of Albumin with/without Charcoal and Resins for a specialized albumin based dialysis and specialized dialysate This device utilizes a plurality of various microfluidic-based chipset units/modules/segments—based on MCAL Technology—that are arranged in modular configuration for efficient dialysis of blood and dialysate; whereby the microfluidic device comprise of various modules, having integrated micro-pumps for continuous pumping of blood and dialysate, micro-valves for determining flow direction of the blood and dialysate, and a plurality of biomimetically designed micro-channels that emulate the natural microvasculature of the body for optimal flow of blood and dialysate, whereby a microfluidic dialysate regenerating unit/module (DR Module) independently regenerates spent dialysate for use by the microfluidic units (optional).

Those skilled in the art will recognize that the loss of kidney function results in the accumulation of many metabolites, some of which have been identified and their toxic effects on cell metabolism elucidated. These toxins fall under the two categories of 1. Middle molecular weight uremic toxins and 2. Small solutes that are highly protein bound and are difficult to remove from the blood via regular diffusive dialysis. These are the protein-bound uremic toxins Over a hundred of such uremic toxins have been identified, and their removals by various modalities of renal and liver replacement therapy have been studied.

Liver function is regularly divided into two major categories: 1. Synthesis and 2 Toxin removal. The liver synthesizes many of the essential proteins for body function. In addition liver is an active organ in metabolism of many toxins and their removal. The only current therapy to return the hepatic synthetic function is only liver transplantation. Liver transplantations are performed on less than 25% of patients with acute liver failure because no adequate process for taking over the detoxification function exists, so the time taken for the hepatic function to recover cannot be bridged.

Uremic and hepatic toxins are accumulated in a number of diseases related to the kidney and liver diseases respectively. The major difference between the uremic and hepatic toxins is that majority of the hepatic toxins are protein-bound complexes, hence not easily dialyzable. Therefore, for acute liver failure or an acute exacerbation of chronic liver failure (acute on chronic liver failure) regular dialysis modalities are not sufficient.

Hepatic toxins associated with liver failure vary with respect to molecular size and physicochemical characteristics. Typically, a significant proportion of toxins are albumin-bound (e.g. bilirubin, bile acids, and hydrophobic amino and fatty acids). There is growing evidence suggesting an important role of these toxins in the development and maintenance of multi-organ failure subsequent to hepatic failure. Another significant proportion of toxins comprise water-soluble toxins of low- and middle-molecular weight. They are derived either from hepatic failure (e.g. ammonia), or renal dysfunction and are efficiently removed by either hemodialysis or hemofiltration. To date, however, conventional methods failed to remove of albumin-bound toxins effectively.

Other proposals have involved dialysis systems for the liver dialysis which currently is non-existence and for improvement of kidney dialysis adequacy. In addition to limited efficiency, they only provide marginal and partial removal of middle molecular weight toxins Thus, there are great unmet needs exist in the industry to address the aforementioned deficiencies and inadequacies.

The general design of the Combined microfluidic-based kidney and Liver dialysis device is utilizing the MCAL Technology—the various Core Technology microfluidic chipset units/modules in different combinations and permutations. This novel dialysis device will have several different components comprise of the modular and scalable basic microfluidic chipset units/modules that are connected in parallel and/or in series either on or off one or multiple microfluidic chips to design and develop the desired devices. It should be noted that in order to improve the efficiency of this unique microfluidic based dialysis device, the arterial and venous ports are separated and are placed on opposite limbs to decrease the recirculation rate close to zero.

The blood from the patient is pumped through a single lumen catheter (the arterial line of the dialyzer), and then is anticoagulated (if needed) before entering the first module of the combined microfluidic based kidney and Liver dialysis device.

The components of the combined microfluidic-based kidney and Liver dialysis device are as follows:
1. PS module/unit (plasma separation)
2. HD module/unit (Hemodialysis)
3. HP module/unit (Hemoperfusion)
4. HDF or DF module/unit (Hemodiafiltration) or (Diafiltration)
5. AD module (Albumin Dialysis)
6. ADR module (Optional Regeneration of Albumin Dialysate)
7. DR module (Optional Dialysate regeneration)
8. LD module (Optional Lipid Dialysis)

Note: The device can either initially performs
1. A regular hemodialysis or hemodiafiltration plus replacement fluid on the whole blood and then perform the plasmapheresis to generate plasma portion for further manipulation and dialysis.

2. Perform a plasmapheresis generate a plasma portion then perform a regular hemodialysis and/or hemodiafiltration etc. on the plasma portion.

The Cellular portion from the plasmapheresis will be returned to patient immediately or go through a regular dialysis additionally (optional).

The PS Module—This module is designed to emulate some of the function of a glomerulus in human nephron, (though not exactly and precisely). The G module which utilizes the plasmapheresis membrane will allow plasma Water, Albumin, Globulins, Amino acids, Hormones and Enzymes, Nitrogenous waste, Nutrients, Gases and Fibrinogen to be filtered Therefore, the PS module will filter all non-cellular components of the whole blood and generate two portions.

One portion is the portion containing mostly the cellular elements of the blood (WBCs, RBCs and Platelets) and some plasma. This is called Cell Portion (CP).

The other portion is the portion containing non-cellular components of the whole blood (all proteins, electrolytes, and albumin). This is called the plasma portion (PP).

The CP will be directed back to the patient (BTP), while the PP portion enters the next module of the dialysis apparatus to be dialyzed and cleaned.

The HD module—This module is designed to emulate partial clearance of glomerulus and tubules.

The PP will be diluted 1:1 to 1:4 ratios by an isotonic replacement fluid (RF) using a reservoir that contains fresh unused RF. This 1:1 to 1:4 (Plasma: RF) dilutions drastically reduces the albumin and protein concentration of the PP hence increasing the free plasma portion of protein and albumin-bound toxins. In addition the dilution reduces the risk of coagulation and hence the need for anticoagulation.

The HDF Module—This module is designed to emulate the filtration function of the glomerulus in the human nephron. The diluted PP enters the HDF module which utilizes hemodiafiltration membrane and undergoes a good diffusive and convective dialysis in addition to an intensive internal filtration due to increased length of the fiber/channel as well as decreased diameter of the fiber/channel. Of course a dialysate is used during this process which will be regenerated through the DR module. The PP which is well dialyzed is directed to the next module of the dialysis device. (Option/to save dialysate using the back filtration we regenerated some due to reduced filtration).

The HP Module—This module is designed to imitate the function of the tubule portion of human nephron. The well dialyzed PP now enters the HP module which utilizes a hemoperfusion procedure using a suspension of charcoal and resin. PP will be hemoperfused against the fresh resin and charcoal. The PP is further cleared from protein-bound toxins. The PP is again diluted I: to I:4 using fresh isotonic replacement fluid before entering the next module.

The AD Module—This module is designed to imitate another function of the tubule portion of the human nephron. The PP enters the AD module which utilizes a high performance membrane with very High-Molecular-Weight Cut-Off (HMWCO) characteristic to perform an Albumin Dialysis. The PP will be dialyzed against a reservoir of fresh albumin or a combination of albumin plus charcoal/resin. This reservoir will be regenerated to remove the captured protein-bound toxins and avoid saturation of albumin binding. The PP is returned via a separate line using a single lumen catheter to the patient via the opposite limb as explained above.

The DR Module—This module is designed to regenerate the spent dialysate using a reservoir of charcoal and resin.

The spent dialysis is run through the suspension of charcoal and resin and other substances to regenerate the dialysate. The regenerated dialysate is returned to the required modules as needed. Option: this regeneration can be eliminated and dialysate fresh can be used without regenerating it.

The ADR module—this module is designed to regenerate the spent albumin.

The MCAL Technology module ADR (Albumin Dialysis Regeneration)

A multilayered PDMS based Microfluidic Chipset for more efficient albumin dialysis A multilayered PDMS microfluidic chipset is designed for performing much more efficient albumin dialysis and removal of the protein/albumin-bound toxins. This chip design is unique since the albumin regeneration is built on the chip.

A multilayered PDMS based microfluidic chipset. At least a single layer of PDMS for blood compartment (blood layer) sandwiched between two two-layered charcoal and albumin dialysate layers placed in mirror image.

Between each of the following layers, the $1^{st}$ & $2^{nd}$, $2^{nd}$ & $3^{rd}$, $3^{rd}$ & $4^{th}$ and $4^{th}$ & $5^{th}$ layers, a high flux membrane (or other semipermeable membranes) will be placed to separate each layer compartment and provide the surface for dialysis to occur.

Note: All fluids flow in a countercurrent direction respect to their adjacent layers The concurrent, countercurrent as well as tangential cross flows may be used for best and optimal efficiency The membranes used can vary but high flux or even membranes with higher MWCO characteristics may be utilized. In addition, the rate of flow for each layer will be studied and optimized.

The diluted and well dialyzed PP enters this module—the A module which emulates the function of the tubule portion of the human nephron. The diluted PP enters the A module where Albumin dialysis is performed using High-Molecular-Weight Cut-off (HMWCO) membrane/High Performance Membrane which allows the PP to be dialyzed against albumin or a combination of albumin plus charcoal/resin. The first output of the MCAL Technology—the PP portion—will be directed back to the patient/subject while the second output of this module—the spent albumin dialysate—will be directed to the module DR for regeneration.

The RO Module—This module is designed to emulate the function of the collecting tubule portion of the human nephron. The spent dialysate plus ultrafiltration will enter the RO module which utilizes a reverse osmosis membrane to extract the water and the rest is discarded as urine like material. The water is then used for other functions in the device.

The present invention is directed to a modular and scalable microfluidic unit that each that utilizes different and various principles of microfluidics for performing different processes on blood and plasma. These processes includes but not limited to filtration, ultrafiltration, diafiltration, various forms of dialysis, hemoperfusion, plasma separation and etc. of any fluid, such as blood, plasma and lymph. The modular microfluidic dialysis system provides a portable, wearable hemodialysis device that helps remove middle molecular weight uremic toxins, small solutes, hepatic toxins, water, and other impurities from the blood through the use of microfluidic technology. The microfluidic dialysis system provides particular advantages in blood dialysis for mobile kidney augmentation devices, liver treatment, and fabrication of an artificial kidney.

In one embodiment, the system utilizes various micro-components that emulate the physiological parameters of the body. These micro-components provide numerous advantageous over traditional dialysis, such as hollow tube filtration and reverse osmosis. In this manner, the middle molecular weight uremic toxins and small solutes may be filtered out of the blood more efficiently. Furthermore, the system is modular, so as to enable scalability and conformance to different body types and requirements.

In some embodiments, the system may utilize a portable, lightweight, and wearable hemodialysis device. The device is battery operated. The device utilizes tubing to connect to the patient and to a disposable cassette that contains the means for processing the blood and dialysate. A simple user interface enables operation of the device and monitoring of blood temperature and pressure. A data transmission portion, such as a Wi-Fi transmitter, enables real time monitoring of physiological parameters of the body and mechanical parameters of the system.

In one aspect, a modular microfluidic dialysis system, comprises:
  a plurality of microfluidic units, the plurality of microfluidic units configured to enable any one of different forms of blood filtration, ultrafiltration, diafiltration, plasma separation and dialysis of blood, the plurality of microfluidic basic building block units can be arranged in modular configuration in parallel or in series for enabling scalability, the plurality of microfluidic units at least partially fabricated from inert and biocompatible polymers commonly used in microfluidic such as a polymeric organosilicon compound, the plurality of microfluidic units comprising:
    a blood microfluidic chip and a dialysate microfluidic chip, the blood microfluidic chip configured to carry blood, the dialysate microfluidic chip configured to carry a dialysate,
    the blood microfluidic chip and the dialysate microfluidic chip comprising a plurality of micro-pumps, the plurality of micro-pumps configured to pump the blood to and from the blood microfluidic chip, the plurality of micro-pumps further configured to pump the dialysate to and from the dialysate microfluidic chip,
    the blood microfluidic chip and the dialysate microfluidic chip further comprising a plurality of micro-valves, the plurality of micro-valves configured to regulate the flow of the blood and the dialysate,
    the blood microfluidic chip and the dialysate microfluidic chip further comprising
    a plurality of micro-channels, the plurality of micro-channels configured to carry the blood to and from the blood microfluidic chip, the plurality of micro-channels further configured to carry the dialysate to and from the dialysate microfluidic chip, the plurality of micro-channels defined by multiple widths and topographies; and
    a semipermeable membrane, the semipermeable membrane disposed between the blood microfluidic chip and the dialysate microfluidic chip, the semipermeable membrane configured to form a permeable barrier between the blood and the dialysate, the semipermeable membrane further configured to enable passage of toxins and water from the blood in the blood microfluidic chip to the dialysate in the dialysate microfluidic chip; and
    a microfluidic regenerating unit, the microfluidic regenerating unit configured to at least partially filter contaminated dialysate received from the dialysate microfluidic chip, the microfluidic regenerating unit further configured to return regenerated dialysate to the dialysate microfluidic chip.

In a second aspect, the polymeric organosilicon compound is PDMS.

In another aspect, the plurality of micro-pumps comprises electric micro-pumps and pneumatic micro-pumps.

In another aspect, the plurality of micro-pumps comprises two blood micro-pumps, a heparin micro-pump, an ultrafiltration micro-pump, and a dialysate micro-pump.

In yet another aspect, the plurality of micro-channels have a wide inlet, a narrow median region, and a narrow outlet.

In yet another aspect, the plurality of micro-channels has a wide inlet, a narrow median region, and a wide outlet or a combination of these characteristics.

In yet another aspect, the plurality of micro-channels is configured in substantially the same or different topography and width as a microvasculature of thebody.

In yet another aspect, the plurality of micro-channels have a wide raging width of about 100-2000 microns, a depth of about between 10 to 100 microns, and a length of about between 1 to 20 centimeters.

In yet another aspect, the topography of the plurality of micro-channels includes at least one member selected from the group consisting of: straight, parallel, crisscross, fractal pattern, loops, and branched.

In yet another aspect, the dialysate is an ultrapure dialysate

In yet another aspect, the microfluidic regenerating unit includes at least one member selected from the group consisting of: a sediment filter, a carbon filter, a zirconium carbonate filter, a deionizing resin, a micro-filter, an ultraviolet light, 0.22 micron filter, and a cold plasma regeneration apparatus.

In yet another aspect, the microfluidic regenerating unit is configured to regenerate between 300 milliliters to 1500 milliliters of dialysate.

In yet another aspect, the microfluidic dialysis regenerating unit comprises a slot, the slot configured to receive a vial of the dialysate.

In yet another aspect, the microfluidic regenerating unit comprises dimensions of about 20 centimeters in length by 10 centimeters in width by 10 centimeters in height.

In yet another aspect, the system further comprises one or several warming devices, the warming device configured to activate charcoal and other optional sections.

In yet another aspect, the system further comprises one or more cooling devices.

In yet another aspect, the system further comprises a data transmission portion, the data transmission portion configured to enable real time monitoring of physiological parameters of the body and mechanical parameters of the system.

In yet another aspect, the data transmission portion comprises a Wi-Fi transmitter.

In yet another aspect, the modular configuration of the system is configured such that about 10-100 microfluidic units form a microfluidic construct.

In yet another aspect, the modular configuration of the system is configured such that about 5-20 microfluidic constructs form a microfluidic module.

In yet another aspect, the microfluidic module positions inside microfluidic housing In yet another aspect, the plurality of micro-valves are configured to close if the microfluidic module is not disposed in an operable orientation inside themicrofluidic housing.

In one embodiment, the device comprises a plurality of microfluidic units that receive, filter, and return the blood and dialysate to the body and dialysate reservoir, respectively. The microfluidic units are arranged in modular configuration for enhanced scalability, such that the microfluidic units can be added, removed, or rearranged to conform to the dialysis needs of the patient. This allows for more efficient dialysis of the blood.

The multilayered microfluidic units comprise one or multiple blood microfluidic chips, two or more dialysate microfluidic chips, and one or more semipermeable membranes having different characteristics disposed between the chips. The two or more chips (membranes, filters, etc) have substantially the same configuration, i.e., mirror images of each other, though various configurations can be used as needed. In one embodiment, all the blood microfluidic chips and all the dialysate microfluidic chips comprise integrated micro-pumps for pumping blood and dialysate continuously. This minimizes the need for excessive quantities of dialysate. The chips further comprise micro-valves for determining flow direction. The micro-valves remain closed if the chips are not properly aligned.

The chips further comprise a plurality of micro-channels for carrying the blood and dialysate to the appropriate chip. The micro-channels are configured to emulate the natural microvasculature of the body, i.e., capillaries, arterioles, venules and lymphatics. In one embodiment, the micro-channels include a narrow channel having different topologies and widths for optimal flow of blood and dialysate. This unique configuration of the micro-channels creates fluid shear rates that are amenable to red blood cells contained in blood. The micro-channels have substantially smaller diameters than the current hollow fiber technology; thereby enabling more efficient diffusive and convective fluid flow.

The micro-pumps, micro-valves, and micro-channels are fabricated directly on the respective chip. The micro-pumps, micro-valves, and micro-channels are also fabricated from inert and biocompatible polymers like a polymeric organosilicon compound, such as PolyDiMethylSiloxane (PDMS). Those skilled in the art will recognize that PDMS provides numerous advantageous for microfluidics, including: unique rheological properties for enhanced blood and dialysate flow, transparency for viewing the blood and dialysate, deformability for forming desired micro-channel configurations, sticking properties for adhering to other PDMS components, and non-toxicity.

The blood microfluidic chip and the dialysate microfluidic chip sandwich a semipermeable membrane that provides the filtering capacity for the dialysis. The semipermeable membrane is configured to form a permeable barrier between the blood and the dialysate. In this manner, the semipermeable membrane enables passage of toxins, water, and small electrolytes from the blood in the blood microfluidic chip to the dialysate in the dialysate microfluidic chip. In one embodiment, the semipermeable membrane allows only water and small electrolytes to pass.

The device further includes a microfluidic dialysis regenerating unit that independently regenerates spent dialysate for use by the dialysate microfluidic chip. By regenerating the dialysate, a minimal amount of dialysate is required for operation of the device. In one exemplary use, the microfluidic regenerating unit is configured to regenerate between 300 milliliters to 1500 milliliters of the dialysate.

The microfluidic dialysis regenerating unit utilizes various sediment filters, carbon filters, deionizing resin, micro-filters, and optional ultraviolet lights and/or cold plasma technology for sterilization and 0.22-micron filter to generate an ultrapure dialysate regeneration unit (Optional). The microfluidic dialysis regenerating unit negates the need for reverse osmosis filtering techniques. The microfluidic dialysis regenerating unit further comprises a slot for receiving a vial of dialysate. In one embodiment, a plurality of microfluidic dialysis regenerating units fit into a regenerating unit housing.

In some embodiments, the system is modular to enable scalability, adjustability and adaptability for accommodating different types of patients with various sizes, accumulated toxin types in the blood (hepatic vs. uremic toxins), medical conditions, support requirement and dialysate requirements. The two or multilayered blood microfluidic chip(s), the dialysate microfluidic chip(s), and the semipermeable membrane(s) sandwiched there between forms various microfluidic units. About 10-100 microfluidic units form a microfluidic construct. About 5-20 microfluidic constructs form a microfluidic module. The microfluidic module positions inside a microfluidic housing. In one embodiment, the microfluidic module must be aligned properly inside the microfluidic housing before the micro-valves open.

One objective of the present invention is to utilize MCAL technology basic building blocks and micro-channels having microvasculature characteristics for performing dialysis.

Another objective is to provide a hemodialysis device that is portable, wearable, light-weight and easy to use, and patient friendly.

Another objective is to provide a microfluidic-based dialysis system that removes middle molecular weight uremic toxins, small solutes and/or protein-bound toxins.

Another objective is to regulate extracellular fluid volume and blood pressure control, electrolyte, acid base control, and correction of anemia.

Yet another objective is to fabricate the micro-channels from a polymeric organosilicon compound, such as PDMS, that has unique rheological properties that enhance flow of blood and dialysate, is transparent, sticks to other micro-channels and the respective chip, is deformable, and non-toxic.

Yet another objective is to create a scalable configuration that enables adding, removing, and rearranging microfluidic modules from the microfluidic housing.

Yet another objective is to provide a microfluidic regenerating unit to replace reverse osmosis functions and components.

Yet another objective is to incorporate the microfluidic housing and the regenerating unit housing in a disposable cassette.

Yet another objective is to enable real time monitoring of the physiological aspects of the blood and body parts, and the mechanical components of the system.

Yet another objective is to provide a dialysis system that can operate continuously or intermittently, operating from 2-24 hours/day seven days a week.

Yet another objective is to enable gentle ultrafiltration to avoid severe post-dialysis fatigue and fluid shifts seen by regular dialysis methods.

Yet another objective is to regenerate dialysate fluid to minimize the amount of dialysate used daily to as little as 300 ml/day to 1500 ml/day.

Yet another objective is to provide cost effective dialysis for treatment of liver and/or kidney failures.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which:

FIG. 4A illustrates a blood microfluidic chip, a semipermeable membrane, and a dialysate microfluidic chip separated, and FIG. 4B illustrates the fully operational microfluidic unit, in accordance with an embodiment of the present invention;

FIG. 8A illustrates sectioned side view of a plurality of micro-channels in a microfluidic unit, and FIG. 8B illustrates microfluidic manifolds with the inlet micro-channel branching into smaller micro-channels, in accordance with an embodiment of the present invention;

FIG. 10 illustrates a comparison Table 162 that differentiates the Hollow Fiber Technology and MFC technology, in accordance with an embodiment of the present invention;

FIGS. 11A and 11B illustrate perspective top angle views of micro-channels fabricated directly on a blood microfluidic chip, where FIG. 11A illustrates the micro-channels, and FIG. 7 illustrates dialysate flowing through the micro-channels, in accordance with an embodiment of the present invention;

FIG. 12A illustrates straight micro-channels, FIG. 12B illustrates parallel micro-channels about one hundred microns wide, and FIG. 12C illustrates branched micro-channels, as used in a bio-artificial liver, in accordance with an embodiment of the present invention;

FIG. 18 illustrates two diagrams of a 5-layered inert and biocompatible polymer used as microfluidic substrate such as PDMS based microfluidic chipset module.

FIG. 19 illustrates a few simple devices schematically presented to show development of three different yet similar Dialysis/support devices.

FIG. 20 illustrates two diagrams of a 5-layered PDMS based microfluidic chipset.

FIG. 21 illustrates a diagram of a multilayered microfluidic chipset unit/module with a single layer of microfluidic micro-channels for blood/plasma compartment (blood layer) sandwiched between two albumin dialysate layers placed in mirror image.

FIG. 22 illustrates a diagram of a 3-layered inert and biocompatible polymer used as microfluidic substrate such PDMS based microfluidic chipset.

FIG. 23 illustrates a diagram of utilizing the various biomimetically designed microfluidic-based MCAL Technology microfluidic chipset units in the following ways.

Like reference numerals refer to like parts throughout the various views of the drawings.

DETAILED DESCRIPTION OF THE INVENTION

Figure 1:
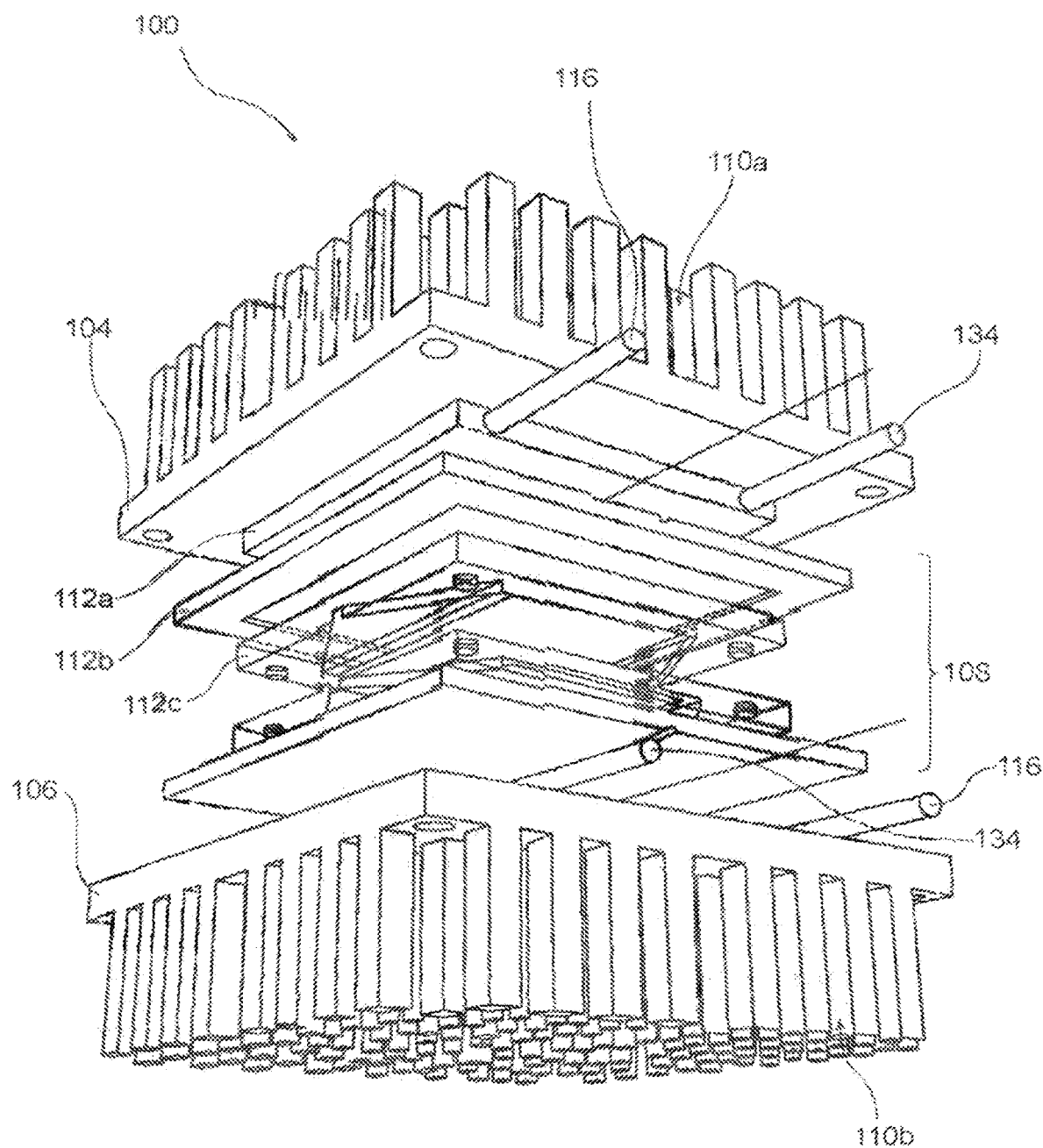
FIG. 1 illustrates a perspective view of an exemplary modular microfluidic dialysis system, in an expanded position, in accordance with an embodiment of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "first," "second," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

At the outset, it should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" of this invention as required by 35 U.S.C. § 112.

Combined Microfluidic-Based Kidney and Liver Dialysis Device for MODS and/or Sepsis In one embodiment of the present invention presented in FIGS. 1-17, a modular microfluidic dialysis system 100 provides a portable, wearable hemodialysis device that helps remove middle molecular weight uremic toxins and small solutes, hepatic toxins, water, and other impurities from the blood 134 through the use of microfluidic technology. The modular microfluidic dialysis system 100, hereafter, "system 100" utilizes principles of microfluidics for filtering a fluid, such as blood 134 and lymph. The system 100 provides particular advantages in blood 134 dialysis for mobile kidney augmentation devices, liver treatment, and fabrication of an artificial kidney.

Figure 2:
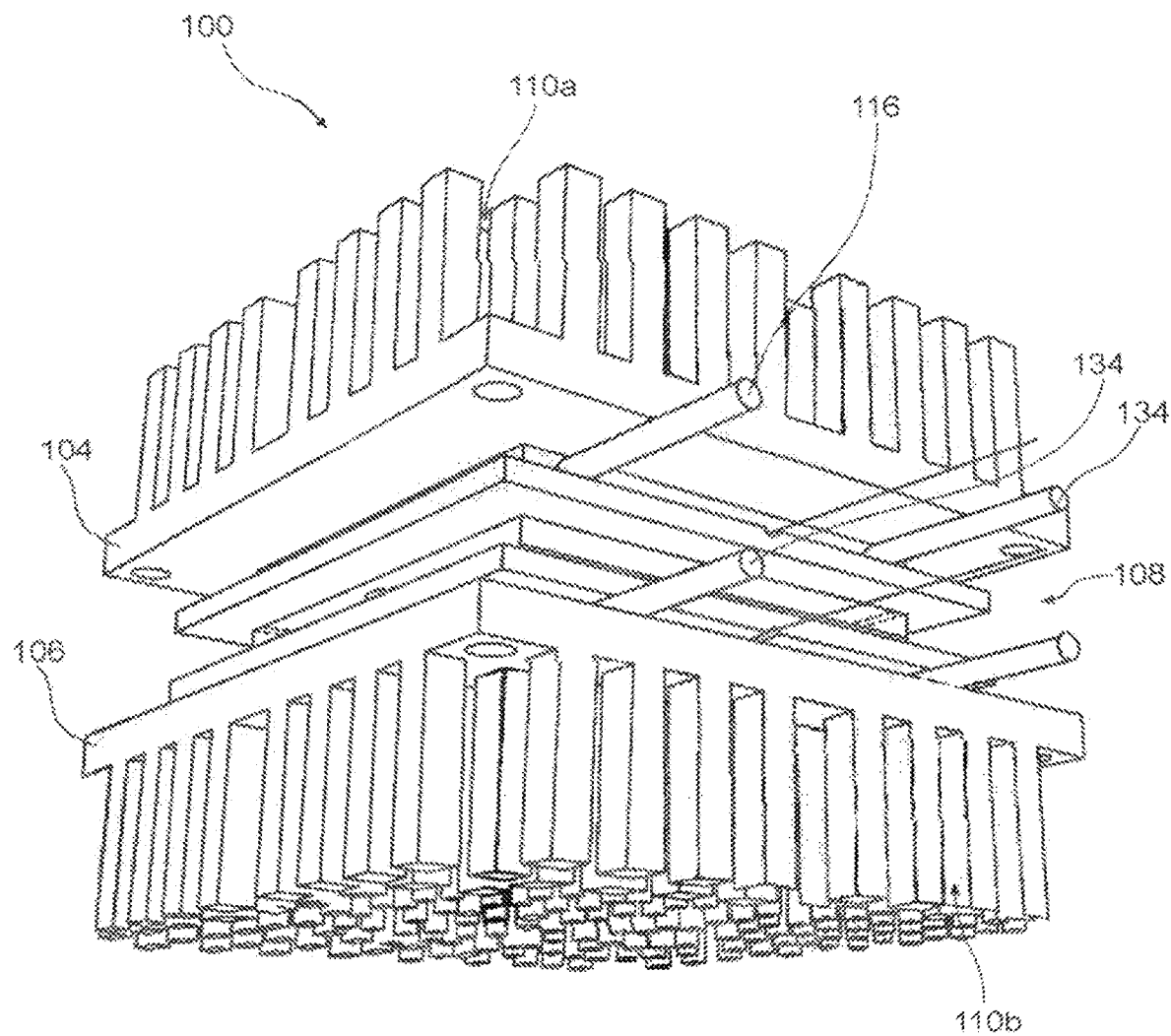
FIG. 2 illustrates a perspective view of a modular microfluidic dialysis system, in a compressed position, in accordance with an embodiment of the present invention.
Figure 3:
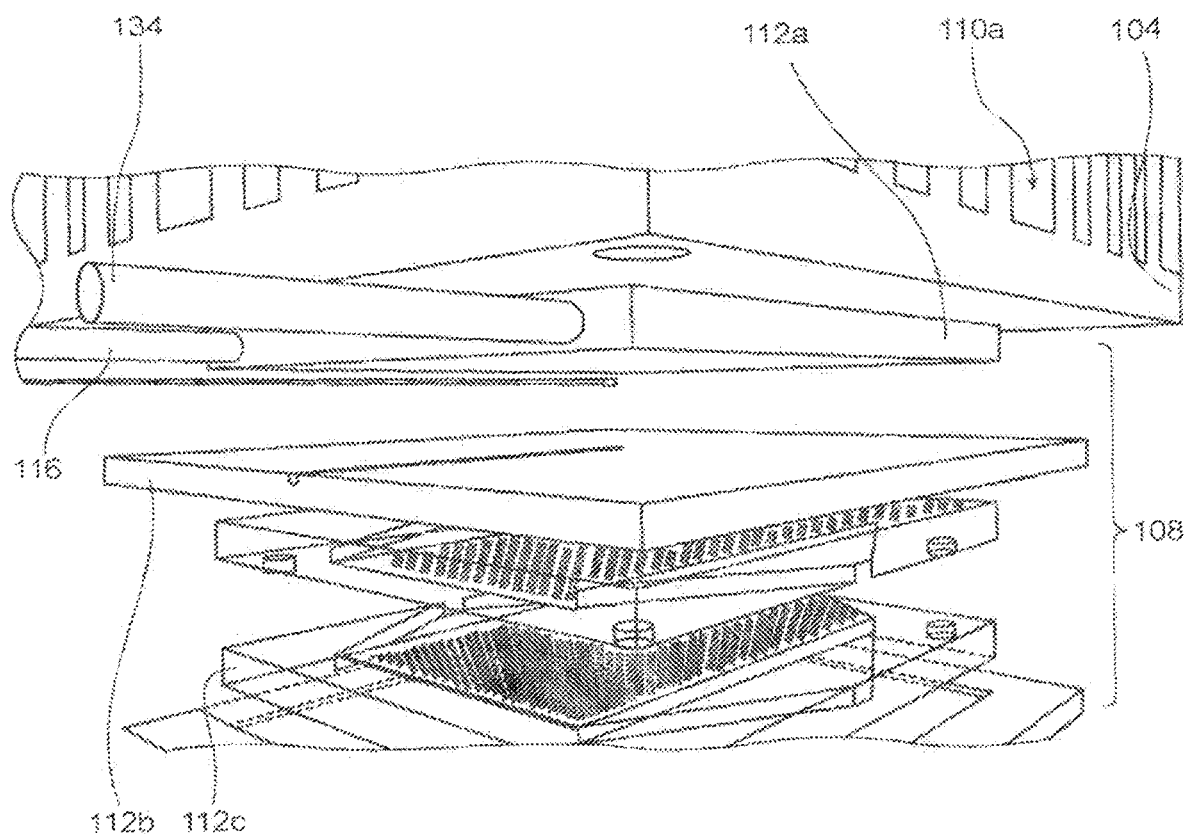
FIG. 3 illustrates a close up view of a modular microfluidic dialysis system, in an expanded position, in accordance with an embodiment of the present invention.

As referenced in FIGS. 1-3, the system 100 utilizes various micro-components that emulate the physiological parameters of the body 132 for enhancing the dialysis process. These micro-components provide numerous advantageous over traditional dialysis, such as hollow tube filtration and reverse osmosis. Through use of the microfluidic dialysis system 100, the more difficult to filter middle molecular weight uremic toxins and small solutes may be filtered out of the blood 134 more efficiently. Furthermore, the system 100 is modular, so as to enable scalability and conformance to different body types and dialysis requirements.

Figure 4A:
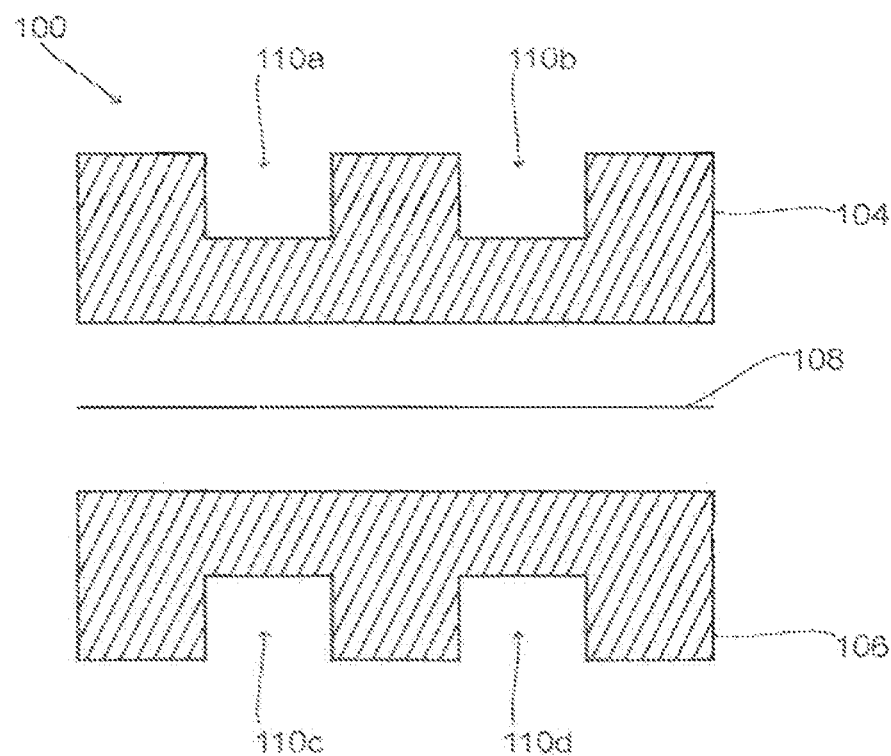
FIGS. 4A and 4B illustrate sectioned side views of an exemplary microfluidic unit, where
Figure 4B:
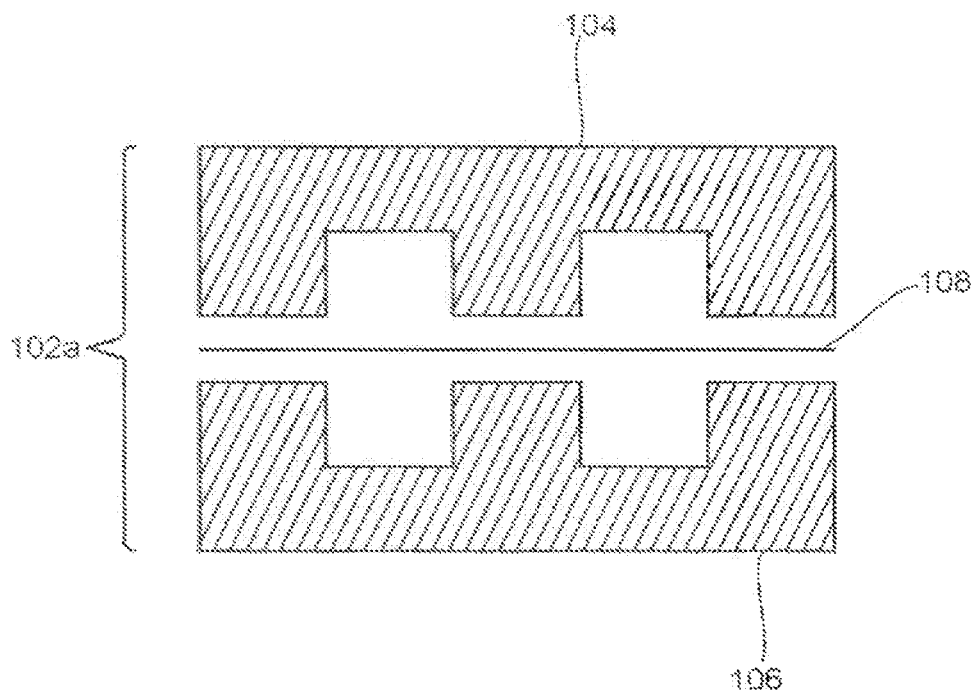

Looking now at FIGS. 4A and 4B, the device comprises a plurality of microfluidic units 102a-d that receive, filter, and return the blood 134 and dialysate 116 to the body 132. The microfluidic units 102a-d are chiefly configured to perform dialysis of blood 134 for removing middle molecular weight uremic toxins and protein-bound toxins, small solutes, hepatic toxins, water, and other impurities from the blood 134 through the use of microfluidic technology.

Figure 6:
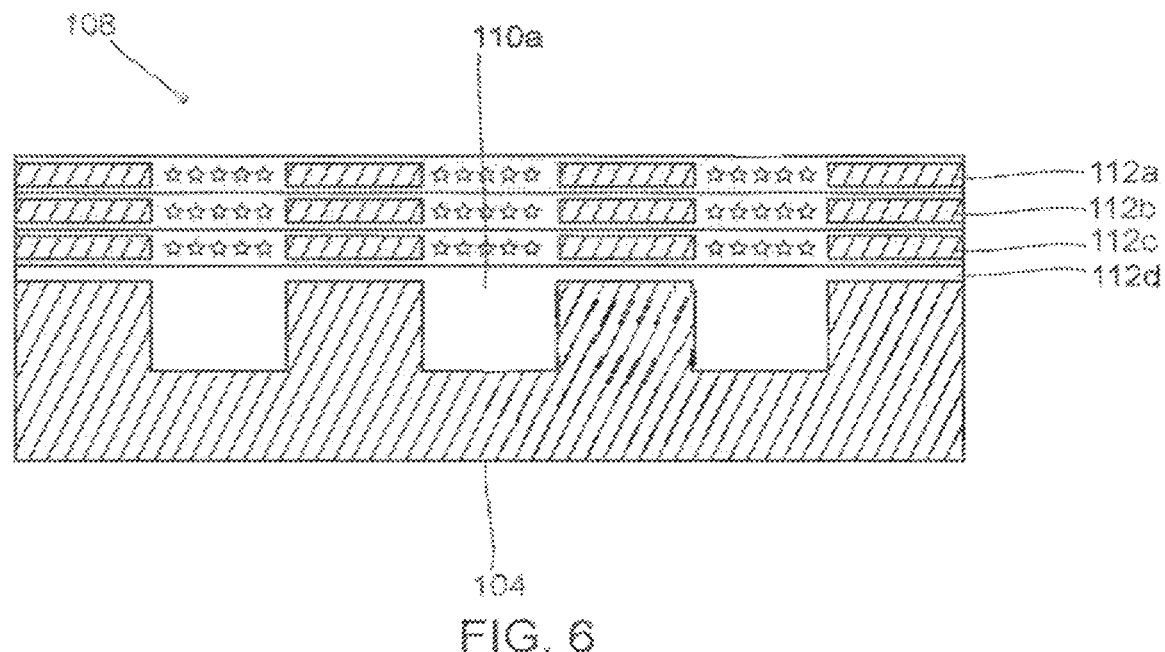
FIG. 6 illustrates a sectioned view of multiple layers of a semipermeable membrane positioned on a blood microfluidic chip, in accordance with an embodiment of the present invention.

In some embodiments, the microfluidic units/modules 102a-d are at least partially fabricated from a polymeric organosilicon compound. FIG. 6 illustrates the microfluidic units I 02a-d fabricated from any inert and biocompatible polymer used as microfluidic substrate like polymeric organosilicon compound, such as PDMS. The PDMs provides numerous advantageous, such as unique rheological properties that enhance flow of blood 134 and dialysate 116, transparency, capacity to stick to other micro-channels 110a-d, deformability, and nontoxicity. Though in other embodiments, various medical grade materials could also be used for fabrication of the microfluidic units/modules 102a-d.

Figure 7:
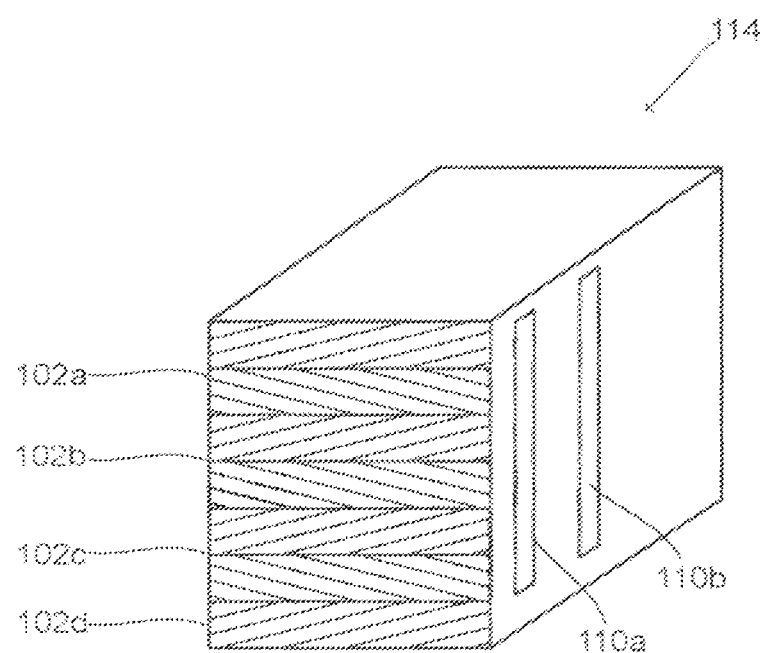
FIG. 7 illustrates a perspective view of multiple microfluidic units in a microfluidic housing, in accordance with an embodiment of the present invention.

As illustrated in FIG. 7, the plurality of microfluidic units 102a-d are arranged in modular configuration for enhanced scalability. In one embodiment, the microfluidic units 102a-d are combined into constructs and modules to operatively fit into a microfluidic housing 114. The number, size, and types of microfluidic units/modules 102a-d can be adapted for meeting various body types and dialysis requirements. This allows for more efficient dialysis of the blood 134.

In one example of the modular scalability of the system 100, about 20-40 microfluidic units 102a-d form a microfluidic construct. About 5 microfluidic constructs form a microfluidic module. The microfluidic module positions inside a microfluidic housing 114. In one embodiment, the microfluidic module must be aligned properly inside the microfluidic housing 114 before the micro-valves open. This helps minimize inefficient functioning of the system 100.

Looking back at FIG. 1, each the microfluidic unit comprises a blood microfluidic chip 104, a dialysate microfluidic chip 106, and a semipermeable membrane 108 disposed between the chips 104, 106. The blood microfluidic chip 104 is configured to carry blood 134, while the dialysate microfluidic chip 106 is configured to carry a dialysate 116. Both chips have substantially the same configuration, i.e., mirror images of each other. In one embodiment, different layers of the microfluidic chipset 104,106 are substantially flat substrates that form a width of about 100-1000 microns. This 100-1000 micron width may include the width of the semipermeable membrane 108. FIG. 2 shows the chips 104, 106 facing each other with the semipermeable membrane 108 sandwiched there between.

Figure 5A:
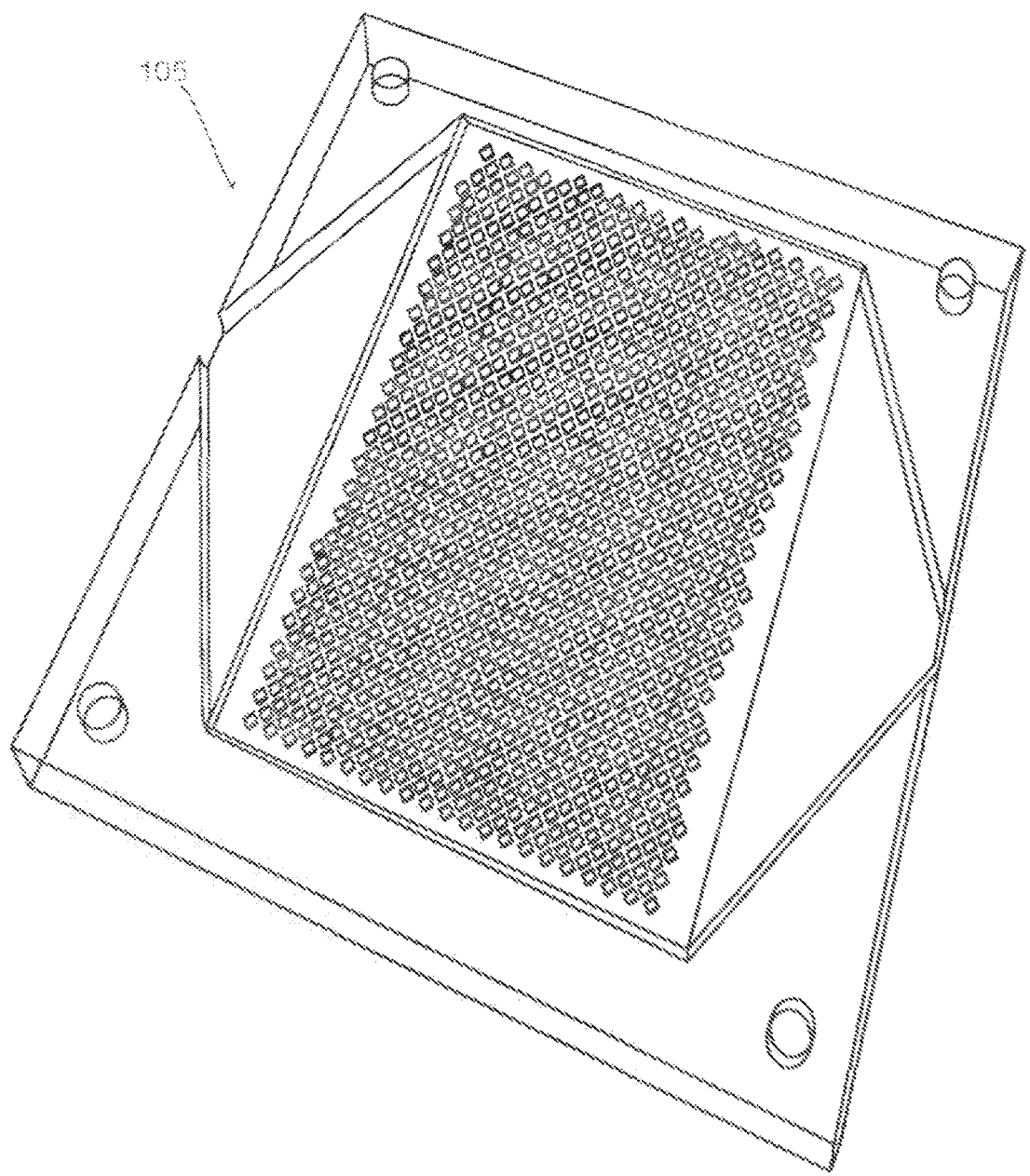
FIGS. 5A and 5B illustrate perspective views of an exemplary semipermeable membrane, in accordance with an embodiment of the present invention.
Figure 5B:
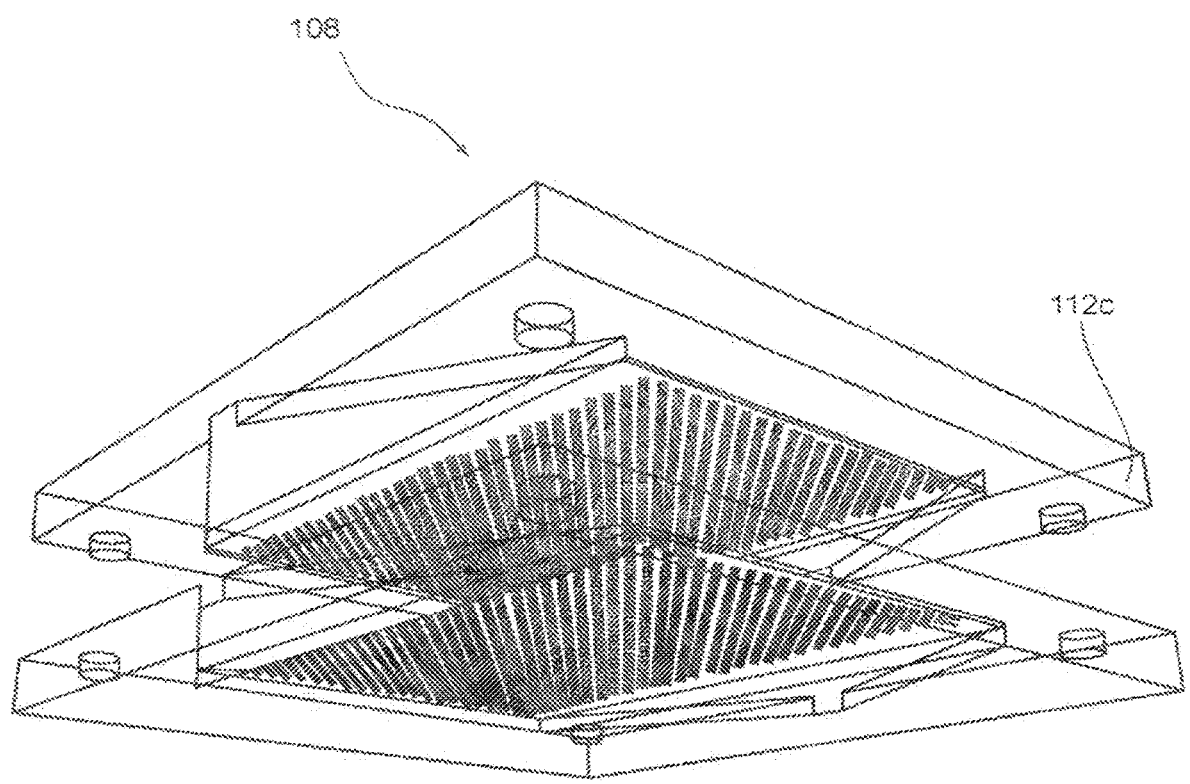

Looking back at FIGS. 5A and 5B, the blood microfluidic chip 104 and the dialysate microfluidic chip 106 are separated by a semipermeable membrane 108. The semipermeable membrane 108 provides the filtering capacity for the dialysis. As FIG. 2 illustrates, the semipermeable membrane 108 is configured to form a permeable barrier between the blood 134 and the dialysate 116. In this manner, the semipermeable membrane 108 enables passage of toxins, water, and small electrolytes from the blood 134 in the blood microfluidic chip 104 to the dialysate 116 in the dialysate microfluidic chip 106.

In one embodiment, the semipermeable membrane 108 allows only water and small electrolytes to pass. In another embodiment, the semipermeable membrane 108 is multilayered and comprises: a first layer 112a of activated charcoal; a second layer of resins 112b; a third layer 112c of specialized resin zirconium; and a fourth layer 112d of uremic. Though other filtering substrates and materials may also be used.

In one embodiment, the blood microfluidic chip 104 and a dialysate microfluidic chip 106 comprise integrated micro-pumps 130a-c for pumping blood 134 and dialysate 116 continuously. Though the micro-pumps 130a-c may also pump blood 134 or dialysate 116 intermittently, as needed. The micro-pumps 130a-b are configured to pump the blood 134 to and from the blood microfluidic chip 104. Similarly, the micro-pumps 130c are configured to pump the dialysate 116 to and from the dialysate microfluidic chip 106. The miniature size of the micro-pumps 130a-c minimizes the need for excessive quantities of dialysate 116 to be used for dialysis, which enhances portability and weight considerations for the system 100.

In one embodiment, the micro-pumps 130a-c may be specialized to pump specific fluids. For example, the micro-pumps 130a-c may include: two or more blood 134 micro-pumps 130a-c, one or more heparin micro-pump, one or more ultrafiltration micro-pump, and one or more dialysate and replacement fluid 116 micro-pump. In one embodiment, the plurality of micro-pumps 130a-c may include either electric micro-pumps 130a-c or pneumatic micro-pumps 130a-c.

The electric micro-pumps 130a-c are powered by the battery in the microfluidic unit The pneumatic pump may include a manual balloon hand micro-pump that can be used to generate and store a pressurized atmospheric air in a special reservoir for storage of compressed air in a Compressed Air Reservoir (CAR). This pressurized air operates the pneumatic micro-pumps 130a-c to lower use of battery power. In addition, the manual balloon hand micro-pump can be used manually to regenerate power.

Figure 15:
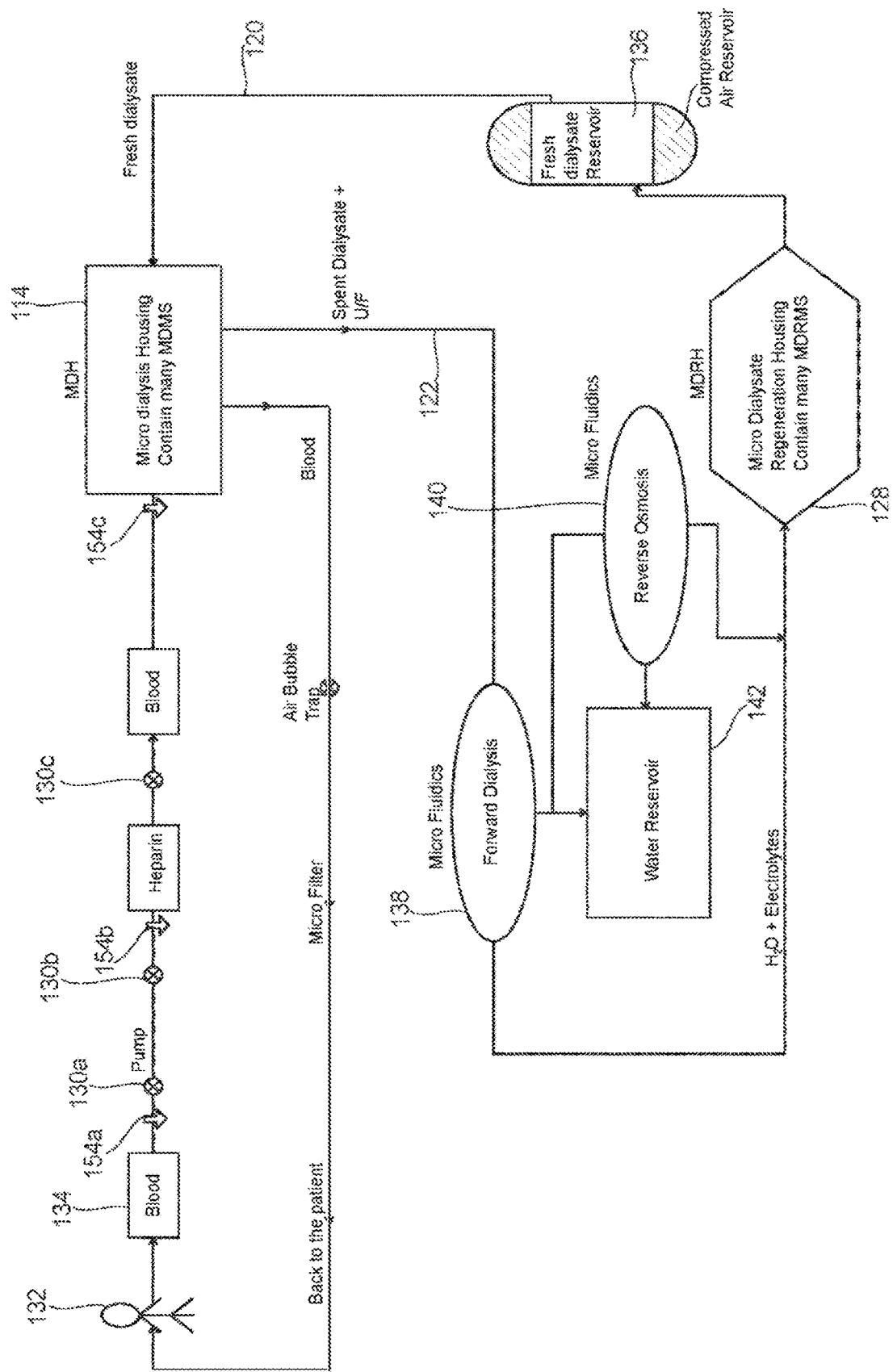
FIG. 15 illustrates a diagram of an exemplary microfluidic dialysis system, in accordance with an embodiment of the present invention.

In some embodiments, the chips further comprise micro-valves 154a-c for determining flow direction and mode of movement for the blood 134 and the dialysate 116 (FIG. 15).

The micro-valves 154a-c remain closed if the chips are not properly aligned. The micro-valves 154a-c may be controlled remotely or manually preset to a desired position. Factors such as pressure and the type of dialysate 116 also dictate the position of the micro-valves 1 54a-c. In one embodiment, an inflow and outflow tubing is attached to a manifold for dividing the blood 134 and dialysate 116 to each microfluidic chip 104, 106 and its associated microfluidic unit 102a-d.

Figure 11B:
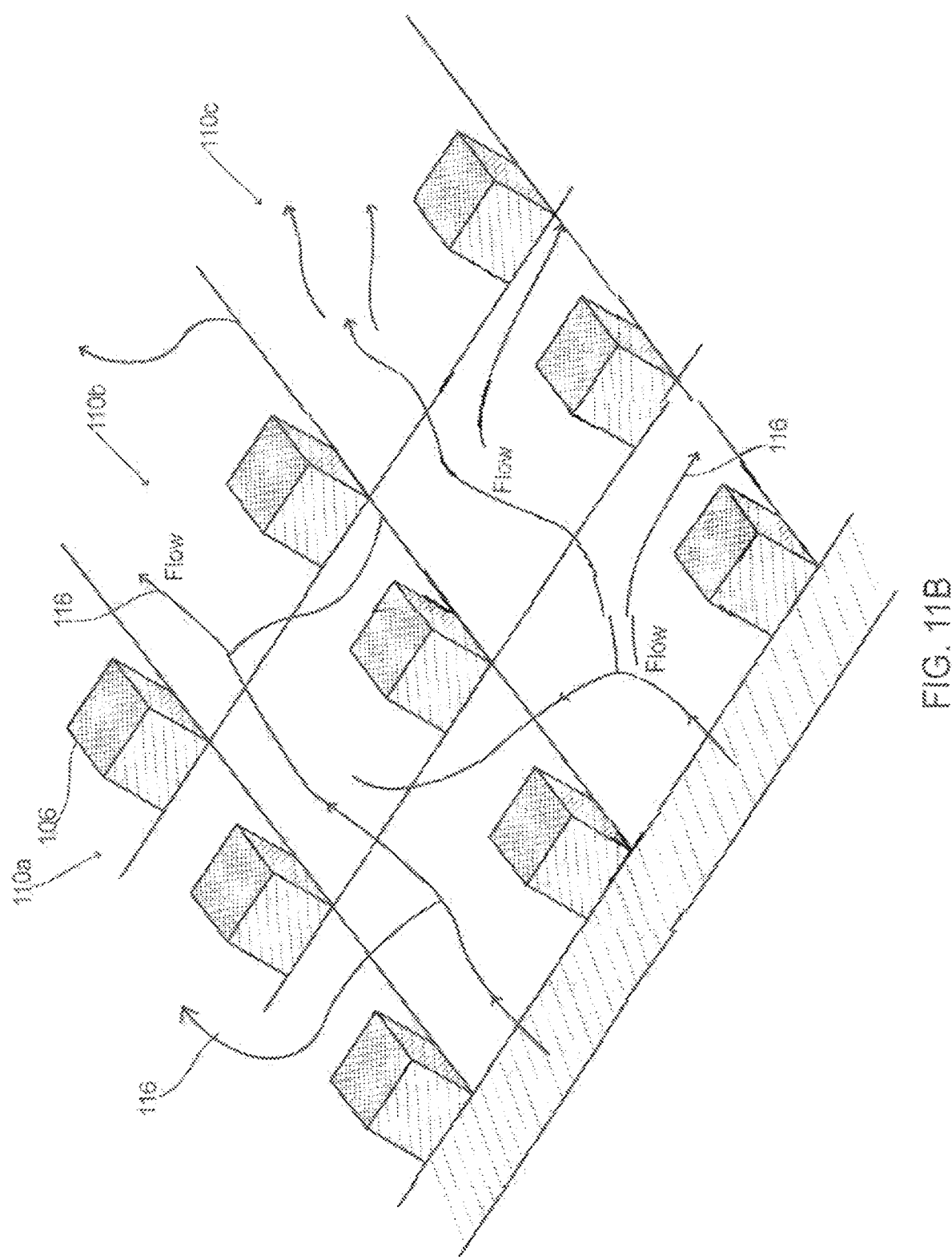
Figure 12A:
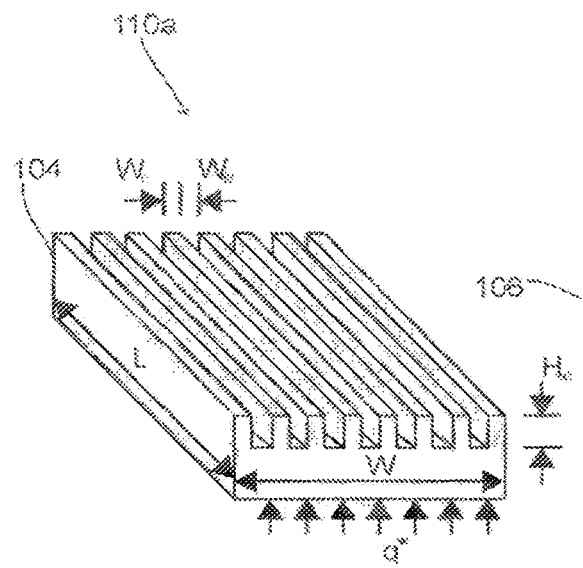
FIGS. 12A, 12B, and 12C illustrate top views of an micro-channels fabricated directly on a blood microfluidic chip, where
Figure 12B:
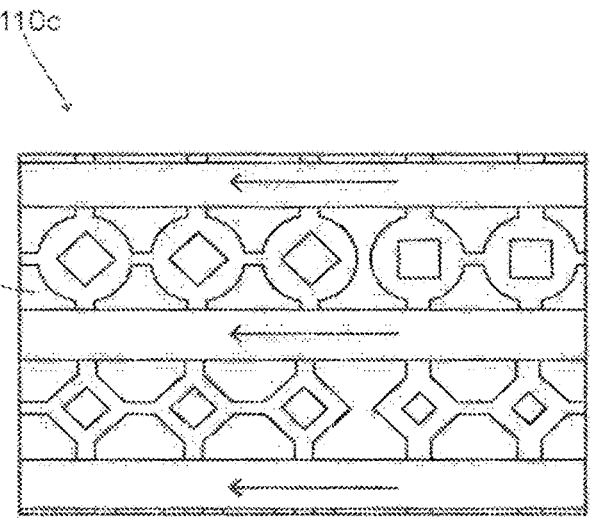
Figure 12C:
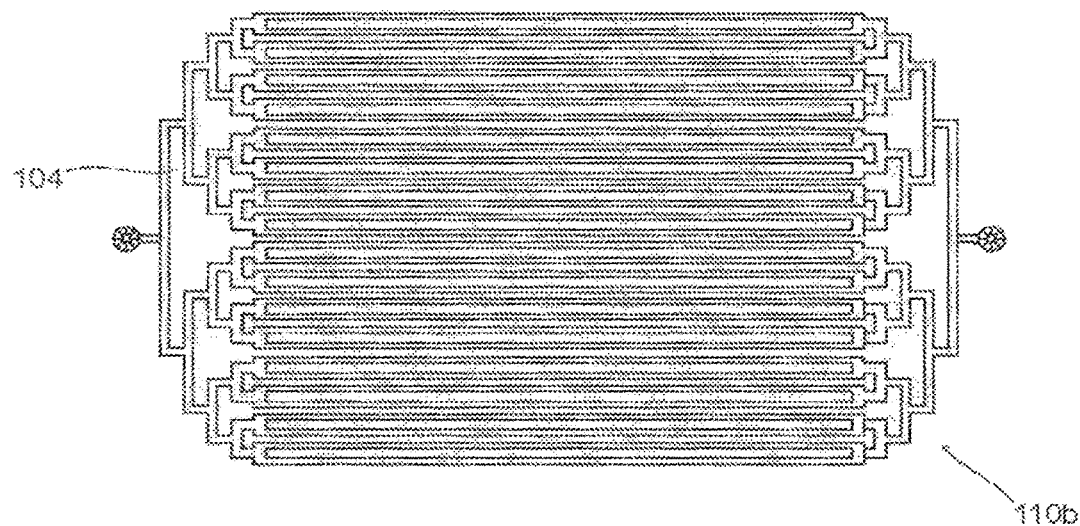

The chips 104, 106 further comprise a plurality of microchannels 110a-d for carrying the blood 134 and dialysate 116 to the appropriate chip 104, 106. As shown in FIG. 11A, the micro-channels 110a-b may be fabricated directly on the blood microfluidic chip 104 to carry the blood 134 to and from the blood microfluidic chip 104. In one example, FIGS. 12A, 12B, and 12C illustrate top views of micro-channels fabricated directly on a blood microfluidic chip, where FIG. 12A illustrates straight micro-channels, FIG. 12B illustrates parallel micro-channels about one hundred microns wide, and FIG. 12C illustrates branched micro-channels, as used in a bio-artificial liver.

As illustrated in FIGS. 1 IA and 1 IB, the microfluidic chips are designed with the following variables:
  Shape of the Channels: These microfluidic channels are designed in linear, parallel, crisscrossing, pillars and fractal or a combination of these shapes.
  Size of the Channels: These microfluidic channels have different dimension with different aspect ratios.
  Semipermeable Membrane types: These microfluidic channels are covered with different semipermeable membranes with different porosity (pore size), various Molecular Weight Cut Off (MWCO) values and different membrane characteristics to create specialized biomimetic vasculature—capillaries and lymphatic.
  Number of Layers: These chipsets can be double layer ton-layers as needed.
  Types of Resin or Polymer Used: inert, biocompatible polymers such as PDMS, Photo resin etc.
  The angled Countercurrent: The angle of the flow in the dialysate channels vs. the flow in other layers could range from 0 degrees (same direction/co-current flow) to 180 degrees (counter-current flow). This range of angled counter-current flow has advantages of providing a uniform gradient across the microfluidic chipset. Optimization for each Chipset can be done. In addition since the channels for the dialysate will be in the shape of "broken channels walls" or use of interrupted pillars, the flow of the dialysate has always three options: 0 degrees, 90 degrees and 180 degrees (see sketch)
  Use of Enhanced Dialysate: Standard dialysate will be used to make different concentrations of an activated mesoporous charcoal solution to increase the clearance while avoiding plugging of the channels.

Figure 8A:
FIGS. 8A and 8B illustrate schematics of exemplary micro-channels, where
Figure 8B:
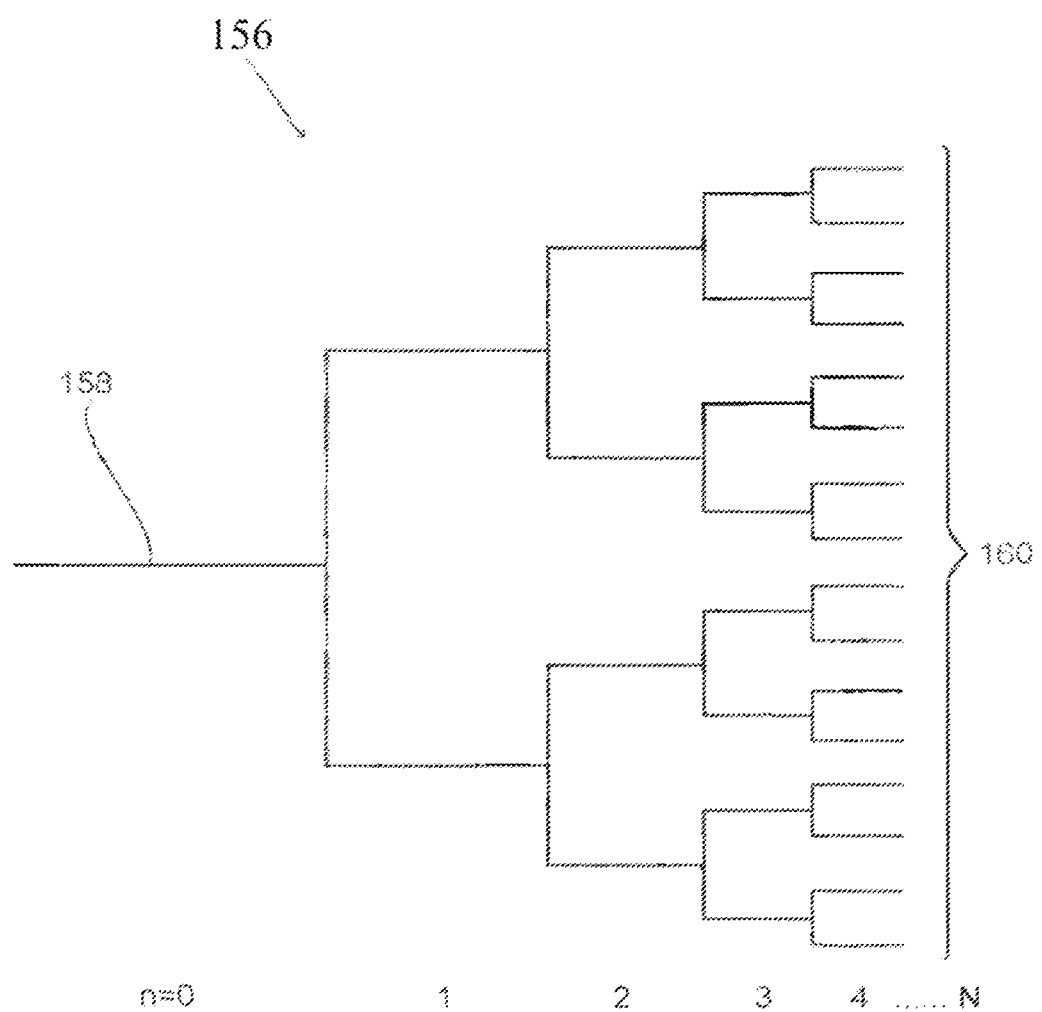

Thus, FIG. 8A illustrates one single micro-capillary unit made from two PDMS micro-channels 110a-d which sandwich a semipermeable dialysis membrane. This unit now emulates a capillary in the human body. By changing the characteristics and permeability of the membrane one can achieve different types of capillaries for engineered tissue and organ. The core technology described here is based on a combination of the microfluidic technology which can provide a very narrow conduit from 10 um to as large as 10000 microns width "conduit" or "channel" of different topology and shapes. This will allow emulating the micro-vasculature. However, this basically can act as a fluid transporter. However when this technology is combined in a particular manner, a non-biological representation of different capillaries and lymphatics is achieved. This core technology will be used to generate different tissues and/or organs to improve human health by either supporting or replacing the failing organs.

This innovative and proprietary MCAL Technology has the following benefits which sets it apart from other. These are the followings:

Emulating different vasculatures (capillaries, lymphatics)
Faster Diffusion & Convection
Higher Efficiency
Higher Surface Area (SA) to Volume (V) Ratio (SA/V)
Higher Clearances for Important Uremic Toxins
Scalable/From a Smaller Units/modules to a Larger Ones
Can be connected in Series or Parallel or in Combination
Multilayer with each layer acting either as a lymphatic or different type of capillary
Modular & Adjustable
Variable Angled cross flow/Countercurrent Flow
Variable aspect ratios ranging from 10 um to 2 mm
Can be used in many different applications Furthermore, microfluidics enables small dimensions of individual channels, which significantly decreases the lateral distance to diffuse through to the exchange membrane. As diffusion time scales with the square of the distance, shrinking the lateral dimension by 10× speeds up the diffusion by 100×. Faster diffusion means more efficient filtration and higher removal percentage even if all other parameters remain the same. This characteristic alone can improve the efficiency of dialysis 50-100 folds.

Furthermore, microfluidics uses photolithography to build very large and dense networks of channels with essentially the same ease as making a single channel The network combines the faster diffusion with a large increase of surface-to-volume ratio, since the microfluidic device has the same contact surface area as the traditional device, while having many times smaller volume.

The microfluidic system TOO allows for stacking many identical layers that are connected in parallel. Stacking preserves the superior surface-to-volume ratio while increasing the overall surface area of the exchange membrane as well as the volumetric throughput of the device, by a factor equal to the number of stacks. If the footprint of the device is allowed to increase as well, the parallel microfluidic connecting makes that factor scale like the cube of the linear dimension of the device! Hence, a I Ox increase in the linear dimension would result in a 1,000× increase in membrane surface area and in volumetric throughput. Thus, the proposed system would have significantly improved removal rate of toxins compared to traditional dialysis modalities.

By utilizing different specialized membranes such as Hemodiafiltration (HDF), HMWCO membranes the microfluidic device combines diffusive and convective transport to increase the clearance of middle-to-large molecules. Online hemodiafiltration (OL-HDF) has allowed the convective volume to be increased and has reduced the cost of the procedure. Studies have shown that OL-HDF reduces the incidence of amyloidosis and chronic inflammation, and decreases the mortality risk.

These microfluidic chipset modules can be stacked (i.e. Stacking 10, 20, etc. identical prototypes vertically and connecting them in parallel) toachieve scalability This special feature would allow gain of many folds in throughput. Thus, this device would have 4× the volumetric throughput, while offering higher efficiency of toxin removal by faster diffusion. The result would be significantly better therapy in a fraction of the traditional duration.

Figure 9A:
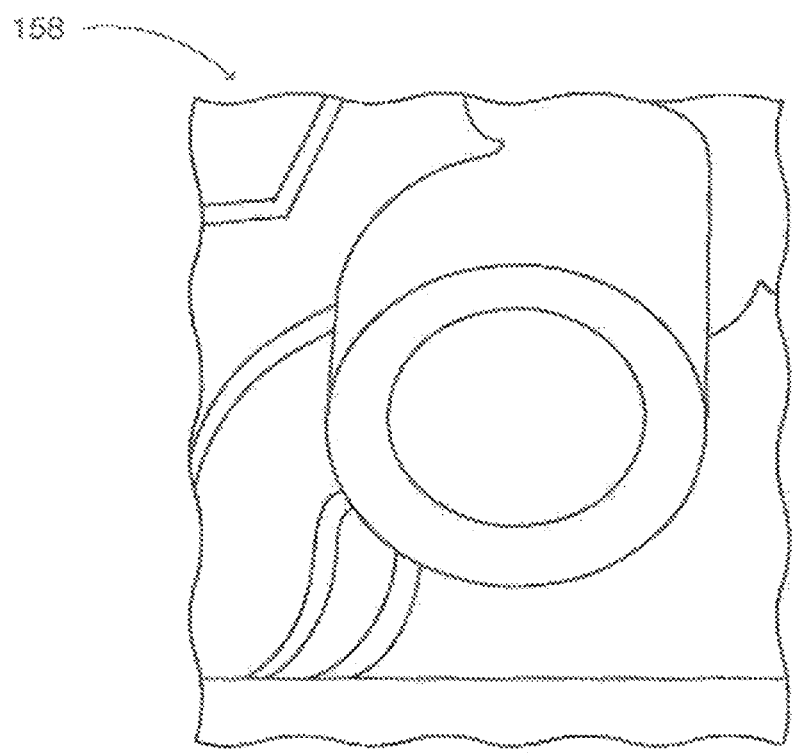
FIGS. 9A and 9B illustrate a comparison between an HFT dialyzer and an MFC Technology dialyzer, in accordance with an embodiment of the present invention.
Figure 9B:
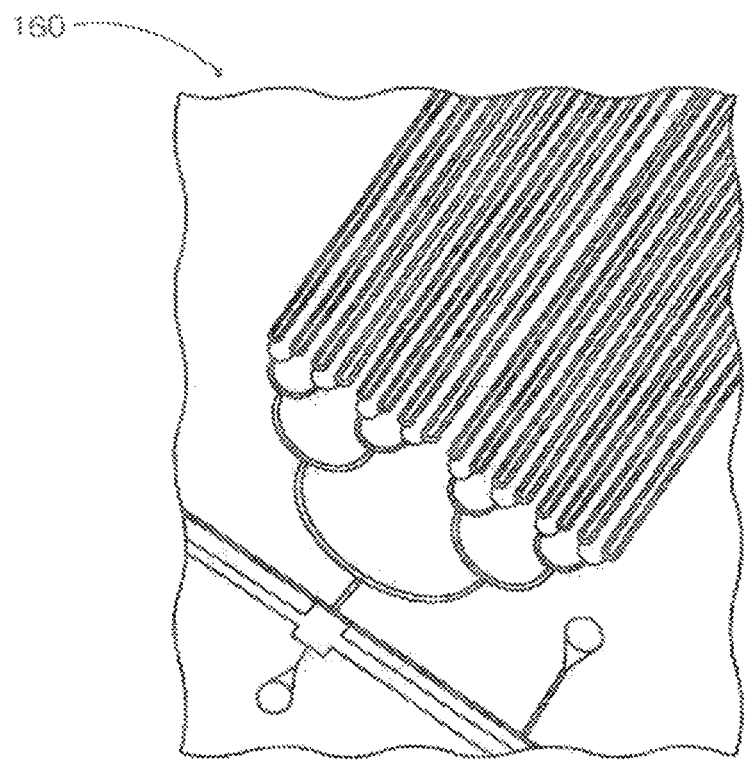

FIGS. 9A and 9B illustrate a comparison between an HFT dialyzer 158 and an MFC Technology dialyzer 160, while keeping the volume the same.

The micro-channels 110c-d follow a top down approach: The inflow into the chipset module is via a central inlet (or other approaches) which is divided in successive steps to provide a network of micro-channels 110a-d to distribute the oxygen, fluids and nutrients in a coordinated and uniform pattern. The inlet and outlet will have several design including a ledged design to control the distribution hydraulic resistance to be three orders of magnitude lower than the forward flow resistance in the permeation region. This means that there will be almost no non-uniformity in the pressure laterally across the permeation region.

In some embodiments, the microfluidic regenerating unit 118a-c may include at least one filtering/purifying member selected from the group consisting of: a sediment filter, a carbon filter, a zirconium carbonate filter, a deionizing resin, a micro-filter, an ultraviolet light, and a cold plasma regeneration apparatus. The microfluidic dialysis regenerating unit 118a-c negates the need for reverse osmosis filtering techniques. Though, as shown in FIG. 15, forward dialysis and reverse osmosis may still be used in the system 100.

Figure 13:
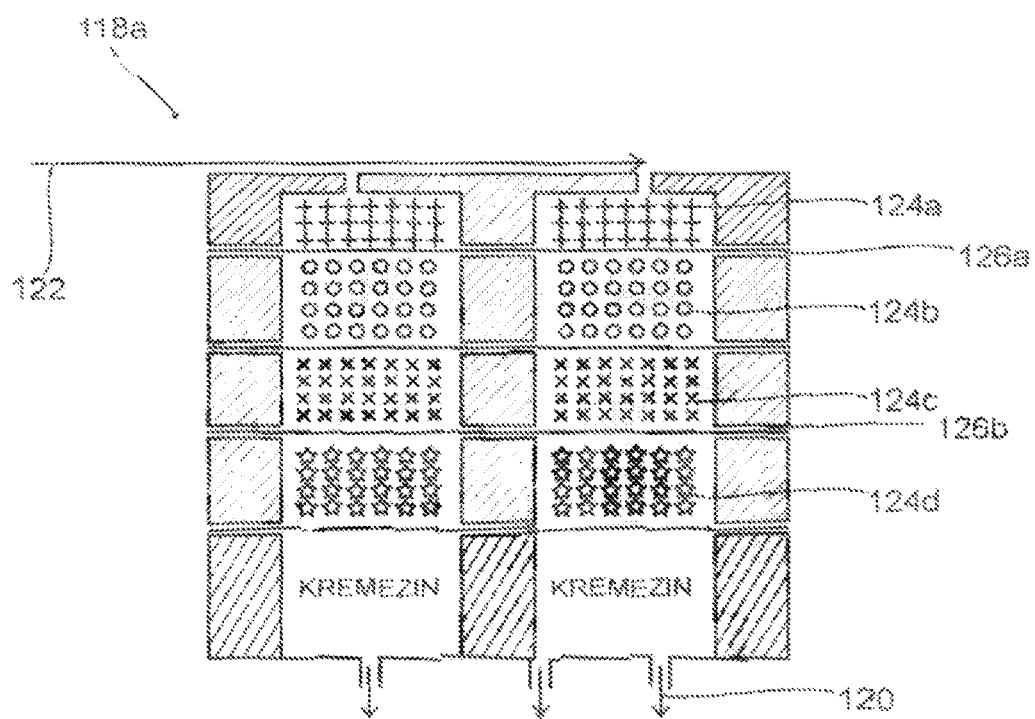
FIG. 13 illustrates a sectioned view of an exemplary microfluidic regenerating unit, in accordance with an embodiment of the present invention.

In yet another embodiment, the filtering components of the microfluidic regenerating unit 118a-c may include: a) Activated Charcoal (1 gram=500 $m^2$ surface area); b) Urease ($NH_2CO+H_2O \rightarrow CO_2+2$ $NH_3$; c) Zirconium Phosphate; d) Zirconium Oxide plus Zirconium carbonate; e) Composite Dry Chemical (to mix in with K, Mg, Ca); f) Granulated Carbonic Sorbent (deep pyrolysis of synthetic resin); In some embodiments, the microfluidic dialysis regenerating unit 118a-c may further comprise a slot for receiving a dialysate vial 136 containing fresh, unused dialysate. In one exemplary embodiment, the microfluidic regenerating unit 118a-c, as illustrated in FIG. 13, comprises multiple layers that are used to filter the contaminated dialysate 122. The layers are as follows: an activated charcoal substrate 124a, a low porosity membrane 126a, a urease substrate 124b, a zirconium phosphate substrate 124c, a high porosity membrane 126b, and a zirconium oxide substrate 124d.

Figure 14:
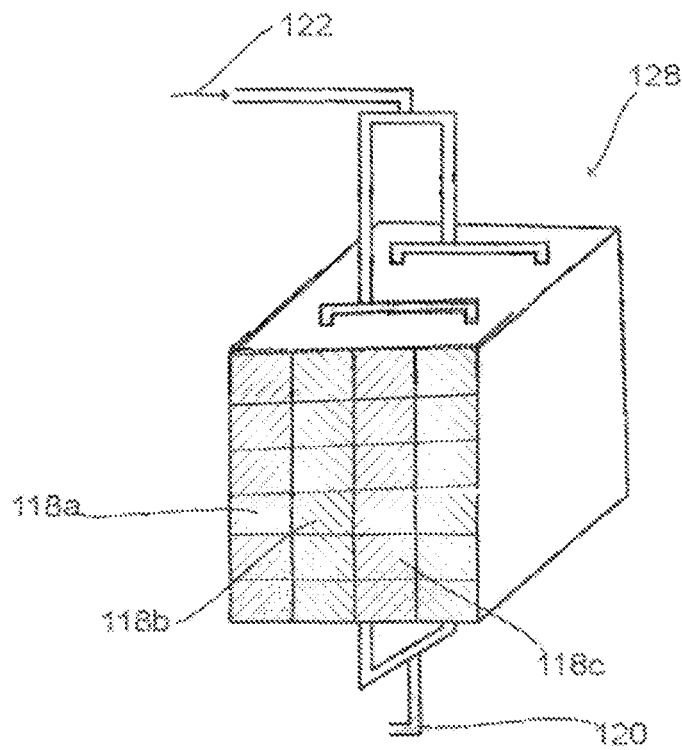
FIG. 14 illustrates a perspective view of a plurality of microfluidic regenerating units fitted inside a microfluidic regenerating housing, in accordance with an embodiment of the present invention.

In one embodiment, illustrated in FIG. 14, a plurality of microfluidic dialysis regenerating units 118a-c are configured to position inside a regenerating unit housing 128. Similar to the microfluidic units/modules 102a-d, the number and size of microfluidic dialysis regenerating modules/units 118a-c is adaptable to specific dialysis requirements. The modular configuration of the microfluidic unit 102a is also emulated, whereby five microfluidic dialysis regenerating units 118a-c may be used to make up one microfluidic dialysis regenerating construct; five microfluidic dialysis regenerating constructs may be used to make up one microfluidic dialysis regenerating module, and multiple microfluidic dialysis regenerating modules may be operatively fitted in the microfluidic regenerating housing 128.

Looking now at the block diagram of FIG. 15, the dialysis is initiated when blood 134 is pumped from the body 132 and circulated through the system 100 The micro-pumps 130a-c force the blood 134 from the body 132 to the microfluidic housing 114, which comprises a plurality of microfluidic modules/units 102a-d. The microfluidic units 102a-d operate as discussed above. The contaminated dialysate 122 from the dialysis process in the microfluidic housing 114 is then redirected to an external filtering process consisting of a forward dialysis 138, a reverse osmosis system 140, and a waste reservoir 142 for filtering out the water, toxins, and small electrolytes.

The reverse osmosis system 140 discussed for the external filtering process may utilize a reverse osmosis micro-pump to push water through a semipermeable membrane or filter which removes almost all of the contaminants in the contaminated dialysate 122, including bacteria and viruses. Other parts of the portable reverse osmosis system 140 may include a carbon filter which absorbs the chemicals added by the water department and a sediment filter which traps large pieces of debris. It is significant to note that if the water is very hard, a softener may also be installed which removes calcium and magnesium because these substances could damage the reverse osmosis system 140. In other embodiments, the reverse osmosis system 140 may produce two types of water: product water and reject water. The product water is the ultrapure water which enters the microfluidic housing 114 and is used to mix the dialysate for dialysis treatment. The reject water contains the bacteria that was cleaned out of the water and is sent to the water reservoir and down the drain for discarding.

From this external filtering process, the partially filtered dialysate flows to the microfluidic regenerating housing 128, which contains a plurality of microfluidic regenerating units/modules 118a-c for final filtering. A dialysate vial 136 may also be used to replenish the regenerated dialysate 120. The regenerated dialysate 120 then flows back to the microfluidic housing 114 for further dialysis processing.

In one optional embodiment, the system I 00 further comprises one or more warming devices (not shown) that are configured to activate charcoal and other components of the device as desired. One or more cooling devices (not shown) may also be used to cool the heated components and also to return the blood 134 to normal temperatures. For example, blood 134 may be warmed through the warming device and cooled through the cooling device, such that the dialysate 116 returns to the vile in the microfluidic dialysis regenerating unit 118a-c in a concentrated form. The warming device may be configured to warm the blood 134 to about 42° Celsius, after passing through the microfluidic unit. The cooling device may be configured to cool the plasma portion down to 35° Celsius, after passing through the microfluidic housing 128.

As discussed above, the system 100 is configured in a device. The device incorporates a machine that controls the therapy parameters and includes state of the art microfluidic-based dialyzer for performing the diffusive and convective dialysis as well as other filters/semipermeable membranes for the regeneration of the dialysate 116 thus enabling the system 100 to perform a complete dialysis treatment using small quantity of potable tap water. Parts of this device are a single-use disposable cassette. The electronic circuits in the device may include without limitation, a sensor control board, micro-pumps drivers, a main processor board, a type BF power supply, a power management circuit, a short term battery back-up, and a Wi-Fi dialysis filter component.

Further, the system 100 may include a user interface for monitoring I/O and net volume of blood 134 circulation. In additional embodiments, volume is monitored and adjusted, and a filter may be introduced for safety to trap any carbon/particulate matter and remove the carbon/particulate matter from the cellular portion before reentering the patient. The device may further include a bubble trap, a charcoal trap, and various filters for safely trapping any carbon/particulate matter and removing it from the cellular portion of the blood 134 before reentering the body 132 of the patient.

The Plasma Portion (P.P.-cell free portion) is directed to a chip module with a special design with a multilayer microfluidic chipset module comprising at least 5 layers. The middle layer is sandwiched between two mirror image layers. The P.P. is located in the central layer which is sandwiched between two identical layers containing dialysate+Albumin. These three layers are sandwiched between two identical layers containing dialysate+charcoal. The four membranes separating all five layers have characteristics of a High Molecular Weight Cut-Off (HMWCO) dialysis membrane in order to achieve albumin dialysis.

A multilayered microfluidic chipset unit/module for more efficient albumin dialysis. (The MCAL Technology microfluidic chipset AD unit/module).

A multilayered microfluidic chipset module-AD Module—is designed for performing much more efficient albumin dialysis and removal of the protein/albumin-bound toxins. This chipset design is unique since the albumin regeneration is built on the chip.

Please see FIG. 18, this is a 5-layered inert and biocompatible polymer used as microfluidic substrate such as PDMS based microfluidic chipset module. A single layer of microfluidic for blood compartment (blood layer) sandwiched between two two-layered charcoal and albumin dialysate layers placed in mirror image.

Between each of the following layers, the $1^{st}$ & $2^{nd}$, $2^{nd}$ & $3^{rd}$, $3^{rd}$ & $4^{th}$ and $4^{th}$ & $5^{th}$ layers, a high flux membrane (or other membranes) will be placed to separate each layer compartment and provide the needed membrane surface for dialysis to occur It is significant to note that all fluids flow in a countercurrent or angled countercurrent direction in respect to their adjacent layers.

Note: the flow of each layer will be manipulated and optimal direction of flow can be optimized and studied. The concurrent, countercurrent as well as tangential cross flows will be investigated, for best and optimal efficiency. The membranes used can vary but high flux or even membranes with higher MWCO characteristics may be utilized. In addition the rate of flow for each layer will be studied and optimized. The final chipset will have the ability to provide sampling and up to date monitoring of certain chemical and physiological values using biosensors embedded into the chip design.

Figure 16:
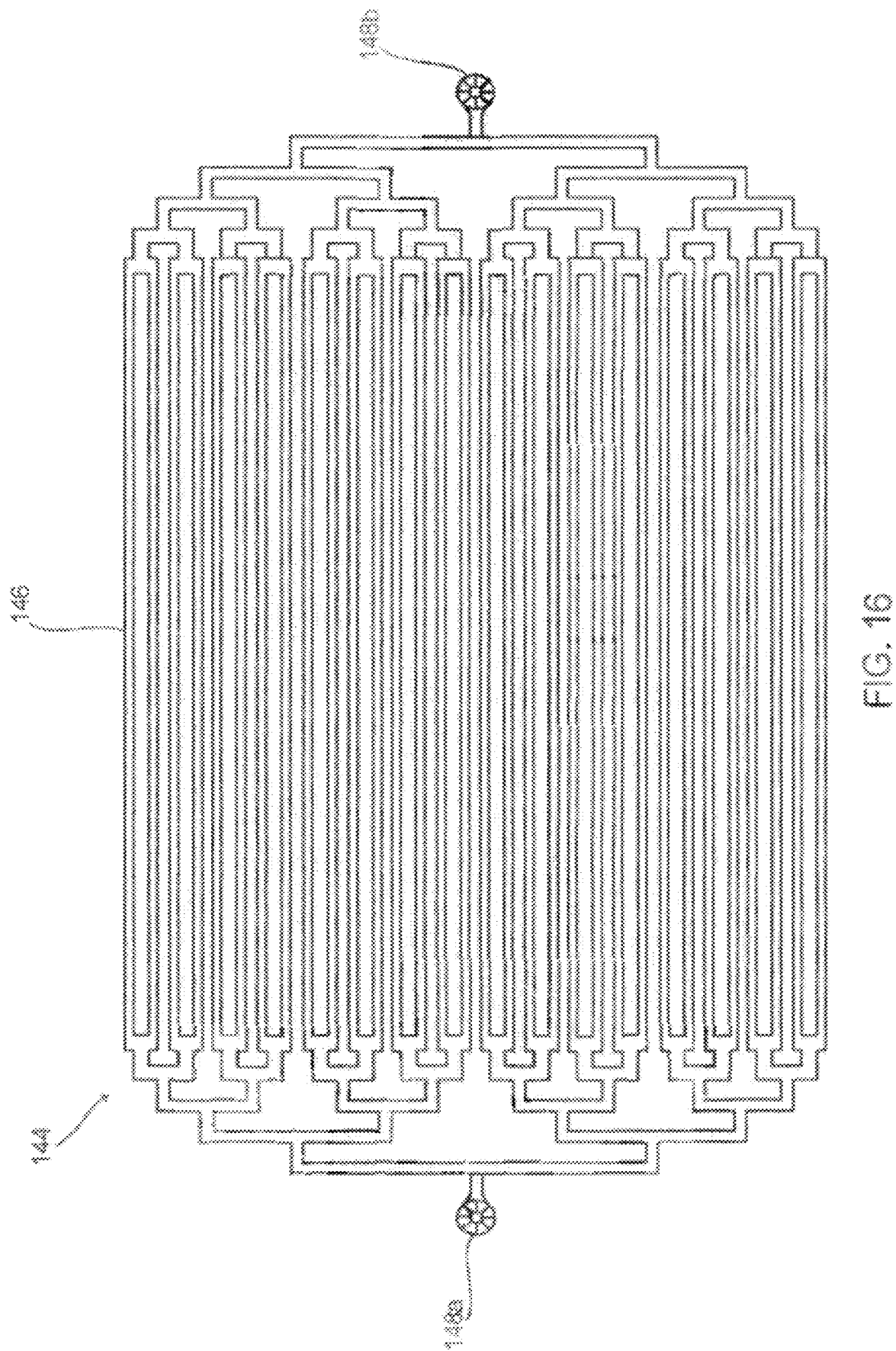
FIG. 16 illustrates a top view of an exemplary bio-artificial liver with branched micro-channels, in accordance with an embodiment of the present invention.

Turning now to FIG. 16, the system TOO may be effective for fabricating a bio-artificial liver 144 through substantially the same microfluidic principles discussed above. The bio-artificial liver 144 comprises substantially the same microfluidic units 102a-d, but in a more layered configuration that is consistent with the human organs.

In conclusion, the combined microfluidic based kidney and Liver dialysis device for MODS/sepsis system for removing middle molecular weight uremic toxins and small solutes, protein-bound uremic and hepatic toxins, and water from the blood through the use of microfluidic technology, and various embodiments thereof is provided.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

Combined Microfluidic Based Kidney and Liver Dialysis Device for MODS/Sepsis

The combined microfluidic-based Kidney and Liver Dialysis Device is composed of various biomimetically designed modular and microfluidic-based microfluidic chipset units based on The MCAL Technology. These combinations and permutations basic units that are assembled by connecting them in parallel or in series fashion. The final microfluidic device and its microfluidic chipset units may be placed in series on one larger single microfluidic chip. It should be noted that these microfluidic chipset units/modules/(The MCAL Technology basic units) may be assembled together in different permutation to allow unique development of other organ supports/replacement devices, bio-artificial organs support systems as well as portable dialysis devices.

The microfluidic Kidney/Liver Replacement dialysis device will have several permutations of 9 major modules/MCAL Technology microfluidic chipset units/modules depending on the final design of the project, each MCAL Technology module with a different and unique function. Each different unit/module is designed to emulate certain function of kidney and/or liver functions. Some of these MCAL Technology units/modules are optional.

It should be noted that all the dialysis devices, bioreactor organs, bio-artificial organ devices will include all the necessary and standard the micro-pumps, sensors, filters, and various alarms used in constructing these machines and also CRRT and HD/HP. These important components are not shown for the sake of simplicity.

These 9 microfluidic chipset units (modules) of the microfluidic Kidney/Liver Replacement Device are as follows:
1. PS module (Plasma Separation/Plasmapheresis)
2. HD module (Hemodialysis)
3. HP module (Hemoperfusion)
4. HDF and/or DF module (Hemodiafiltration) and/or Diafiltration)
5. AD module (Albumin Dialysis)
6. ADR module (Optional-Regeneration of Albumin Dialysate)
7. DR module (Optional—Dialysate Regeneration)
8. LD module (Optional-Lipid Dialysis)
9. BR Module (Optional—Bioreactor Organ)

The 9th MFC may be used to construct the Bio-Artificial by adding it in series to the microfluidic Kidney/Liver Replacement.

Please see FIG. 19, there are a few simple devices schematically presented to show development of three different yet similar Dialysis/support devices.

The first one is Microfluidic Kidney/Liver Replacement Device. All the simple devices in this portion have the option to be used with Lipid Dialysis by adding the LD microfluidic chipset unit of the MCAL Technology.

The second on is Bio-artificial Microfluidic Kidney/Liver Replacement Device. Any one of the simple devices in this microfluidic Kidney/Liver Replacement designs with addition of a Bio-Artificial bio-reactor. The BR module is added before the blood is returned to the patient (BTP), and all the simple devices in this portion have the option to be used with Lipid Dialysis by adding the LD MCAL Technology unit/module The third one is Portable microfluidic Kidney/Liver Replacement Device.

I. The MCAL Technology Microfluidic Chipset Unit/Module—the PS Module

This MCAL Technology microfluidic chipset (unit/module) which is plasmapheresis membrane that is sandwiched in between two inert and biocompatible polymers used as microfluidic substrate such PDMS (mirror image of each other) with specific aspect ratio to increase the diffusion.

The anticoagulated blood from patient is pumped, and then is anticoagulated (not performed here) before entering the first module of the device—the PS module. The PS module which emulates the function of a glomerulus in human nephron is where Plasmapheresis Membrane is utilized and will allow the plasma proteins to be filtered. Therefore, the PS module will filter all non-cellular components of the whole blood and generate two portions from the whole blood from patient entering it.

Cell portion is the portion containing mostly the cellular elements of the blood (WBC, RBC, Platelets) and some plasma. The composition of the plasma is not changed, only the plasma is separated from the whole blood. The hematocrit will be increased from 30-40% to about 50-70% coagulated. This portion is either returned to the patient or is delivered to a bioreactor if available). Meanwhile, the Plasma Portion is the portion containing non-cellular components of the whole blood (all proteins, electrolytes, and albumin). This is also anticoagulated will have hematocrit of 0% ready to be entered the next module. Before it goes to the next module it will be diluted I:I to 4:1 by adding 1-4 parts replacement fluid (various FR with different compositions such as normal saline or bicarbonate based fluid and etc.)

II the MCAL Technology Microfluidic Chipset Unit—the HD Module

This microfluidic chip at this module has a simple design of a hemodialysis membrane which is sandwiched in between two PDMS (mirror image of each other) with specific aspect ratio to increase the diffusion, convection via internal filtration.

The diluted PP portion enters the next module which is the HD module. In this module the PP will be dialyzed very well and composition of the plasma will change drastically. Since there is a diffusive and convective process involved, there is another input into the MFC—the dialysate.

The diluted and anticoagulated P.P. from previous module—PS module which has Hct of 0% will enter the MFC—the HD module which emulates the filtration function of the glomerulus in the human nephron. The PP will undergo an intensive diffusive dialysis against the fresh dialysate and also a convective dialysis via ultrafiltration. Of course a fresh dialysate is used during this process which will be regenerated through the R module if available or discarded.

The outflow of the HD module which is a well dialyzed and more concentrated PP is directed to the next module of the dialysis device.

III the MCAL Technology Microfluidic Chipset Unit—HP Module

This microfluidic chip at this module has a simple design of a specialized. PDMS micro-reservoirs where microfluidic channels lead into and out of, directing the flow of the PP over these reservoirs that contain a combination of resins and charcoal to perform the hemoperfusion more efficiently.

A well dialyzed and more concentrated PP is directed to this module—the HP module. The HP module emulates the function of the tubular portion of human nephron. The PP now enters the HP module where hemoperfusion is performed using charcoal and resin. The PP will be hemoperfused against the resin and charcoal to remove the tightly bound protein-bound toxins from the PP. The PP is further cleared from protein-bound toxins during this module. The PP then is directed to the next module—the albumin dialysis module-AD module. Note; the AD module may be replaced by ADR module which has the capability of regenerating the albumin for use by recirculation.

The MCAL Technology Microfluidic Chipset Unit/Module-HDF Module

This microfluidic chip at this module has a simple design of a hemodiafiltration membrane which is sandwiched in between two PDMS MFCs; —one PDMS with specialized cannels with specific aspect ratio to increase the diffusion, convection and the other PDMS with a special (see design of the MCAL Technology).

The HDF module of the MCAL Technology is used to regenerate the spent dialysate using a reservoir of charcoal and/or various resins and substances. The spent dialysate containing albumin (Dialysate+Albumin—Dial/Alb) enters the MCAL Technology-HDF against another input of the fresh dialysate containing charcoal and resin (Dial/Ch & R) solution from its reservoir separated by the hemodiafiltration membrane. The regenerated dialysate with albumin (Dial/Alb) is returned to MCAL Technology module A and the spent dialysate containing charcoal and resin (Dialysate+Charcoal+/−Resins-Dial/Ch & R) is returned to the reservoir containing the fresh Dial/Ch & R.

The MCAL Technology microfluidic Chipset unit/module—ADR (Albumin Dialysis Regeneration) module.

A multilayered PDMS based Microfluidic Chipset unit/module for more efficient albumin dialysis.

A multilayered PDMS microfluidic chipset is designed for performing much more efficient albumin dialysis and removal of the protein/albumin-bound toxins This chip design is unique since the albumin regeneration is built on the chip.

Please see FIG. 20, there is a 5-layered PDMS based microfluidic chipset. A single layer of PDMS for blood compartment (blood layer) sandwiched between two two-layered charcoal and albumin dialysate layers placed in mirror image.

Between each of the following layers, the $1^{st}$ & $2^{nd}$, $2^{nd}$ & $3^{rd}$, $3^{rd}$ & $4^{th}$ and $4^{th}$ & $5^{th}$ layers, a high flux membrane (or other semipermeable membranes) will be placed to separate each layer compartment and provide the surface for dialysis to occur. Note: All fluids flow in a countercurrent direction respect to their adjacent layers.

The concurrent, countercurrent as well as tangential cross flows may be used for best and optimal efficiency.

The membranes used can vary but high flux or even membranes with higher MWCO characteristics may be utilized. The diluted and well dialyzed PP enters this module—the AD module which emulates the function of the tubule portion of the human nephron. The diluted PP enters the AD module where albumin dialysis is performed using High-Molecular-Weight Cut-off (HMWCO) value membrane/High Performance Membrane which allows the PP to be dialyzed against albumin or a combination of albumin plus charcoal/resin. The first output of the MCAL Technology—the PP portion—will be directed back to the patient/subject while the second output of this module—the spent albumin dialysate—will be directed to the module D for regeneration.

The MCAL Technology Albumin Dialysis unit/module—The AD module.

Multilayered microfluidic-based (using inert and biocompatible polymers such as PDMS or other substrates) Microfluidic Chipset unit/module for albumin dialysis.

A multilayered microfluidic chipset is designed for performing much more efficient albumin dialysis and removal of the protein/albumin-bound toxins. Please see FIG. 21, this is a multilayered microfluidic chipset unit/module with a single layer of microfluidic micro-channels for blood/plasma compartment (blood layer) sandwiched between two albumin dialysate layers placed in mirror image.

The MCAL Technology Microfluidic Chipset Unit/Module—the DR Module (Optional) This microfluidic chip at this module has a simple design of a reverse osmosis membrane which is sandwiched in between two layers of microfluidic micro-channels microfluidic chips; the PDMS with specialized cannels with specific aspect ratio to increase the diffusion of pure water and the output is the concentrated dialysate with all the electrolytes and toxins The water that is passes to the other PDMS will be directed as pure water for dialysate regeneration as needed. The DR module (MCAL Technology-DR) is used to regenerate the spent dialysate. It has been designed to bypass the obstacles of an RO system. Its water purification system consists of the following parts:

a sediment filter which removes large particles from the water an ultraviolet light tray which kills bacteria and breaks down chemicals in the water (not required)

a carbon filter which adsorbs chemicals in the water a dual bed DI resin which removes dissolved electrolytes a mixed bed DI resin as a backup and safety net to the previous DI Resin an ultrafilter to remove bacteria (not required)

a 0.2 micron filter which removes any bacteria that may have been introduced into the system so it will not reach the patient Cold Plasma generation for sterilization (optional-use of either Direct or indirect cold plasma generation using air or $O_2$)

Components of the Dialysis Regenerating Unit
1. Activated Charcoal (1 gram=500 m2 surface area
2. Urease ($NH_2CO+H_2O \rightarrow CO_2+2NH_3$)
3. Zirconium Phosphate
4. Zirconium Oxide plus Zirconium carbonate
5. Composite Dry Chemical (to Mix in with K, Mg, Ca)

Kremezin Adsorbent to be Used Here Also

Granulated Carbonic Sorbent (Deep Pyrolysis of Synthetic Resin)

A reverse osmosis membrane and combination of Zirconium and activated charcoal. The spent dialysate containing all electrolytes and toxins enters the microfluidic chipset module-DR against the above components and the output can be used to generate fresh dialysate for the required modules. This DR module is mostly to be used in a portable version of the combined kidney and Liver Replacement device dialysis to reduce the amount of dialysate needed and thereby allowing portability and miniaturization of the dialysis device. (optional)

MCAL Technology module LD (Lipid Dialysis-Optional).

A multilayered inert and biocompatible polymer used as microfluidic substrate such PDMS based Microfluidic Chipset for albumin dialysis.

A multilayered inert and biocompatible polymer used as microfluidic substrate such PDMS microfluidic chipset is designed for performing much more efficient albumin dialysis and removal of the protein/albumin-bound toxins. Please see FIG. 22, this is a 3 (or multi)-layered inert and biocompatible polymer used as microfluidic substrate such PDMS based microfluidic chipset. A single layer of PDMS for blood compartment (blood layer) sandwiched between two albumin dialysate layers placed in mirror image.

Furthermore, the module in FIG. 22 is optional.

II. MCAL TECHNOLOGY Module BR (Bioreactor)

This microfluidic chip module has a complex design. The MCAL Technology bioreactor will be constructed using at least three (3) layers of inert and biocompatible polymer used as microfluidic substrate such as PDMS which are sandwiched and are separated by two membranes with high permeability to oxygen and nutrients (amino acids, glucose, and lipids etc.). The central layers (the cell chamber) have the largest dimension in order to hold a large number of desired viable cells. This chamber is filled with pre-specified numbers of encapsulated cells (kidney and/or liver cells in hydrogel) which are placed inside the cell chamber. The chamber is kept open by pillars that are placed strategically across the area to avoid collapsing of the two membranes one each side separating it from the other two layers. The other two PDMS layers that sandwich this cell chamber are wide enough for easy flow of the diluted C.P that is oxygenated! These two layers will provide the central chamber which contains the live cells, with their appropriate oxygen and nutrients, and removes the co2 generated Meanwhile the central layer is bathed by the P.P. after (maybe before) it has gone through intensive dialysis for removal of the toxins to avoid cell damage!

It should be noted that the central chamber can be filled with various tissues, cells, cell supporting elements, stem cells, encapsulated cells and/or combination of two or more of these tissue components. This microfluidic bioreactor organ unit will be placed in series with the artificial liver and/or artificial kidney) to form the Bio-Artificial-microfluidic based Kidney and Liver Replacement Device-a bioartificial organ unit.

By combining microfluidics and soft-lithographic molding of gels containing mammalian cells, a device for three-dimensional (3D) culture of mammalian cells in microchannels will be manufactured. Native components of the extracellular matrix, including collagen or Matrigel, make up the matrix of each molded piece (module) of cell-containing gel. Each module will have at least onedimension below –300 um; in modules of these sizes, the flux of oxygen, nutrients, and metabolic products into and out of the modules will be sufficient to allow cells in the modules to proliferate to densities comparable to those of native tissue (108-109 cells/cm3). These modules will be packed loosely into microfluidic channels and chambers yielding structures permeated with a network of pores through which cell culture medium could flow to feed the cells as well as encapsulated cells.

The two outer mirror image microfluidic layers that sandwich the central cell chamber (holding living cells) are wide enough for easy flow of the diluted cellular portion (C.P.) that is oxygenated! The design of the microchannels is to avoid clotting and cell damage to the cellular components of the blood such as RBCs, WBCs and platelets. These two layers will provide the central chamber which contains the live tissue cells and its components, with their appropriate oxygen and some nutrients, while removing the CO2 generated.

Meanwhile to keep the bioreactor cells healthy and functioning, the central layer containing the live cells will be bathed by the plasma portion (P.P.) which has plenty of macro- and micro-nutrient. Additionally, PP has many toxins that may be still present (protein-bound) as well as lacking proteins that are synthesized regularly by the organ (e.g. kidney, liver) hence providing the synthesis function of the organ that is missing. The PP portion may enter the MCAL Technology microfluidic chipset BR module—the bioreactor module/unit—after intensive dialysis for removal of the toxins to avoid cell damage or before it has gone through other modules. Then, these two outputs from the module BR are mixed and returned to the subject.

Mobile, modular and scalable microfluidic-based kidney and/or liver dialysis Device.

The present invention is a portable, compact, lightweight, self-contained hemodialysis machine for in-home or on the go hemodialysis device delivery machine, utilizing various biomimetically designed MCAL Technology microfluidic chipset units with ability for attaining higher diffusive and convective forces beyond the currently achievable uremic toxin clearances using the hollow fiber technology. FIG. 10 illustrates a comparison Table 162 that differentiates the Hollow Fiber Technology and MFC technology.

In addition, this microfluidic-based dialysis device requires lower blood volume and lower blood flow rates. Furthermore, the device is modular and scalable which can be adjusted to the patient's body surface area (BSA) & body weight as well to ensure individualization of therapy for all types of patients from pediatrics to adult which require different dialysis need. Being an adjustable dialysis unit, it is easy to achieve the targeted dialysis treatment. One size fits all will not be acceptable in hemodialysis any longer.

This portable and/or wearable hemodialysis device is based on the MCAL Technology. The device is a stand-alone hemodialysis device with unique design that replaces the currently available standard hollow fiber technology based dialysis which is very inefficient. The microfluidic-based dialyzers and filters will improve the efficiency of the dialysis several magnitudes. In addition, utilizing these biomimetically designed microfluidic-based chipset units will drastically increase middle molecular uremic toxins and protein-bound toxin removal via slow and highly efficient microfluidic-based dialyzer technology which ultimately will improve the morbidity and mortality of these patients and overall and also decrease healthcare cost and burden of ESRD treatment.

The device is a light-weight dialysis unit with miniaturized components which can run continuously or intermittently operating from 6-24/day seven days a week This allows gentle ultrafiltration to avoid severe post-dialysis fatigue and fluid shifts seen by regular HD. A computerized WIFI/remote feedback/interface/control of the device will allow minute to minute monitoring of important physiological as well as mechanical parameters.

Furthermore, this device will have the capacity regenerate dialysate fluid to minimize the amount of dialysate used daily to as little as –300 ml to 1500 ml/day Utilizing the microfluidic-based MCAL Technology units it can generate ultrapure dialysate which ultimately reduce inflammatory cytokines and ultimately mortality of patients.

Microfluidic Chipset Units:

Please see FIG. 23, this is a diagram showing how to utilize the various biomimetically designed microfluidic-based MCAL Technology microfluidic chipset units in the following ways.

MCAL Technology Based Microfluidic Chipset Unit Dialysate Regeneration Module

This PDMS microfluidic chip has Activated Charcoal/Polystyrene and other regenerating compounds placed in layers separated with semipermeable membrane with pores only allowing water and small electrolyte passage. Therefore the spent dialysate will pass through all the layers of the MCAL technology based microfluidic chipset Dialysate Regenerating Unit/module.

Design and Components of Dialysate Regeneration Module

This component is designed to refresh and regenerate the spent dialysate, by removing the toxins as well as correcting the electrolyte and its PH. In order to achieve portability, reduction in size the dialysate fluid has to be much smaller than the amount used in regular standard hemodialysis A regular cube vs. cylinder filled with the appropriate sorbents and charcoals There are Two Designs for this Component:
1. Regular Dialysate Regeneration Unit (rDRU)
2. Microfluidic Dialysate Regeneration Unit (mDRU)
  Regular Dialysate Regeneration Unit DRU (rDRU)

A container (various shapes including cube, cylinder etc.) packed with sorbet material with a special connection for attachment of new dialysate ampoule to the mobile, modular and scalable microfluidic-based kidney and/or liver dialysis Device via the DRU The regular (non-microfluidic) DR module—is a rectangular cube with dimensions equaling 300-1000 ml (300-1000 cm3) [i.e. 10 cm×10 cm×7 cm which is packed with 3-4 layers of carbon fibers, zirconium carbonate, Zirconium phosphate, urease, etc.

The DRU has a special slot for inserting a vial of fresh Dialysate. This Dialysate vial can be changed as needed.

MCAL Technology Based Microfluidic Dialysis Regenerating Module

The microfluidic chipset DR module has a Dialysate Regenerating Unit which has been designed to bypass the obstacles of an RO system. Its water purification system, consists of the following parts
- a sediment filter which removes large particles from the water
- an ultraviolet light tray which kills bacteria and breaks down chemicals in the water (not required)
- a carbon filter which adsorbs chemicals in the water
- a dual bed DI resin which removes dissolved electrolytes
- a mixed bed DI resin as a backup and safety net to the previous DI Resin
- an ultrafilter to remove bacteria (not required)
- a 0.2 micron filter which removes any bacteria that may have been introduced into the system so it will not reach the patient
- Cold Plasma generation for sterilization (optional)

The microfluidic chipset DR module has the advantage of using less water than an RO, only about 300-1500 cc/per treatment Components of the Dialysis Regenerating Unit
1. Activated Charcoal (1 gram=500 m2 surface area
2. Urease ($NH_2CO+H_2O \rightarrow CO_2+2NH_3$
3. Zirconium Phosphate
4. Zirconium Oxide plus Zirconium carbonate
5. Composite Dry Chemical (to Mix in with K, Mg, Ca)

Granulated Carbonic Sorbent (Deep Pyrolysis of Synthetic Resin)

The Reverse Osmosis (RO) System

The reverse osmosis (RO) system uses a micro-pump to push water through a semipermeable membrane or filter which removes almost all of the contaminants including bacteria and viruses. Other parts of a portable RO machine include a carbon filter which absorbs the chemicals added by the water department and a sediment filter which traps large pieces of debris. If the water is very hard, a softener may also be installed which removes calcium and magnesium because these substances could damage the RO system.

The RO machine produces two types of water: product water and reject water. The product water is the ultrapure water which enters the hemodialysis machine and is used to mix the dialysate for your dialysis treatment. The reject water contains the bacteria that was cleaned out of the water and is sent down the drain and discarded.

Therefore, the mobile, modular and scalable microfluidic-based kidney and/or liver dialysis device can accommodate to different catabolic needs in addition to patients weight and surface area for optimal dialysis.

Micro-Pumps

At least 7 micro-pumps are needed for the mobile, modular and scalable microfluidic-based kidney and/or liver dialysis Device.

1. Blood pump (2)
2. Heparin pump (1)
3. U/F pump (1)
4. Dialysate pump (2)

May use two different micro-pumps I) Pneumatic and 2) Electric

1. Pneumatic Micro-Pump (Balloon Hand/Palm Pump)—OPTIONAL

The pneumatic pump is a manual balloon hand pump that can be used to generate and store a pressurized atmospheric air in a special reservoir for storage of compressed air called CAR (CAR-Compressed Air Reservoir). This pressurized air will be used to run the pneumatic pumps to lower use of battery power. In addition, these can be used manually to regenerate power.

The CAR unit has a balloon hand pump which can be used to manually fill the Compressed Air Reservoir as needed. The CAR unit will dispense a specified amount of air to run the pneumatic pumps at a certain rate. These pneumatic micro-pumps also have back-up battery powered electrical micro-pump.

2. Electric Micro-Pump

These micro-pumps run on the rechargeable battery of the unit.

Cooling and Heating of the Dialysate

Use of these two modalities (cooling and heating) is to increase the Activated Charcoal absorption and desorption. This may add to the weight of the unit Patient's body temperature may be used.

Ultrapure Dialysate

Ultrapure fluid has been associated with better health outcomes as well as less inflammation. Definition of Ultrapure Dialysate: Bacteria <0.1 CFU/ml; Endotoxins <0.03 IU/ml Need smaller amount for the MKD Use the Diasafe membrane by Fresenius to generate an ultrapure dialysate when constructing the chipset Backfiltration and back diffusion are extremely important clinically especially for sicker patients.

Major disadvantages of high flux dialyzer membranes are the Backfiltration of Endotoxin fragments and other inflammatory provoking substances.

Forward Osmosis for Dialysate Regeneration (Optional)

Water is drawn across a semipermeable but solute impermeable—from the feed solution (Spent Dialysate) to Draw solution (high concentration of Na plus bicarbonate in this case).

The spent dialysate (after several runs) will be added to a bicarbonate container separated from the spent dialysate by a Cellulose Acetate membrane to achieve a Forward Osmosis.

1. The Feed fluid=Spent Dialysate
2. The Draw fluid=High concentration of Bicarbonate Sodium
3. The membrane=Cellulose Acetate
4. Input from the output of the Dialysate Microfluidic Chipset
5. Output to the dialysate regeneration unit The Organ Support and Replacement Use of the MCAL Technology in Designing Bioreactor for Different Types of Artificial Organ Modules The Bioreactor Design and Function—The microfluidic platform will be fabricated from inert and biocompatible substrates used in manufacturing microfluidics For example, PDMS and the chitosan fibers wound on a frame will be embedded in a PDMS platform, and HepG2 cells will be seeded and cultured forming clusters around the microfibers.

By combining microfluidics and soft-lithographic molding of gels containing mammalian cells, a device for three-dimensional (3D) culture of mammalian cells in microchannels is developed. Native components of the extracellular matrix, including collagen or Matrigel, make up the matrix of each molded piece (module) of cell-containing gel. Each module had at least one dimension below ~300 µm; in modules of these sizes, the flux of oxygen, nutrients, and metabolic products into and out of the modules was sufficient to allow cells in the modules to proliferate to densities comparable to those of native tissue ($10^8$-$10^9$ cells/cm$^3$). Packing modules loosely into microfluidic channels and chambers yielded structures permeated with a network of pores through which cell culture medium could flow to feed the encapsulated cells. The order in the packed assemblies increased as the width of the microchannels approached the width of the modules. Multiple cell types could be spatially organized in the small microfluidic channels. For many types of cells, behavior in two-dimensional (2D) culture differs from that in three-dimensional (3D) culture. Among biologists, 2D culture on treated plastic surfaces is currently the most popular method for cell culture. In 3D, no analogous standard method—one that is similarly convenient, flexible, and reproducible—exists.

Single Organ Unit of Liver, Kidney, Pancreas and Etc. The lobule/or organ unit will be constructed as follows:

Three or more layers of the microfluidic microchannels are separated by two or more semipermeable membranes with good permeability to oxygen and nutrients (amino acids, glucose, and lipids etc.). The central layers (the cell chamber) have the largest dimension in order to hold a large number of desired viable cells. This chamber is filled with pre-specified numbers of encapsulated cells (kidney or liver cells in hydrogel) which are placed inside the cell chamber. The chamber is kept open by pillars that are placed strategically across the area to avoid collapsing of the two membranes one each side separating it from the other two layers. The other two PDMS layers that sandwich this cell chamber is wide enough for easy flow of the diluted C.P. that is oxygenated These two layers will provide the central chamber which contains the live cells, with their appropriate oxygen and nutrients, and removes the co2 generated. Meanwhile the central layer is bathed by the P.P. after (maybe before) it has gone through intensive dialysis for removal of the toxins to avoid cell damage.

It should be noted that the central chamber can be filled with many different tissues, cells stem cells and other components as well as liver cells, kidney cells, combination of the two in mixture or alternating a specified volume of each encapsulated cells desired-liver and kidney. This organ unit will be placed in series with the combined microfluidic-based kidney and Liver dialysis device for MODS (artificial liver) or Mobile, and modular microfluidic dialysis device delivery (artificial kidney) to form the biomimetically designed microfluidic-based Bio-artificial kidney or Liver dialysis device for MODS.

Biomimetically Designed MCAL Technology Based Microfluidic Chipset Bioreactor Unit Module/(Liver Tissue/Cells are Used as an Example Here)

The Bioreactor organ (here Liver is used as an example) is a biomimetically designed microfluidic-based bioartificial liver replacement for an In Vivo and/or Ex Vivo use.

These uniquely designed microfluidic-based bioreactors are based on the MCAL Technology which are intended to be
 a. Modular
 b. Scalable
 c. Immunoisolated (no need for immunosuppression)
 d. Well-oxygenated
 e. Well-nourished For Ex Vivo model it would have several additional unique characteristics such as
 a. Adjustable
 b. Nanosensors for continuous monitoring
 c. Replenishable The microchannels and the microreservoirs having micron size dimension ranging from I 0-2000 micron and different heights to maximize diffusion and convection of the desirable substances such as blood, blood components, plasma, plasma components, dialysate, fluids with different properties and contents, oxygen and other gases, micro- and macro-nutrients, hormones, growth factor, etc. Additionally the surface of these chambers/reservoirs/channels will be modified and covered with appropriate and necessary ECM/Collagen material or other tissue components to make the desired tissue/organ/cell/MSCs/Stem cells grow and stay viable.

The microfluidic bioreactor organ is a macro-chamber that is rectangular shaped, consisting of several major components that are integrated. It consists of two modules:
 1. Plasma Separator
 2. The Bioreactor This device has a special design with at least two main permutations. This permutation is based on the simple option of where to direct the plasma portion (P.P.) output from the MCAL Technology based plasma separator module-PS chipset unit/module/module. There are basically two main designs:
 1. Indirect Exposure of the Cells with Plasma Portion (P.P.)
 2. Direct Exposure of the Cells with Plasma Portion (P.P.)
Note: there could be other permutation of these two designs using microfluidic chips Overview of the Scheme of the Biomimetically Designed Bioreactor Organ:

The artificial bioreactor organ (here liver is used as an example) consisting of several modules which are placed serially either continuously on the same chipset module, or disjointed on different chipsets that are connected serially to emulate a human organ/tissue such as liver lobule. A large collection of these "artificial organ units/modules make up an artificial bioreactor organ. Due to the fact these modules are simple basic units and can be added, remover, or replaced the ultimate design would have the capability of replacing any one of these chips modules if they fail to work properly, without disrupting the function of the other organ units!

The modules are as follows:

MCAL Technology Based PS Module (Plasma Separation Chipset Module)

This microfluidic module will use a plasmapheresis membrane over a microfluidic channels to perform a plasmapheresis or cytapheresis. Thereby, the input of the whole blood through this module will have two outputs 1) the cell portion (C.P.), which mainly contains the cellular components of the whole blood in small amount of plasma 2) the plasma portion (P.P.), which is devoid of any cellular elements. The C.P. output is then immediately directed to the bioreactor construct is a separate line, while the P.P. is directed to the bioreactor after going through the module 2.

MCAL Technology Based BR Module (Bioreactor Chipset Module)

This microfluidic Bioreactor will use a multilayer inert and biocompatible polymers for microfluidic substrate such as PDMS construct to achieve:

1. Oxygenate and provide nutrients as well as removal of the $CO_2$ using the C.P. which has a high hematocrit. The C.P. is directed to the outer two layers of the bioreactor (see bioreactor function and design). The nutrient and the oxygen are delivered via two permeable membrane.
2. To bathe the hepatocytes in the hydrogel with the "dialyzed" P.P. from module #1 this will enter the central layer of the bioreactor. Hence the toxins removed by the bioreactor.

The Description of the Bioreactor Organ for In Vivo Use and its Components

First Design

The Microfluidic Bioreactor is a macro-chamber that may have various shapes such as circular, rectangular or other shapes, consisting of several major components that are integrated.

MCAL Technology Based Chipset PS Module 1: The Plasma Separator Module

1. Whole blood enters the Bio-Artificial Liver Device.
2. The first module of this device is where plasma portion (P.P) as well as cellular portion (C.P) components of the whole blood is separated.
3. This is accomplished using a plasmapheresis membrane.
4. The P portion is further separated into a Rich Plasma Portion (RPP) and Serum Portion (SP) without the plasma proteins.
5. The RPP will be returned to the patient.
6. The S portion which contains the micro and macro nutrients are diverted to the next module.
7. The C portion is further separated into RBC portion and the WBC/Platelets portion.
8. The WBC portion is returned to the patient.
9. The RBC+Platelets portion is directed to the next module.
10. The next module is a microfluidic multilayer PDMS construct that has multiple copies of a two layered microfluidic channels that are alternating while being separated by ECMO membranes.

MCAL Technology Based Chipset BR Module 2: The Bioreactor Module

There is no Direct Flow of the plasma portion over the cells/tissue/stem cells and other cellular components+ECM This module is a repetition of an organ unit that is composed of three or more layers of microfluidic channels/reservoirs and different types of semipermeable membranes that are constructed as follow:

I. Layer Ax:
Microfluidic channels for the passage of RBC portion in parallel to the hepatocytes This layer as well as other similarly designed layers (Ax1, Ax2, Ax3, etc.) will receive the RBC rich portion from the previous module. This fluid will support the vital oxygen needed for the proper functioning of the tissue, cells, and stem cells. The oxygen will flow through the ECMO membrane (Layer Me-ECMO membrane).

II. Layer Me:
The Membrane Oxygenator that is a typical Extra Corporeal Membrane Oxygenator
This layer is a membrane that separates the two microfluidic layers and allows the RBC portion in the Layer B to provide oxygen for the in the Layer A without direct intact with them.

III. Layer Bx:
These Microfluidic channels holds tissue, cells, stem cells hepatocytes or other needed tissue components (stem cells as well as ECM) in Microreservoirs. This layer as well as other similarly designed layers (Bx1, Bx2, Bx3, etc.) will receive not come in contact with the Plasma Portion from previous module. This fluid will diffuse through a membrane (layer Mh-HMWCO membrane) to provide the tissue, cells, stem cells, MSC with macro and micronutrients requirements as well as the glucose IV. Layer Mh:
The high molecular weight cut-off membrane (HMWCO) separates the two microfluidic layers and provides the microencapsulated MSC/Hepatocytes with macro and micronutrients requirements as well as the glucose. This membrane allows the hepatocytes in the Layer Bx without coming in direct contact with them.

V. Layer Cx:
These microfluidic channels is used to flow the Plasma Portion from the module I to provide the tissue, cells, stem cells and other needed tissue components (stem cells as well as ECM) in Micro-reservoirs macro and micronutrients requirements as well as the glucose through a membrane (layer Mh-HMWCO membrane).

VI. Layer Mh:
The high molecular weight cut-off membrane (HMWCO) separates the two microfluidic layers and provides the MSC, tissue, cells, stem cells with macro and micronutrients requirements as well as the glucose. This membrane allows the tissue, cells, and stem cells in the Layer Bx without coming in direct contact with the immune components of the plasma or blood.

VII. Layer Bx:
These Microfluidic channels holds hepatocytes and other needed tissue components (stem cells as well as ECM) in Micro-reservoirs. This layer as well as other similarly designed layers (Bx1, Bx2, Bx3, etc.) will receive not come in contact with the Serum Portion from previous module This fluid will diffuse through a membrane (layer Mh-HMWCO membrane) to provide the microencapsulated MSC/Hepatocytes with macro and micronutrients requirements as well as the glucose.

VIII. Layer Me:
The Membrane Oxygenator that is a typical Extra Corporeal Membrane Oxygenator This layer is a membrane that separates the two microfluidic layers and allows the RBC portion in the Layer B to provide oxygen for the microencapsulated hepatocytes in the Layer A without direct intact with them.

IX. Layer Ax:
Microfluidic channels for the passage of RBC portion in parallel to the hepatocytes This layer as well as other similarly designed layers (Ax1, Ax2, Ax3, etc.) will receive the RBC rich portion from the previous module. This fluid will support the vital oxygen needed for the proper functioning of the microencapsulated hepatocytes. The oxygen will flow through the ECMO membrane (Layer Me-ECMO membrane).

Many repeats all these eight layers of the PDMS chips and membranes that make up a hepatic unit will make up the Bio-artificial liver of different sizes for different body sizes.

Each Construct=1 Bioreactor Organ (Hepatic) Unit/Module

First Design Module: (the cellular portion and plasma portion from the PS module are directed to this BR module microfluidic channels 1$^{st}$ Layer: microfluidic channels Ax Layer/Red Cell Portion $2^{nd}$ Layer Mxe Layer/ECMO Membrane
$3^{rd}$ Layer: microfluidic channels Bx Layer/Hepatocyte Complex
$4^{th}$ Layer Mxh Layer/HMWCO Membrane
$5^{th}$ Layer: microfluidic channels Cxl Layer/Plasma Portion
$6^{th}$ Layer Mxh Layer/HMWCO Membrane
$7^{th}$ Layer: microfluidic channels Bx Layer/Hepatocyte Complex
$8^{th}$ Layer Mxe Layer/ECMO Membrane
$9^{th}$ Layer: microfluidic channels Ax Layer/Red Cell Portion
  Each Construct=1 Bioreactor Organ (Hepatic) Unit/Module
  First Design Module: (the cellular portion is returned to the patient and plasma portion from the PS module is only directed to this BR module
  $1^{st}$ Layer: microfluidic channels; Media/Plasma Compartment
  $1^{st}$ Membrane HMWCO Membrane >500 KDa
  $2^{nd}$ Layer: microfluidic channels; Live Hepatocyte Compartment
  $2^{nd}$ Membrane HMWCO Membrane >500 KDa
  $3^{rd}$ Layer: microfluidic channels; Media/Plasma Compartment
Second Design
MCAL Technology Based Chipset Bioreactor (BR) Module Use of whole blood; No direct flow of plasma over the tissue/cells/stem cells/MSC/etc. (here hepatocytes as example)
This module is a repetition of four layers of microfluidic microchannel chip and semipermeable membranes that make up the hepatic unit which are constructed as follow:
  I. Layer A:
Microfluidic channels that pass through hepatocytes in Micro-reservoirs.
[This layer as well as other similarly designed layers (A1, A2, A3, etc.) will receive the Serum Portion from previous module. This fluid will bathe and provide the microencapsulated MSC/Hepatocytes with macro and micronutrients requirements as well as the glucose.]
  II. Layer Me:
The Membrane Oxygenator that is a typical Extra Corporeal Membrane Oxygenator.
[This layer is a membrane that separates the two microfluidic layers and allows the RBC portion in the Layer B to provide oxygen for the microencapsulated hepatocytes in the Layer A without direct intact with them.]
  III. Layer B:
Microfluidic channels for the passage of RBC portion in parallel to the hepatocytes
[This layer as well as other similarly designed layers (B1, B2, B3, etc.) will receive the RBC rich portion from the previous module. This fluid will support the vital oxygen needed for the proper functioning of the microencapsulated hepatocytes.]
  IV. Layer Me:
The Membrane Oxygenator that is a typical Extra Corporeal Membrane Oxygenator
[This layer is a membrane that separates the two microfluidic layers and allows the RBC portion in the Layer B to provide oxygen for the microencapsulated hepatocytes in the Layer A without direct intact with them.]
Repeat all four layers that form a unit generate different sizes of bioartificial liver Hence the multilayer microfluidic module is schematically presented as follows:
  Each Construct=1 Bioreactor Organ (Hepatic) Unit/Module Third Design Module:
  $1^{st}$ Layer: microfluidic channels A Layer/Hepatocyte Complex
  $2^{nd}$ Layer Me Layer/ECMO Membrane
  $3^{rd}$ Layer: microfluidic channels $B_1$ Layer/RBC Cell Portion
  $4^{th}$ Layer Me Layer/ECMO Membrane
  $5^{th}$ Layer: microfluidic channels A Layer/Hepatocyte Complex These above schematics are some simple designs for the microfluidic channels/chambers. These channels and microreservoirs can be designed in many exotic shapes, sizes and depths to improve the biomimetic component of these two bioreactor modules (MCAL Technology based microlfidic chipset bioreactor organ unit/module.

In one embodiment, the bio-artificial organ/tissue such as liver, kidney, pancreas and etc. (Liver is used as example here) 144 may include several modules disposed either serially or continuously on the same blood or dialysate microfluidic chip Though in other embodiments, the bio-artificial organ 144 may be disjointed on different chipsets that are connected serially to emulate any human organ such as human liver lobules. Those skilled in the art will recognize that large collection of artificial organ units such as liver lobules make up an artificial organ most specifically in this example the liver. Due to the fact these organ modules/units (i.e. liver lobules here for liver) can be constructed on different microfluidic chips, the ultimate design would have the capability of replacing any one of these chips 104, 106 if they fail to work properly, without disrupting the function of the other liver units.

In one possible embodiment, the bio-artificial organ-(here for example liver-144 comprises a microfluidic bioreactor having a macro-chamber that—may have various shapes and forms including a rectangular shaped chamber, consisting of several major microfluidic components integrated therein. The microfluidic bioreactor includes two modules: a plasma separator module and a bioreactor module. Various exotic designs may be possible for the artificial liver (or other artificial organs) microfluidic channels 146. The bio-artificial organ-liver-144 may include a microfluidic and biomimetic designed bio-artificial kidney or liver replacement for an In Vivo and/or Ex Vivo use Further advantageous of the microfluidic bio-artificial organ (liver) 144 are that it is designed to be: modular, scalable, Immunoisolated (no need for immunosuppression), well-oxygenated, and well-nourished. It should be noted that this scheme and arrangement maybe used to develop various numbers of bioartificial bioreactors emulating various organs such as kidney, pancreas, bone marrow, etc.

The bio-artificial bioreactor organ (any organ however, here for example liver tissue is used)-liver-144 may include a plurality of bio-artificial micro-channels 146 and a plurality of bio-artificial microreservoirs 148a, 148b for carrying and storing tissue, tissue components, cells, stem cells, structural components of tissue and support, whole blood and/or its components, plasma and its components 134 and any liquids such as dialysate, modified dialysate containing charcoal and/or resin, nutritional supports liquids containing macro- and/or micro-nutrients, oxygen, growth factors, hormones and etc. 116. The bio-artificial micro-channels 146 and a plurality of bio-artificial microreservoirs 148a, 148b are configured into myriad exotic shapes, sizes and depths to improve the biomimetic component of a bio-artificial-any tissue/organ-such as liver 144. In some embodiments, the micro-channels 146 and the micro-reservoirs 148a, 148b comprise a micron size dimension ranging from 10-1000 micron and different heights to maximize diffusion and convection of the desirable substances from oxygen to micro- and macro-nutrients to and from the tissue components and cells (live cells/tissues) in the micro-reservoir. Additionally the surface of these chambers/reservoirs/channels will be modified if necessary and covered with appropriate and necessary supporting material such as ECM/Collagen material and etc. to make the tissue/cells such liver such as hepatocyte/MSCs/Stem cells grow and stay viable.

The bio-artificial bioreactor organ-liver-144 has a special design with at least two main permutations. (Note; this bioreactor can be used for constructing any bio-artificial bioreactor organs such as pancreas, kidney, liver and etc. however, for example liver cells/hepatocytes are used here). This permutation is based on the simple option of where to direct the serum portion output from the plasma separator module. There are basically two main designs: an indirect exposure of the cells with serum portion. A direct exposure of the cells with serum portion. Though in some embodiments, there could be other permutation of these two designs using microfluidic chipset modules.

The bio-artificial bioreactor organ/tissue (for example liver) 144 may include several modules disposed either serially or continuously on the same blood/tissue or fluid/gas/dialysate microfluidic chip. This microfluidic module utilizes a plasmapheresis membrane over an inert and biocompatible polymer used in microfluidic manufacturing such as PDMS based channels to perform a plasmapheresis and plasma separation. Thereby, the input of the whole blood through this module will have two outputs 1) the cell portion (C.P.), which mainly contains the cellular components of the whole blood in small amount of plasma 2) the plasma portion (P.P.), which is devoid of any cellular elements. The C.P. output is then immediately directed to the bioreactor construct is a separate line, while the P.P. is directed to the bioreactor after going through the module 2.

In the microfluidic module embodiment, whole blood enters the bio-artificial bioreactor organ/tissue- (here shown for liver) 144. The first module of this device is where plasma portion (P.P) as well as cellular portion (C.P) components of the whole blood is separated. This is accomplished using a plasmapheresis membrane which has high molecular weight cut off membrane characteristics. The P portion is further separated into a Rich Plasma Portion (RPP) and Serum Portion (SP) without the plasma proteins. The RPP will be returned to the patient. The S portion which contains the micro- and macro-nutrients which are diverted to the next module. The C.P portion is further separated into RBC portion and the WBC/Platelets portion. The WBC+Platelets portion is returned to the patient. The RBC portion is directed to the next module. The next module is an inert and biocompatible polymer used in microfluidic manufacturing such as multilayer PDMS construct that has multiple copies of a two layered microfluidic channels that are alternating while being separated by Extracorporeal Membrane Oxygenation (ECMO) membranes used here for oxygenation.

Though in other embodiments, the bio-artificial bioreactor organ/tissue—here used liver as an example 144 may be disjointed on different chips that are connected serially to emulate human liver lobules. This microfluidic Bioreactor utilizes an inert and biocompatible polymer used in microfluidic manufacturing such as multilayer PDMS construct to achieve: a) Oxygenate and provide nutrients as well as removal of the CO2 using the C.P. which has a high hematocrit. The C.P. is directed to the outer two layers of the bioreactor (see bioreactor function and design). The nutrient and the oxygen is delivered via two permeable membrane; and b) To bathe the live cells/tissues such as hepatocytes in the hydrogel with the "dialyzed" P.P. from module I this will enter the central layer of the bioreactor. Hence the toxins removed by the bioreactor.

Those skilled in the art will recognize that large collection of artificial organ/tissue modules such as liver modules (lobules) make up an artificial organ such as liver. This holds true regarding other organs such as kidney, pancreas. Due to the fact these cells/tissues (here liver lobules) can be constructed on different microfluidic chips, the ultimate design would have the capability of replacing any one of these chips if they fail to work properly, without disrupting the function of the other tissue/organ units/modules—here liver units.

The bio-artificial liver 144 has a second design. The second design also has a plasma separator and a Bioreactor. However the layering is altered. In the plasma separator module, whole blood enters the bio-artificial liver 144. The first module of this device is where plasma portion (P.P) as well as cellular portion (C.P) components of the whole blood is separated. This is accomplished using a plasmapheresis membrane. The P portion is further separated into a Rich Plasma Portion (RPP) and Serum Portion (SP) without the plasma proteins. The RPP will be returned to the patient. The S portion which contains the micro and macro nutrients are diverted to the next module. The C portion is further separated into RBC portion and the WBC/Platelets portion. The WBC+Platelets portion is returned to the patient. The RBC portion is directed to the next module. The next module is a microfluidic multilayer PDMS construct that has multiple copies of a two layered microfluidic channels that are alternating while being separated by ECMO membranes.

Bio-Artificial Bioreactors for Organ Support

This is simply a combination of the bioreactor organs in series with the 1) combined microfluidic kidney and liver dialysis device or 2) mobile, modular and scalable microfluidic-based kidney and/or liver dialysis device.

The Artificial Bioreactor Organs (Liver/Kidney/Pancreas etc.)

The Artificial Lung using various MCAL technology based microfluidic chipset units/modules The MCAL Technology is used to design a more efficient and/or portable microfluidics-based Artificial Lung. The multiple goals of this microfluidic Artificial Lungs are:
  To increase efficiency
  To increase surface area
  To decrease volume
  To increase SA/V ratio
  To increase diffusion
  To reduce the size of the unit
To achieve this we will tap into the microfluidic technology
  The First Design two to multilayered design (Using Whole Blood)
  1st Layer: Microfluidic channels: O1 Layer/(Air/oxygen channels)
  2nd Layer/only a membrane: M1 Layer/(ECMO Membrane Layer)
  3rd Layer: Microfluidic Channels: A1 Layer/(Whole Blood Cell channels)
  4th Layer/only a membrane: M2 Layer/ECMO Membrane Layer
  5th Layer: Microfluidic channels: O2 Layer/(Air/oxygen channels)
  Nth layer repeating O, M and A layers repeatedly as needed Second Design Two to Multilayered Design (Fractionated Blood)

Module 1: The Plasma Separator
1. Whole blood enters the Artificial Lung Device.
2. The first module of this device is MCAL Technology microfluidic chipset-PS Module where plasma portion (P.P) as well as cellular portion (C.P) components of the whole blood is separated.
3. This is accomplished using a plasmapheresis membrane.
4. The Plasma portion is returned to the patient.
7. The C.P. is further separated via another MCAL Technology microfluidic chipset-PSModule into RBC portion/Platelets portion and the WBC.
8. The WBC+portion is returned to the patient.
9. The RBC+Platelet portion is directed to the next module.

The next module is a microfluidic multilayer PDMS construct that has multiple copies of a three-layered microfluidic channels that are alternating while being separated by ECMO membranes.

Module 2: The Blood Oxygenator
1st Layer: Microfluidic channels: O1 Layer/(Air/oxygen channels) 2nd Layer/only a membrane: M1 Layer/ECMO Membrane Layer
3rd Layer: Microfluidic channels: A1 Layer/Pure RBC+ Portion channels)
4th Layer/only a membrane: M2 Layer/ECMO Membrane Layer
5th Layer: Microfluidic channels: O2 Layer/(Air/oxygen channels)
Nth layer repeating O, M and A layers repeatedly as needed.

The Bio artificial Organs (Artificial Liver is used here as an example)

PS Module: Plasma Separation Function. This microfluidic chipset module (PS module/unit) will use a plasmapheresis membrane over a microfluidic PDMS based channels to perform a plasmapheresis. Thereby, the input of the whole blood through this module will have two outputs 1) the cell portion (C.P.), which mainly contains the cellular components of the whole blood in small amount of plasma 2) the plasma portion (P.P.), which is devoid of any cellular elements. The C.P. output is then immediately directed to the bioreactor construct is a separate line, while the P.P. is directed to the bioreactor after going through the O module #2.

Chipset BR module (Bioreactor Chipset): Oxygenation of the hepatocytes in Bioreactor—This microfluidic Bioreactor will use a multilayer inert and biocompatible polymer used as microfluidic substrate such PDMS construct to achieve:

Oxygenate and provide nutrients as well as removal of the $CO_2$ using the C.P. which has a high hematocrit. The C.P. is directed to the outer two layers of the bioreactor. The nutrient and the oxygen is then delivered via two semipermeable membranes.

To bathe the hepatocytes (other organ/tissue/cells) in the hydrogel, the "dialyzed" P.P. from module #4 which will enter the central layer of the bioreactor. Hence the toxins left over from the dialysis device—the combined microfluidic-based kidney and Liver dialysis device is processed by any one of the bioreactors (kidney, liver, lung, and pancreas).

The two portions are then mixed and returned to the patient as whole blood. Note: may place a module here to clear metabolites from P.P before returning it to the patient.

Module #2: The P.P. portion is directed to this module and via a highly permeable dialysis membrane (high flux) will perform a very intensive hemodiafiltration which will perform an intensive ultrafiltration (convective dialysis) as well as diffusive dialysis. In the process the dialysate is passed in cross-flow against the P.P. and will have an output of U/F plus spent dialysis. The dialyzed P.P. will be directed to the next module.

Module #3: The Tubular Portion (Clearance Function) The P.P. will enter this module and will come in direct contact with reservoirs of resin and charcoal that are embedded into the PDMS chipset. Each channel has its own dedicated reservoir. In addition, to avoid saturation of these reservoirs of the charcoal and resin, a dialysate solution containing charcoal is used to regenerate these reservoirs. To achieve this, this special dialysate is run in a cross-flow pattern against a high flux dialysis membrane. The P.P. will be directed to the next module Module #4: The Tubular Section (Clearance Function) The P.P. is directed to a chip module with a special design with a multi-layer PDMS containing 5 layers. The middle layer is sandwiched between two mirror image layers. The P.P. is located in the central layer which is sandwiched between two identical layers containing dialysate+Albumin. These three layers are sandwiched between two identical layers containing dialysate+charcoal. The four membranes separating all five layers have characteristics of a High Molecular Weight Cut-Off dialysis membrane in order to achieve albumin dialysis.

A d construct of a biomimetic microfluidic Liver is a combination of 4 distinct modules that are connected in series as was described above. The whole blood is diluted in I:I to 1:4 whole blood/replacement fluid ratios which is then directed to run through the 4 distinct modules to achieve a very high quality and efficient dialysis.

Basic Design of a Liver Unit:
Each one of these artificial nephrons will have an approximate length of 1-12 cm.
L: 1-12 cm
W: 100-1000 um (100 um with its walls)
D: 10-50 um (shallow depth for faster diffusion)

All these liver lobules/units are placed in parallel to each other on the same chipset and on the same layer. Additional layers are added to increase the number of these liver units to emulate the native liver.

Figure 17:
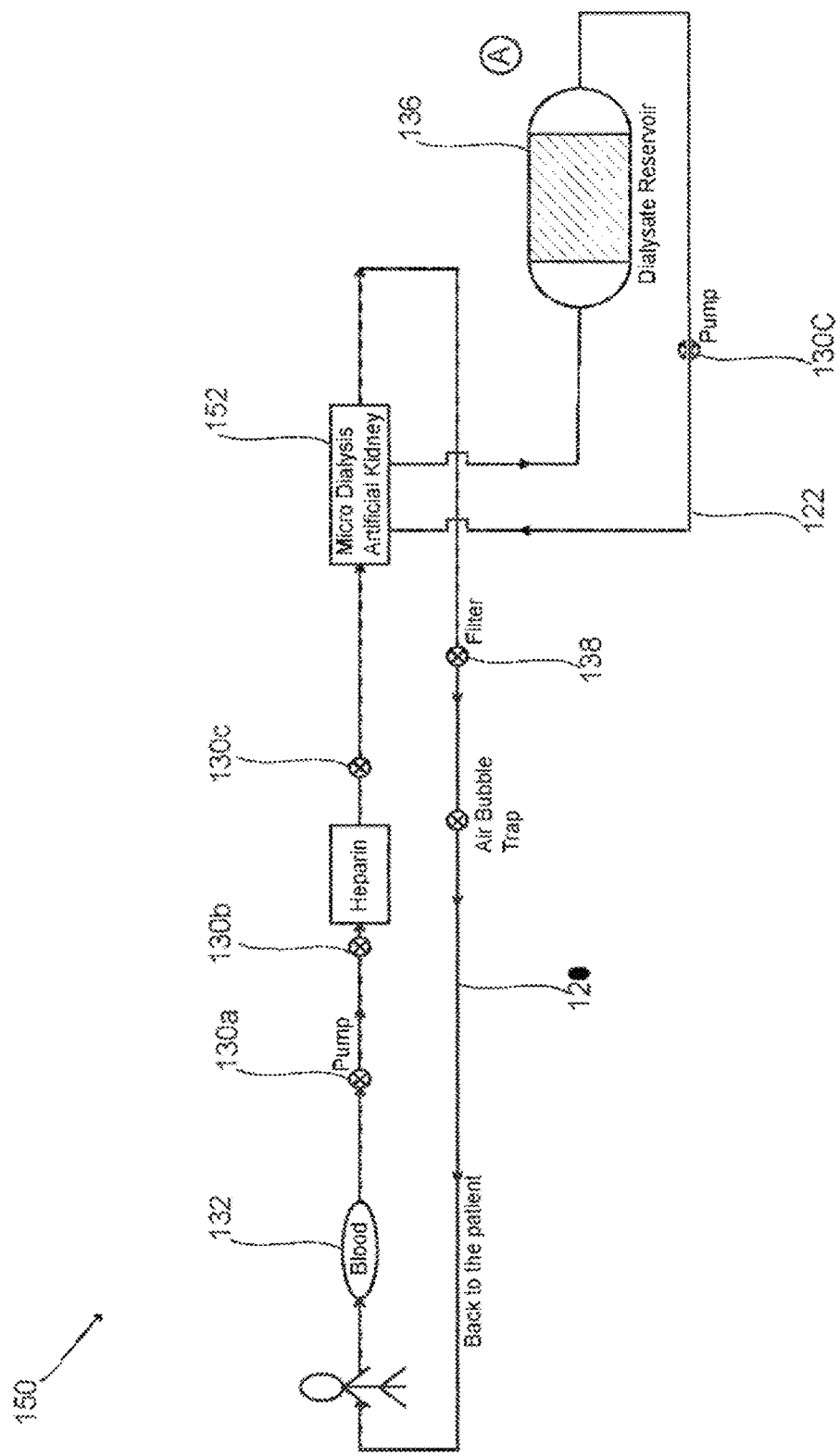
FIG. 17 illustrates a diagram of an exemplary artificial kidney dialysis system, in accordance with an embodiment of the present invention.

Looking now at the block diagram of FIG. 17, the blood is circulated from the body and through a bio-artificial kidney dialysis system 150. Similar as to the microfluidic units 102*a-d*, the micro-pumps 130*a-c* force the blood from the body to a bio-artificial kidney 152. In the illustrated embodiment, the bio-artificial kidney 152 is used for dialysis. Though, the bio-artificial liver 144 may also be used. In either case, they operate substantially the same as discussed above with the microfluidic units 102*a-d*. The contaminated dialysate 122 from the dialysis process in the bio-artificial kidney 152 may be redirected to an external filtering process consisting of: a forward dialyses 138, a reverse osmosis 140, and a waste reservoir 142 for catching the water, toxins, and small electrolytes. From this external filtering process, the partially filtered contaminated dialysate 122 flows to the microfluidic regenerating housing 128 containing a plurality of microfluidic regenerating units/modules 1 18*a-c*. The regenerated dialysate 120 then flows back to the bio-artificial liver 144 for further dialysis processing. A dialysate vial 136 may be used to add fresh dialysate to the regenerated dialysate 120.

Bio-Artificial Organ Support Systems (Combinations of #3 with #1 or #2)

The MCAL Technology core technology is further used to design a more efficient microfluidics based Bio-Reactor and Bio-artificial organ support system. The multiple goals of this microfluidic Bio-reactor is to replace/support failing organ/tissue Furthermore, this bio-reactor can be placed in series with MFC building blocks—such kidney and/or liver dialyzer to form a more complex Bio-Artificial organ support The Overall Design of the Bioreactor Utilizing the MCAL Technology Basic Units The bioreactors will be used to produce biomimetically designed microfluidic-based various artificial organs such as Liver, Kidney, Lungs or Pancreas and etc. The microfluidic chipset BR module can be filled with different tissues, cells, stem cells and supporting structures for preserving the living cells/tissue. For example, the artificial liver is consisting of several modules which are placed serially either continuously on the same chipset, or disjointed on different chipsets that are connected serially to emulate a human liver lobule. A large collection of these artificial liver lobules" make up an artificial liver. The modules are as follows: (See drawing #1, #2, #3 #4, #5 & #6) (Note: the whole blood may be diluted using replacement fluid before entering the module #1)

Microfluidic Based on Demand Intravenous Fluid and Dialysate Generator:

Microfluidic Intravenous Fluid Generator is intended to be an integrated medical component system capable of producing a variety of packaged i.v. fluids as well as high quality ultra-pure water supply for dialysate generation on demand and in quantities large enough to support field medical treatment facilities (MTF) that provide emergency resuscitative surgery and critical care.

The objective of microfluidic i.v. Fluid/Dialysate Generator is a novel design of using various microfluidic chipset units (modules) based on MCAL Technology to design and develop high quality ultra-pure water-source processing device consisting of integrated medical grade components. The device will be capable of producing packaged i.v. fluids for use by medical personnel in forward-deployed environments supporting initial and sustained military operations.

Starting with any quality tap water from any available water source, this microfluidic device—a stand-alone microfluidic Intravenous Fluid Generator device will produce a variety of i.v. fluid solutions which includes but not limited to dialysate fluids, replacement fluids, normal saline, half saline, dextrose and lactated Ringers Additionally, this device will be able to be operated by a single person.

For generating ultrapure water from tap water for intravenous use or dialysate use . . . . This will allow to generate different types of i.v. fluids for medical use Design of the Microfluidic Intravenous Fluid Generator:
Two Designs:
1. Ro system with prefilled special bags with specified electrolytes
2. Microfluidic RO system plus microfluidic mixer (optional)

The Overall Process:

The process of producing ultrapure water from tap water will be a combination of the following parts/layers. Of course this sterile water can be used to generate different types of i.v. fluid solutions using plastic bags with certain combination of electrolytes. When specific amount of fluid is add, the final concentration will be one of the seven major i.v. fluid solution bags ready for administration.

I. The Ultrafiltration Membrane Layer: (Optional as First Layer)
The feed water flows over the first layer which consists of an ultrafiltration membrane.

II. The Activated Charcoal Layer:
The cleaned water from the previous layer then flows over the second layer which contains activated charcoal.

III. The Nano-filtration Membrane Layer:
The cleaned water from the previous layer then flows over the third layer which consists of a nanofiltration membrane.

IV. The RO Membrane Layer:
The cleaned water from the previous layer then flows over the fourth layer which consists of a R.0. membrane.

V. The Deionizing Layer:
The Cleaned water from the previous layer then flows over the fifth layer which consists of a mixed-bed ion exchange resin.

The Ultrafiltration Membrane Layer.
The feed water flows over this last layer which consists of an ultrafiltration membrane.

Different Configurations of the Microfluidic Water Purification System Configurations/Modules:

I. Multilayer microfluidic chipset with its channels packed with microporous and mesoporous activated carbon. This module is for the carbon filter portion.

II. A multilayer microfluidic chipset designed to be used as the RO system. This three layered chipset module is composed of two mirror image microfluidic layers (inert and biocompatible polymer used as microfluidic substrate such as PDMS layers), which sandwich a central microfluidic layer (i.e. PDMS layer) with its both side covered with RO membranes. The flow of feed water is through the channels of the central compartment which produces ultrapure water through the outer two layers leaving behind brine. (Design #)

III. Continuous Electrodeionization (CED) chipset designed to be used as the deionization of the RO system output for total removal of anions and cations. This three layered cell is composed of two mirror image PDMS layer which are based on two thin layers of electrodes. One layer is placed on an electrode connecting to the DC current acting as an anode, and the other layer is placed on another electrode acting as the cathode.

The third layer's channels—the centralized PDMS—are filled with mixed bed ionic resins and are covered on both sides with specialized permeable ion exchange membranes. One side is covered with an anionic membrane and the other side with a cationic membrane. This combination is then sandwiched between the other two layers making sure that the PDMS layer with the positive electrode is placed on top of the central PDMS covering the cationic membrane side and the other one with the negative electrode is placed so it covers the anionic membrane.

A multilayer top down flow PDMS cell consisting of the followings (order maybe change to increase the fidelity of each step.

Feed water flows over the first layer composed of tightly micro- and mesoporous activated carbon. This layer is separated from the next layer by a microfiltration membrane. The next layer is a PDMS layer packed with mixed bed ion exchange resins. The water flows over this layer and moves through a nanofiltration membrane which separates it from the next layer. This PDMS layer is where RO occurs. The space is not filled with anything allowing the filling up the space for continuous RO water production. The next layer is an optional repeat of the first two layers with their corresponding membranes. These extra layers are placed as a backup in order to avoid super saturation and release of some of the contaminants from the 1st and 2nd layers These layers (repeat layers) are separated from the outflow channels by an ultrafiltration membrane.

1st layer: PDMS chips with many parallel channels are tightly packed with the activated carbon.

2nd layer: An ultrafiltration membrane is place at this level separating the first PDMS from the next.

3rd layer: PDMS chips with many parallel channels that act as a reservoir to build up the water for the slower process of the RO process. This PDMS chip is separated from the next layer via the RO membrane.

4th layer: specialized multilayer PDMS which is assembled in a top down fashion but is placed in this complex multilayered water purification device in a right (90 degree) angel and perpendicular manner to the other layers.

This Multilayered PDMS with its outer layers covered with electrodes on each side to act as an anode and cathode when connected to the DC current to run the continuous electrodeioniziation process. In between there are multiple layers of alternating anionic and cationic permeable ion exchange membranes. In addition, every other space between these alternating anionic and cationic membranes is filled with mixed bed ion exchange resins. The alternating spaces that do not contain the mixed ion exchange resins are closed off, therefore, all the concentrated water brine is accumulated and is drained off on the side. Meanwhile the pure water that is generated is forwarded to the next layer.

5th layer: this layer is an ultrafiltration membrane that is placed to ensure bacteria and other pathogens are effectively removed. The outflow of this layer is the ultrapure water that is used for generating ultrapure dialysate fluid for the purpose of hemodialysis. See all attached Figures and Diagrams.

It is significant to note that the ultrapure water produced will also be used to generate ultrapure dialysate fluid, using a microfluidic chip that uses a concentrated acid and base to combine it with the pure water in pre-specified ratio. (Microfluidic dialysate proportioning system)

I claim:

1. Various modular and scalable biomimetically designed microfluidic-based multilayered micro-channels separated by various semipermeable membranes, comprising:
 a plurality of microfluidic layers, the plurality of microfluidic layers configured to enable mass exchange and transfer of different substances in between adjacent microfluidic layers separated by basic semipermeable membranes in order to perform various forms of dialytic processes of whole blood and its components, plasma and its components, various tissues and its components, various cells, stems cells, a plurality of microfluidic units arranged in modular configuration for enabling scalability, the plurality of microfluidic, units at least partially fabricated from any inert and biocompatible polymer substrate as microfluidic substrate, the plurality of microfluidic units comprising:
  a double or multilayered microfluidic channels separated by the one or more basic semipermeable membranes of different characteristics configured to early various liquids with different composition and solution, blood and its components, plasma and its components, various formulation of dialysate including but not limited to albumin dialysate, lipid dialysate and charcoal and/or resin solution and/or hold various tissues and its components, cells, stem cells, various resins, charcoal and ion exchange resins and other adsorbing substance:
  a multilayered microfluidic chipset unit with the intervening basic semipermeable membranes comprising a plurality of micro-pumps, the plurality of micro-pumps configured to pump the various liquids with different compositions, various dialysate formulations, blood, or plasma to and from the multilayered microfluidic chipset unit,
  the multilayered microfluidic chipset unit and its intervening basic semipermeable membranes further comprising a plurality of micro-valves, the plurality of micro-valves configured to regulate the flow of the fluid and the blood, tissue, or plasma,
  the multilayered microfluidic chipset unit and its intervening basic semipermeable membranes further comprising a plurality of micro-channels, the plurality of micro-channels defined by a topography having a substantially microvasculature configuration, the plurality of micro-channels further defined by varying widths, the plurality of micro-channels configured to carry the blood and its components, plasma and its components, tissue, or various cells to and from the microfluidic chipset unit and hold them in place, the plurality of micro-channels further configured to carry various liquids with different compositions, various dialysate compositions including albumin, lipid and charcoal and resin solutions to and from the microfluidic chipset unit; and
  at least two basic semipermeable membranes disposed between the different layers of the microfluidic chipset unit, the at least two basic semipermeable membranes configured to form a permeable barrier between the fluid and the blood, tissue, or plasma, the at least two basic semipermeable membranes further configured to enable passage of different substances including but not limited to nutrients, water, electrolytes, toxins and other important growth factors and hormones from one layer to its adjacent layer of the multilayered microfluidic chipset unit; and
  at least two basic semipermeable membranes disposed between the multilayered microfluidic chipset unit, the at least two basic semipermeable membranes configured to form a permeable barrier between two adjacent microfluidic layers containing any type of fluids, various solutions, various dialysate compositions, blood and its components, plasma and its components, various tissues and their components, cells, stem cells, or plasma, the at least two basic semipermeable membranes further configured to enable passage of various substances, molecules, electrolytes, micro and macro-nutrients, toxins, water and various gases/air from one layer to its adjacent layers in the microfluidic chipset unit; and
 a plurality of microfluidic regenerating units, the plurality of microfluidic regenerating units configured to at least partially filter spent dialysate or contaminated fluid received from at least one multilayered microfluidic chipset dialysis units, the plurality of microfluidic regenerating units further configured to return regenerated fluid as fresh dialysate to the multilayered microfluidic chipset dialysis unit.

2. The microfluidic-based multilayered micro-channels separated by various semipermeable membranes of claim 1, wherein the at least two basic semipermeable membranes are configured to be interchangeable.

3. The microfluidic-based multilayered micro-channels separated by various semipermeable membranes of claim 1, wherein the at least two basic semipermeable membranes are arranged in at least two permutations, the at least two permutations configured to enable development of a dialysis device to perform kidney and/or liver dialysis for organ replacement and bio-artificial organ.

4. The microfluidic-based multilayered micro-channels separated by various semipermeable membranes of claim 1, wherein the at least two basic semipermeable membranes are arranged in at least two permutations, the at least two permutations configured to enable development of a bioreactor organ or a bio-artificial organ, and replacement of an organ or bio-artificial organ.

5. The microfluidic-based multilayered micro-channels separated by various semipermeable membranes of claim 1, wherein the at least two basic semipermeable membranes are configured to emulate at least one of the following: a kidney, a liver, a capillary, and a lymphatic.

6. The microfluidic-based multilayered micro-channels separated by various semipermeable membranes of claim 1, wherein the at least two basic semipermeable membranes comprises a hemodialysis filter.

7. The microfluidic-based multilayered micro-channels separated by various semipermeable membranes of claim 1, wherein the at least two basic semipermeable membranes comprises an ultrafiltration filter.

8. The microfluidic-based multilayered micro-channels separated by various semipermeable membranes of claim 1, wherein the at least two basic semipermeable membranes comprises a plasma separation or plasmapheresis filter.

9. The microfluidic-based multilayered micro-channels separated by various semipermeable membranes of claim 1, wherein the at least two basic semipermeable membranes comprises a hemoperfusion filter.

10. The microfluidic-based multilayered micro-channels separated by various semipermeable membranes of claim 1, wherein the at least two basic semipermeable membranes comprises an albumin dialysis filter.

11. The microfluidic-based multilayered micro-channels separated by various semipermeable membranes of claim 1, wherein the at least two Previously presented semipermeable membranes comprises a diafiltration filter.

12. The microfluidic-based multilayered micro-channels separated by various semipermeable membranes of claim 1, wherein the at least two basic semipermeable membranes comprises a hemodiafiltration filter.

13. The microfluidic-based multilayered micro-channels separated by various semipermeable membranes of claim 1, wherein the at least two basic semipermeable membranes comprises a dialysate regeneration filter.

14. The microfluidic-based multilayered micro-channels separated by various semipermeable membranes of claim 1, wherein the at least two basic semipermeable membranes comprises an oxygenation filter.

15. The microfluidic-based multilayered micro-channels separated by various semipermeable membranes of claim 1, wherein at least two basic semipermeable membranes comprises a hemodialysis/high efficiency filter.

16. The microfluidic-based multilayered micro-channels separated by various semipermeable membranes of claim 1, wherein at least two basic semipermeable membranes comprises an albumin dialysis and regeneration filter.

17. The microfluidic-based multilayered micro-channels separated by various semipermeable membranes of claim 1, wherein the at least two basic semipermeable membranes comprises a tissue support filter, the tissue support filter comprising a molecular weight cut-off membrane cutting off up to the molecular weight of 4000 kDA.

18. The microfluidic-based multilayered micro-channels separated by various semipermeable membranes of claim 1, wherein the at least two basic semipermeable membranes comprises a reverse osmosis filter.

19. The microfluidic-based multilayered micro-channels separated by various semipermeable membranes of claim 1, wherein the at least two basic semipermeable membranes comprises a forward osmosis filter.

20. The microfluidic-based multilayered micro-channels separated by various semipermeable membranes of claim 1, wherein the at least two basic semipermeable membranes comprises an electrodeionization filter.

21. The microfluidic-based multilayered micro-channels separated by various semipermeable membranes of claim 1, wherein the at least two basic semipermeable membranes comprises an electrodialysis filter.

22. The microfluidic-based multilayered micro-channels separated by various semipermeable membranes of claim 1, wherein the at least two basic semipermeable membranes comprises an electrofiltration filter.

23. The microfluidic-based multilayered micro-channels separated by various semipermeable membranes of claim 1, wherein the at least two basic semipermeable membranes comprises a lipid dialysis filter.

24. The microfluidic-based multilayered micro-channels separated by various semipermeable membranes of claim 1, wherein the fluid comprises at least one of the following: dialysate, plasma, oxygen, blood, and nutrients.

25. The microfluidic-based multilayered micro-channels separated by various semipermeable membranes of claim 1, wherein plurality of micro-pumps comprise electric micro-pumps and pneumatic micro-pumps.

26. The microfluidic-based multilayered micro-channels separated by various semipermeable membranes of claim 1, wherein plurality of micro-pumps comprise two blood micropumps, a heparin micro-pump, an ultrafiltration micro-pump, and a dialysate micropump.

27. The microfluidic-based multilayered micro-channels separated by various semipermeable membranes of claim 1, wherein the plurality of micro-channels have one or various and varying inlet and outlet.

28. The microfluidic-based multilayered micro-channels separated by various semipermeable membranes of claim 1, wherein the plurality of micro-channels are configured in substantially the same topography and width and/or depth as a microvasculature of the body.

29. The microfluidic-based multilayered micro-channels separated by various semipermeable membranes of claim 1, wherein the plurality of micro-channels have a width of about 100-2000 microns, a depth of about between 10 to 200 microns, and a length of about between 1 to 20 centimeters.

30. The microfluidic-based multilayered micro-channels separated by various semipermeable membranes of claim 1, wherein the topography of the plurality of micro-channels include at least one member selected from the group consisting of: straight, parallel, crisscross, fractal, loop, interrupted with pillars and branched.

31. The microfluidic-based multilayered micro-channels separated by various semipermeable membranes of claim 1, wherein the plurality of microfluidic regenerating units includes at least one member selected from the group consisting of: a sediment filter, a carbon filter, a zirconium carbonate filter, a deionizing resin, a micro-filter, charcoal, an ultraviolet light, and a cold plasma production for sterilization and regeneration apparatus.

32. The microfluidic-based multilayered micro-channels separated by various semipermeable membranes of claim 1, further comprising a warming device, the warming device configured to warm up the whole or sections of the device to warm up activated charcoal or other components of blood, plasma or various dialysates.

33. The microfluidic-based multilayered micro-channels separated by various semipermeable membranes of claim 1, further comprising a cooling device.

34. The microfluidic-based multilayered micro-channels separated by various semipermeable membranes of claim 1, wherein dialysate is a pure or an ultrapure dialysate.

35. The microfluidic-based multilayered micro-channels separated by various semipermeable membranes of claim 1, wherein dialysate is a mixture of a charcoal and or resin solution in a pure or an ultrapure dialysate.

36. The microfluidic-based multilayered micro-channels separated by various semipermeable membranes of claim 1, wherein the dialysate is a sterile and biocompatible and safe lipid solution.

* * * * *